(12) United States Patent
Vaezy et al.

(10) Patent No.: US 7,520,856 B2
(45) Date of Patent: Apr. 21, 2009

(54) IMAGE GUIDED HIGH INTENSITY FOCUSED ULTRASOUND DEVICE FOR THERAPY IN OBSTETRICS AND GYNECOLOGY

(75) Inventors: Shahram Vaezy, Seattle, WA (US); Arthur H. Chan, Plano, TX (US); Victor Y. Fujimoto, San Francisco, CA (US); Donald E. Moore, Seattle, WA (US); Roy W. Martin, Anacortes, WA (US)

(73) Assignee: University of Washington, Seattle, WA (US)

( * ) Notice: Subject to any disclaimer, the term of this patent is extended or adjusted under 35 U.S.C. 154(b) by 696 days.

(21) Appl. No.: 10/977,339

(22) Filed: Oct. 29, 2004

(65) Prior Publication Data

US 2005/0203399 A1    Sep. 15, 2005

Related U.S. Application Data

(60) Continuation-in-part of application No. 10/770,350, filed on Feb. 2, 2004, which is a continuation-in-part of application No. 10/166,795, filed on Jun. 7, 2002, now Pat. No. 6,716,184, which is a division of application No. 09/397,471, filed on Sep. 17, 1999, now Pat. No. 6,425,867.

(60) Provisional application No. 60/516,099, filed on Oct. 31, 2003.

(51) Int. Cl.
*A61B 8/00* (2006.01)
*A61N 7/00* (2006.01)

(52) U.S. Cl. .......................... 600/439; 600/459; 601/3

(58) Field of Classification Search ................. 600/437, 600/439, 459; 601/2–4
See application file for complete search history.

(56) References Cited

U.S. PATENT DOCUMENTS

RE33,590 E     5/1991   Dory ..................... 128/660.03

(Continued)

FOREIGN PATENT DOCUMENTS

DE             04230415 A1    3/1994

(Continued)

OTHER PUBLICATIONS

Accord, Ray E. "The Issue of Transmurality in Surgical Ablation for Atrial Fibrillation," Cardiothoracic Surgery Network, Aug. 8, 2005.

(Continued)

*Primary Examiner*—Francis J. Jaworski
(74) *Attorney, Agent, or Firm*—Ronald M. Anderson

(57) ABSTRACT

A frame ensures that the alignment between a high intensity focused ultrasound (HIFU) transducer designed for vaginal use and a commercially available ultrasound image probe is maintained, so that the HIFU focus remains in the image plane during HIFU therapy. A water-filled membrane placed between the HIFU transducer and the treatment site provides acoustic coupling. The coupling is evaluated to determine whether any air bubbles exist at the coupling interface, which might degrade the therapy provided by the HIFU transducer. HIFU lesions on tissue appear as hyperechoic spots on the ultrasound image in real time during application of HIFU therapy. Ergonomic testing in humans has demonstrated clear visualization of the HIFU transducer relative to the uterus and showed the potential for the HIFU transducer to treat fibroids from the cervix to the fundus through the width of the uterus.

44 Claims, 30 Drawing Sheets

U.S. PATENT DOCUMENTS

| | | | |
|---|---|---|---|
| 5,039,774 A | 8/1991 | Shikinami et al. | 528/60 |
| 5,065,742 A | 11/1991 | Belikan et al. | 128/24 |
| 5,080,101 A | 1/1992 | Dory | 128/660.03 |
| 5,080,102 A | 1/1992 | Dory | 128/660.03 |
| 5,150,712 A | 9/1992 | Dory | 128/660.03 |
| 5,170,790 A * | 12/1992 | Lacoste et al. | 600/437 |
| 5,178,148 A * | 1/1993 | Lacoste et al. | 600/439 |
| 5,219,401 A | 6/1993 | Cathignol et al. | 128/660.03 |
| 5,311,869 A | 5/1994 | Okazaki | 128/660.03 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/660.03 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,522,878 A | 6/1996 | Montecalvo et al. | 607/152 |
| 5,526,815 A | 6/1996 | Granz et al. | 128/660.03 |
| 5,558,092 A | 9/1996 | Unger et al. | 128/660.03 |
| 5,573,497 A | 11/1996 | Chapelon | 601/2 |
| 5,666,954 A * | 9/1997 | Chapelon et al. | 600/439 |
| 5,720,286 A | 2/1998 | Chapelon et al. | 600/439 |
| 5,720,287 A | 2/1998 | Chapelon et al. | 600/439 |
| 5,762,066 A | 6/1998 | Law et al. | 600/439 |
| 5,769,790 A | 6/1998 | Watkins et al. | 600/439 |
| 5,810,007 A * | 9/1998 | Holupka et al. | 600/439 |
| 5,817,021 A | 10/1998 | Reichenberger | 600/439 |
| 5,823,962 A | 10/1998 | Schaetzle et al. | 600/439 |
| 5,827,204 A | 10/1998 | Grandia et al. | 601/2 |
| 5,873,828 A | 2/1999 | Fujio et al. | 600/439 |
| 5,895,356 A | 4/1999 | Andrus et al. | 600/439 |
| 5,931,786 A * | 8/1999 | Whitmore et al. | 600/459 |
| 5,976,092 A * | 11/1999 | Chinn | 600/459 |
| 5,993,389 A | 11/1999 | Driscoll, Jr. et al. | 600/371 |
| 6,007,499 A | 12/1999 | Martin et al. | 601/3 |
| 6,039,694 A | 3/2000 | Larson et al. | 600/459 |
| 6,050,943 A | 4/2000 | Slayton et al. | 600/439 |
| 6,179,831 B1 | 1/2001 | Bliweis | 606/21 |
| 6,221,015 B1 | 4/2001 | Yock | 600/439 |
| 6,409,720 B1 | 6/2002 | Hissong et al. | 606/27 |
| 6,425,867 B1 | 7/2002 | Vaezy | 600/439 |
| 6,488,639 B1 * | 12/2002 | Ribault et al. | 601/2 |
| 6,491,672 B2 | 12/2002 | Slepian et al. | 604/267 |
| 6,595,934 B1 | 7/2003 | Hissong et al. | 601/3 |
| 6,599,256 B1 | 7/2003 | Acker et al. | 601/2 |
| 6,626,855 B1 | 9/2003 | Weng et al. | 601/3 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,716,184 B2 | 4/2004 | Vaezy et al. | 601/3 |
| 6,719,699 B2 | 4/2004 | Smith | 600/459 |
| 6,764,488 B1 | 7/2004 | Burbank et al. | 606/51 |
| 6,846,291 B2 | 1/2005 | Smith et al. | 600/459 |
| 2002/0193681 A1 | 12/2002 | Vitek et al. | 600/411 |
| 2003/0069569 A1 | 4/2003 | Burdette et al. | 606/27 |
| 2003/0125623 A1 | 7/2003 | Kelly et al. | 600/437 |
| 2004/0019278 A1 | 1/2004 | Abend | 600/545 |
| 2004/0030268 A1 | 2/2004 | Weng et al. | 601/2 |
| 2004/0059220 A1 | 3/2004 | Mourad et al. | 600/442 |
| 2004/0078034 A1 | 4/2004 | Acker et al. | 606/27 |
| 2004/0097805 A1 | 5/2004 | Verard et al. | 600/428 |
| 2004/0097840 A1 | 5/2004 | Holmer | 601/2 |
| 2004/0143186 A1 | 7/2004 | Anisimov et al. | 600/437 |
| 2004/0153126 A1 | 8/2004 | Okai | 607/1 |
| 2004/0181178 A1 | 9/2004 | Aldrich et al. | 601/3 |
| 2004/0234453 A1 | 11/2004 | Smith | 424/9.5 |

FOREIGN PATENT DOCUMENTS

| | | | |
|---|---|---|---|
| EP | 01265223 B1 | 11/2002 | |
| WO | WO 00/72919 | 12/2000 | |

OTHER PUBLICATIONS

"Mechanical Bioeffects in the prescence of gas/carrier ultrasound contrast agents." J Ultrasound Med. 19: 120/142, 2000.

Anand, Ajay et al. "Using the ATL 1000 to Collect Domodulated RF Data for Monitoring HIFU Lesion Formation." Center for Industrial and Medical Ultrasound, University of Washington. Abstract. 11pp. (2003).

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305-1320, 1999. Copyright 1999 World Federation for Ultrasound in Medicine & Biology.

Chen, Wen/Shiang, et al. "A comparison of the fragmentation thresholds and inertial cavitation doses of different ultrasound contrast agents." J. Acoust. Soc. Am. 113 (1), Jan. 2003: pp. 643-651.

Chen, Wen/Shiang, et al. "Inertial Cavitation Dose and Hemolysis Produced in Vitro with or Without Optison." Ultrasound in me. & Biol., vol. 29, No. 5, pp. 725-737, 2003.

Dayton, Paul, A., et al. "The magnitude of radiation force on ultrasound contrast agents." J. Acoust. Soc. Am. 112 (5) Pt. 1, Nov. 2002: pp. 2183-2192.

Everbach, Carr, E. and Charles W. Francis. "Cavitational Mechanisms in Ultrasound/Accelerated Thrombolysis at 1 MHz." Ultrasound in Med. & Biol., vol. 26, No. 7, pp. 1153-1160, 2000. Copyright 2000 World Federation in Medicine and Biology.

Guzman, Hector R., et al. "Ultrasound—Mediated Disruption of Cell Membranes. I. Quantification of Molecular uptake and Cell Viability." J. Acoust. Soc. Am. 110 (1), Jul. 2001: pp. 588-595.

Guzman, Hector R., et al. "Ultrasound/mediated disruption of cell membranes. II. Heterogeneous effects on cells." J. Acoust. Soc. Am 110 (1), Jul. 2001: pp. 597-606.

Hatangadi, Ram Bansidhar. "A Novel Dual Axis Multiplanar Transesophageal Ultrasound Probe for Three-Dimensional Echocardiograph." University of Washington, Department of Sciences and Engineering. (1994), Abstract. vol. 55-11B: 4960pp.

Holt, Glynn, R., Roy, Ronald, A., Edson, Patrick A., Yang, Xinmai. "Bubbles and Hifu: the Good, the Bad and the Ugly." Boston University, Department of Aerospace and Mechanical Engineering, Boston, MA 02215: 120/131. (2003).

Hynynen, Kullervo, et al. "Potential Adverse Effects of High/Intensity Focused Ultrasound Exposure on Blood Vessels in Vivo." Ultrasound in Med. & Biol., vol. 22, No. 2, pp. 193-201, 1996.

Ka/yun Ng, Yang Liu. "Therapeutic Ultrasound: Its Application in Drug Delivery." Medicinal Research Reviews, vol. 22, 204/223, 2002 © 2002 John Wiley & Sons, Inc.

Miller, Morton W. et al. "A Review of In Vitro Bioeffects of Intertial Ultrasonic Cavitation From a mechanistic Perspective." Ultrasound in Med & Biol., vol. 22, No. 9, pp. 1131-1154, 1996.

Nobuki Kudo, Takehiro Miyaoka, Kengo Okada, and Katsuyuki Yamamoto. "Study on Mechanism of Cell Damage Caused by Microbubbles Exposed to Ultrasound." Graduate School of Engineering, Hokkaido University, Japan, Research Institute for Electronic Science, Hokkaido University, 060/0812 Japan, (2002).

Owaki, T., Nakano, S. Arimura, K., Aikou, T. "The Ultrasonic Coagulating and Cutting System Injuries Nerve Function." First Department of Surgery, Kagoshima University School of Medicine, Kagoshima, Japan, Endoscopy. (2002) 575/579.

Poliachik, Sandra L., et al. "Activation, Aggregation and Adhesion of Platelets Exposed to High/Intensity Focused Ultrasound." Ultrasound in Med. & Biol., vol. 27, No. 11, pp. 1567-1576, 2001.

Poliachik, Sandra L., et al. "Effect of High-Intensity Focused Ultrasound on Whole Blood with or without Microbubble Contrast Agent." Ultrasound in Med. & Biol., vol. 25, No. 6, 1999: 991/998.

Porter, T.R., Xie, F. "Ultrasound, Microbubbles and Thrombolysis." Progress in Cardiovascular Diseases, vol. 44, No. 2, Oct. 2001: 101/110.

Rivens, I.H., Rowland, I.J., Denbow, M., Fisk, N.M., Harr, G.R., Leach, M.O. "Vascular occlusion using focused ultrasound surgery for use in fetal medicine." *European Journal of Ultrasound* 9 (1999): 89/97.

Rosenschein, Uri, et al. "Ultrasound Imaging/Guided Nonivasive Ultrasound Thrombolysis/Preclinical Results." © 2000 American Heart Association, Inc. (Circulation. 2000;102:238/245.) <http://www.circulationaha.com.org>.

Rosenschein, Uri, et al. "Shock/Wave Thrombus Ablation, A New Method for Noninvasive Mechanical Thrombolysis." The American Journal of Cardiology, vol. 70, Issue 15, Nov. 1992: pp. 1358-1361.

Tachibana, Katsuro and Shunro MD., PhD. "The Use of Ultrasound for Drug Delivery." *First Department of Anatomy, Fukuoka University School of Medicine*, Nanakuma, Japan,Echocardiography. (2001) 323/328.

Tachibana, Katsuro, and Shunro M.D., Ph.D. "Albumin Microbubble Echo/Contrast Material as an Enhancer for Ultrasound Accelerated Thrombolysis." (Circulation, 1995; 92: 1148/1150.) © 1995 American Heart Association, Inc.

Vaezy, Shahram et al. 2001. "Acoustic surgery." *Physics World* (August): 35/39.

Vaezy, Shahram et al. 2001. "Experimental Investigations and Device Development." First International Workshop on the Application of HIFU in Medicine. (May 10-13); 4pp.

Kaczkowski, Peter J., Vaezy, Shahram, Martin, Roy, Crum, Lawrence,. "Development of a High Intensity Focused Ultrasound System for image-guided ultrasonic surgery." Ultrasound for Surgery 2001. <http://cimu.apl.washington.edu/hifusurgerysystem.html>.

Physicians. "Breast Cancer—Insightec: focused ultrasound for non invasive treatment." FAQ <http://www.exablate2000.com/physicians_faq.html>.

Ostensen, Jonny, PhD; Bendiksen, Ragner, MSc. "Characterization and Use of Ultrasound Contrast Agents." *Acad. Radiol* 2002; 9(suppl 2):S276-S278.

Klibanov, Alexander L; Rasche, Peter T.; Hughes, Michael S.; Wojdyla, Jolette K.; Galen, Karen P.; Wiblee, James H.; Brandenburger, Gary H.. "Detection of Individual Microbubbles of an Ultrasound contrast Agent: Fundamental and Pulse Inversion Imaging[1]." *Acad Radiol* 2002, 9(suppl 2):S279-S281.

Bauer, A.; Solbiati, L.; Weissman, N. "Ultrasound Imaging with Sono Vue: Low Mechanical Index Real-time Imaging." *Acad Radiol* 2002, 9(suppl 2):S282-S284.

Watkin, Kenneth L., PhD; McDonald, Michael A., BS. "Multi-Modal Contrast Agents: A First Step[1]." *Acad Radiol* 2002, 9(suppl 2):S285-S287.

Watkin, Kenneth L., PhD; McDonald, Michael A., BS. "Schematic of the Tube, Cross Section Ultrasound Images of the Tube With Different Contrast Media (CM)." *Acad Radiol* 2002, 9(suppl 2):S288-S289.

Wickline, Samuel A., MD; Hughes, Michael, PhD; Ngo, Francis C., MD; Hall, Christopher, S., PhD; Marsh, Jon, N., PhD; Brown, Peggy A; Allen, John S., BS; McLean, Mark D.; Scott, Michael J., BS; Fuhrhop, Ralph W.; Lanza, Gregory M., MD, PhD. "Blood Contrast Enhancement with a Novel, Non-Gaseous Nanoparticle Contrast Agent[1]," *Acad Radiol* 2002, 9(suppl 2):S290-S293.

Tardy, I.; Pochon, S.; Theraulaz, P. Nanjappan; Schneider, M. "In Vivo Ultrasount Imaging of Thrombi Using a Target-specific Contrast Agent[1]." *Acad Radiol* 2002, 9(suppl 2):S294-S296.

Indman, Paul, MD,. "Alternatives in Gynecology." Hysteroscopy©2000 OBGYN.net <http://www.gynalternatives.com/hsc.html>.

\* cited by examiner

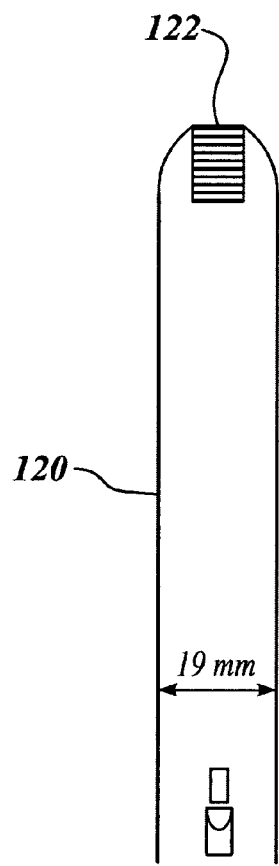
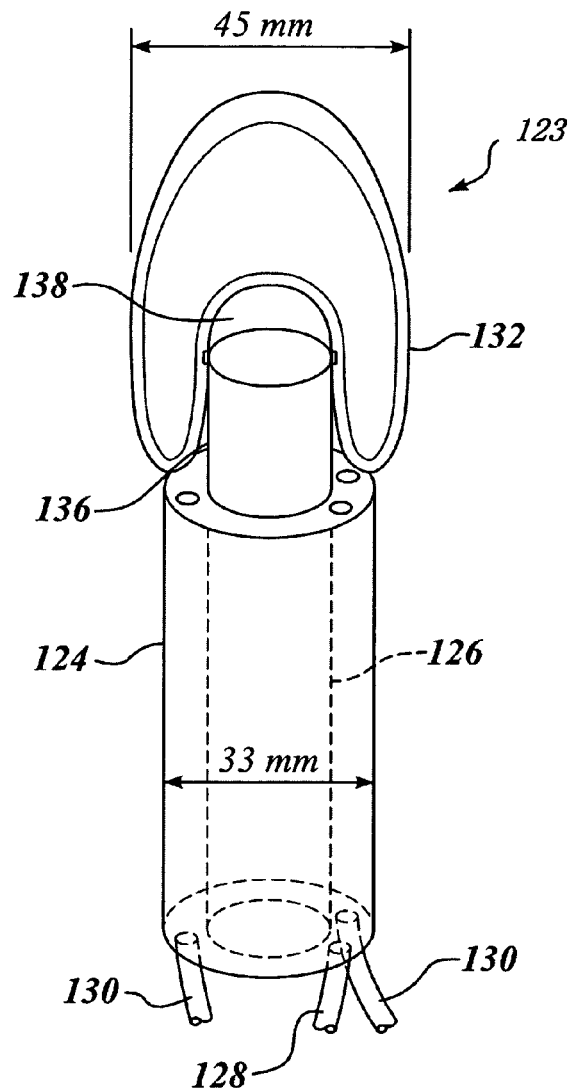
FIG. 3A
PRIOR ART
FIG. 3B

50% HIFU = ~ 67° visualization

Location of spatially stable interference bands can be shifted

IMAGE GUIDED HIGH INTENSITY FOCUSED ULTRASOUND DEVICE FOR THERAPY IN OBSTETRICS AND GYNECOLOGY

RELATED APPLICATIONS

This application is based on a prior provisional application Ser. No. 60/516,099, filed on Oct. 31, 2003, the benefit of the filing date of which is hereby claimed under 35 U.S.C. § 119(e). Further, this application is a continuation-in-part application of prior copending application Ser. No. 10/770, 350, filed on Feb. 2, 2004, which itself is a continuation-in-part application of prior application Ser. No. 10/166,795, filed on Jun. 7, 2002 and now issued as U.S. Pat. No. 6,716,184, which itself is a divisional application of prior application Ser. No. 09/397,471, filed on Sep. 17, 1999 and now issued as U.S. Pat. No. 6,425,867, the benefit of the filing dates of which is hereby claimed under 35 U.S.C. § 120.

GOVERNMENT RIGHTS

This invention was funded at least in part with grants (No. N00014-01-G-0460 and N00014-01-96-0630) from the Department of the Navy, and from a grant (No. 2 R42 HD38440-02) from the National Institutes of Health, and the U.S. government may have certain rights in this invention.

FIELD OF THE INVENTION

The present invention generally relies on the use of real-time ultrasound imaging to enhance therapy utilizing high intensity focused ultrasound, and more specifically, relies on the use of a frame to maintain a spatial orientation between a therapy device and an imaging probe during a therapeutic treatment using high intensity ultrasound.

BACKGROUND OF THE INVENTION

High intensity focused ultrasound (HIFU) has emerged as a precise, non-surgical, minimally-invasive treatment for benign and malignant tumors. At focal intensities (1000-10000 W/cm$^2$) that are 4-5 orders of magnitude greater than that of diagnostic ultrasound (approximately 0.1 W/cm$^2$), HIFU can induce lesions (i.e., localized tissue necrosis) at a small, well defined region deep within tissue, while leaving intervening tissue between the HIFU transducer and the focal point substantially unharmed. Tissue necrosis is a result of tissue at the focal point of the HIFU beam being heated to over 70° C. in a very short period of time (generally less than one second). Tissue necrosis also results from cavitation activity, which causes tissue and cellular disorganization. HIFU is currently being used clinically for the treatment of prostate cancer and benign prostatic hyperplasia, as well as the treatment of malignant bone tumors and soft tissue sarcomas. Clinical trials are currently being conducted for HIFU treatment of breast fibroadenomas, and various stage-4 primary and metastatic cancerous tumors of the kidney and liver.

Uterine fibroids are benign tumors of the uterus that cause abnormal uterine bleeding. The incidence of fibroids in women in their reproductive years has been estimated to be 20-25%, although autopsy studies show an incidence to be greater than 75%. Approximately ⅓ of women experiencing uterine fibroids will have a tumor that is symptomatic requiring treatment. Approximately 30% of all hysterectomies are related to the presence of uterine fibroids. Current treatment methods for uterine fibroids include both drug therapy and surgery. Experience with drug therapy shows almost a 100% rate of tumor reoccurrence once the drug therapy has stopped, and the drug therapy has numerous undesirable side effects. The rate of reoccurrence is significantly less for the surgical therapy (about 15%). Unfortunately, most current procedures for removing uterine fibroids are based on invasive surgical techniques, which require a significant recovery period and involve significant risks (such as blood loss, damage to related organs, and the ever present risk of infection). It is estimated that uterine fibroid procedures in the United States alone account for 1.2 to 3.6 billion dollars in annual medical costs.

It appears that HIFU, delivered using a transvaginal transducer, could provide a minimally-invasive treatment for uterine fibroids. On Oct. 22, 2004, the United States Food and Drug Administration (FDA) approved the ExAblate 2000™ System; a new medical device that uses magnetic resonance image (MRI) guided focused ultrasound to target and destroy uterine fibroids. While MRI guided HIFU therapy offers an alternative to more invasive surgical techniques, MRI equipment is very expensive, not nearly as available as ultrasound imaging devices, and not nearly as portable as ultrasound imaging devices. It would be desirable to provide a less costly alternative to MRI guided HIFU therapy. Such treatment is expected to compare favorably with the costs for the current drug related therapy for the treatment of uterine fibroids and its efficacy should compare favorably with the higher success rate of the current surgical procedures, but without the attendant risks.

SUMMARY OF THE INVENTION

A first aspect of the invention is directed to a support configured to spatially align a transvaginal HIFU applicator and a transabdominal ultrasound-imaging probe. The support ensures that the focal point of the HIFU beam is always visible in the image plane of the imaging transducer, regardless of the motion of the patient, the HIFU applicator, or the transabdominal ultrasound-imaging probe. In a particularly preferred embodiment, the support is configured to enable a variety of ubiquitous transabdominal ultrasound-imaging probes to be used with a newly developed transvaginal therapy probe. The support enables the transabdominal imaging probe and the transvaginal therapy probe to be moved independently of each other, when corresponding adjustment members are in an unsecured state, so that each probe can be properly positioned relative to the patient and the treatment site. The therapy probe is energized at a low power setting sufficient to enable the imaging probe to image the focal point of the therapy probe. As long as the therapy probe is energized at a low power level, no undesirable tissue necrosis will occur while the spatial orientation between the imaging probe and the therapy probe is being adjusted. The clinician can thus readily modify the spatial orientation of the imaging probe and the therapy probe, while the therapy probe is energized at the low power level, until the focal point of the therapy probe lies within the imaging plane provided by the imaging probe (i.e., until the focal point is visualized in an ultrasound image provided by the imaging probe). Once the desired focal point of the therapy probe relative to that of the imaging probe is thus achieved to deliver HIFU to the treatment site, the adjustment members are secured and the spatial orientation between the imaging probe and the therapy probe is fixed. At this point, the therapy probe can be energized at a higher power to initiate HIFU therapy. During this therapy, the therapy transducer is synchronized to the imaging transducer so as to ensure that noise generated by the HIFU beam is shifted to a portion of the ultrasound image (generated by the imaging probe) spaced apart from the portion of the ultrasound image in which the focal point of the HIFU beam is displayed.

Another aspect of this invention is directed to a transvaginal probe that includes a HIFU transducer optimized for the treatment of uterine fibroids from within the vagina. In one embodiment, the transvaginal probe includes a piezoceramic crystal bonded to an aluminum lens, to achieve a HIFU transducer having a focal length of about 4 cm. In another embodiment, the transvaginal probe includes a generally spoon-shaped transducer, which comprises a plurality of individual emitter elements.

Still another aspect of the present invention is directed to a method for evaluating a quality of a coupling between a liquid-filled volume encompassing a HIFU transducer and a tissue interface. HIFU transducers, or a portion of a probe containing a HIFU transducer, are often disposed inside a liquid-filled membrane. The fluid helps enhance the propagation of the HIFU beam by coupling the beam into the adjacent tissue. If any air bubbles are present between the liquid-filled membrane and the tissue interface, they will negatively affect the HIFU treatment by reducing the power of the HIFU transferred to the tissue. In a first embodiment, a hysterscope is used to visually detect the presence of such bubbles. The hysterscope can be a separate instrument, or can be integrated into the HIFU probe. In a second embodiment, the HIFU transducer is first energized at a lower power setting. If any air bubbles are present in the tissue interface, a portion of the low power beam emitted from the HIFU transducer will be reflected. Such reflections are detected, and if the amount of reflected energy is greater than a threshold value, specific steps will be taken to dislodge the air bubbles. In a third embodiment, an imaging probe is used to image the therapy probe/tissue interface. Any air bubbles that are present in this interface will show up as a bright spot in the ultrasound image. If such bright spots are identified, proper steps are taken to dislodge the air bubbles. Techniques for dislodging air bubbles include repositioning the therapy probe to dislodge the air bubbles, inflating or deflating the liquid-filled membrane to dislodge the air bubbles, and flushing the interface with an irrigation liquid to dislodge the air bubbles.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1A (prior art) schematically illustrates an ultrasonic image generated during the simultaneous use of ultrasound for imaging and for providing HIFU therapy in a conventional manner, wherein noise due to the HIFU beam obscures the entire image;

FIG. 1B schematically illustrates an ultrasonic image generated during the simultaneous use of ultrasound for imaging and therapy, wherein pulsing of the HIFU limits the resulting noise to a portion of the image;

FIG. 1C schematically illustrates an ultrasonic image generated during the simultaneous use of ultrasound for imaging and therapy, wherein synchronized pulsing of the HIFU is used to shift the noise caused by the HIFU beam away from a treatment site displayed in the image;

FIG. 3A (prior art) is a schematic view of a distal end of the conventional vaginal probe of FIG. 2;

FIG. 3B is a HIFU module configured to be placed over the distal end of the conventional vaginal probe of FIGS. 2 and 3A;

Figure 1A:
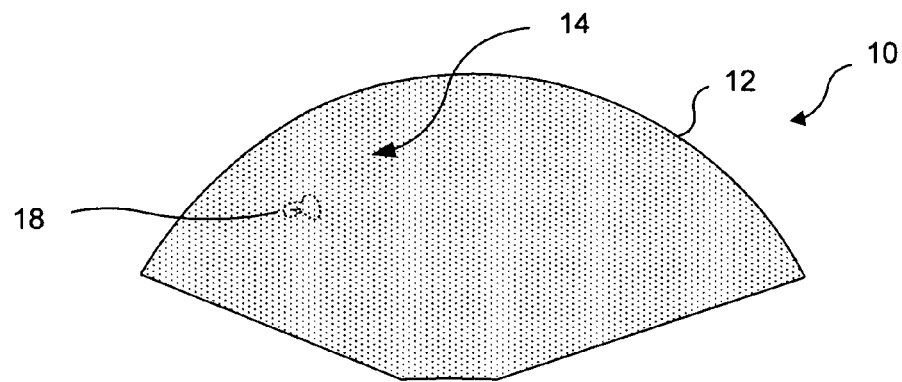
Figure 1B:
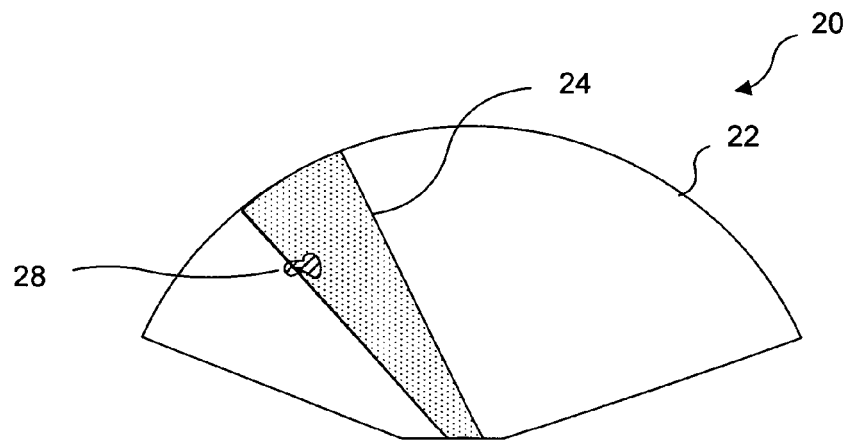
Figure 7A:
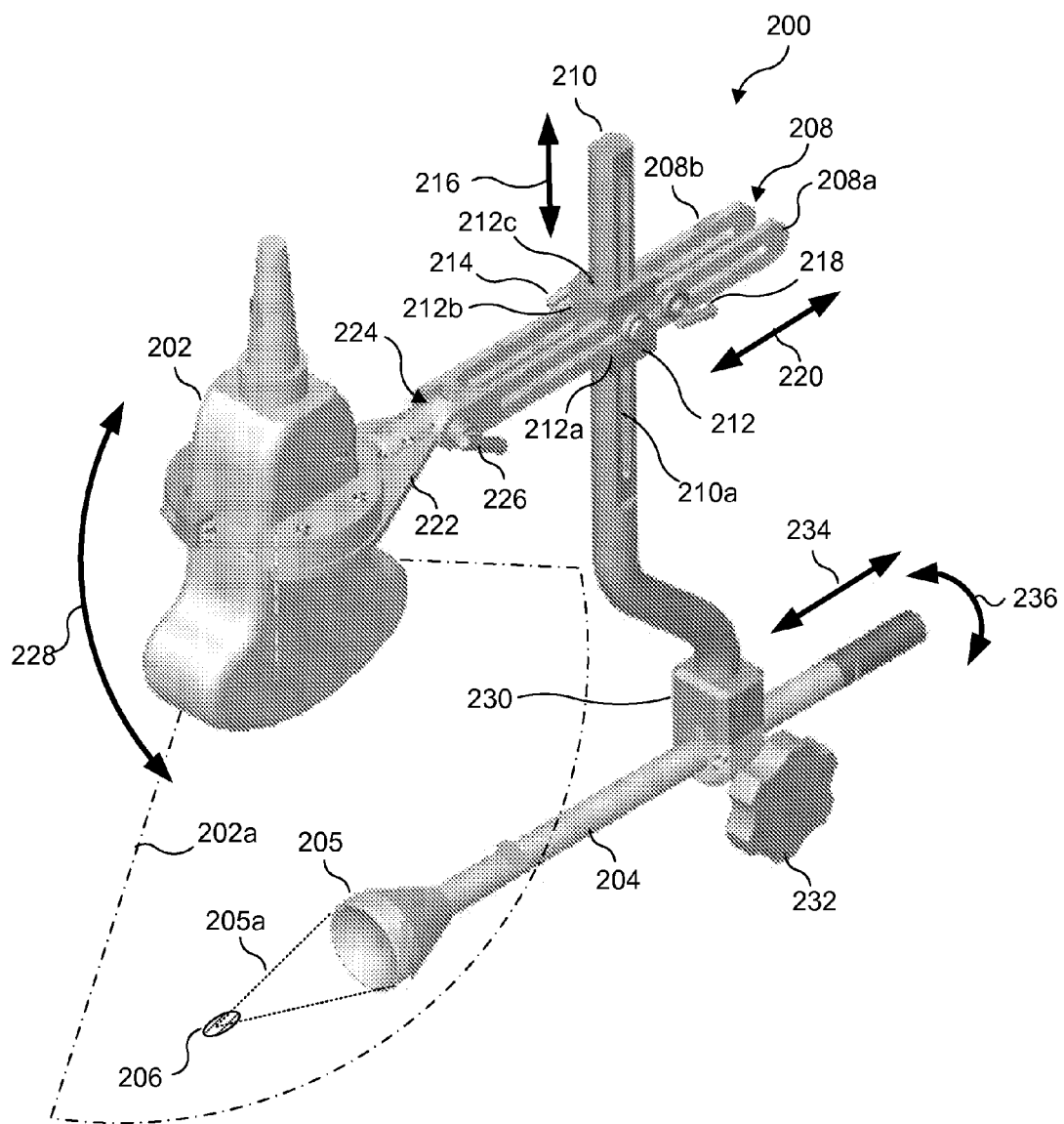
Figure 7B:
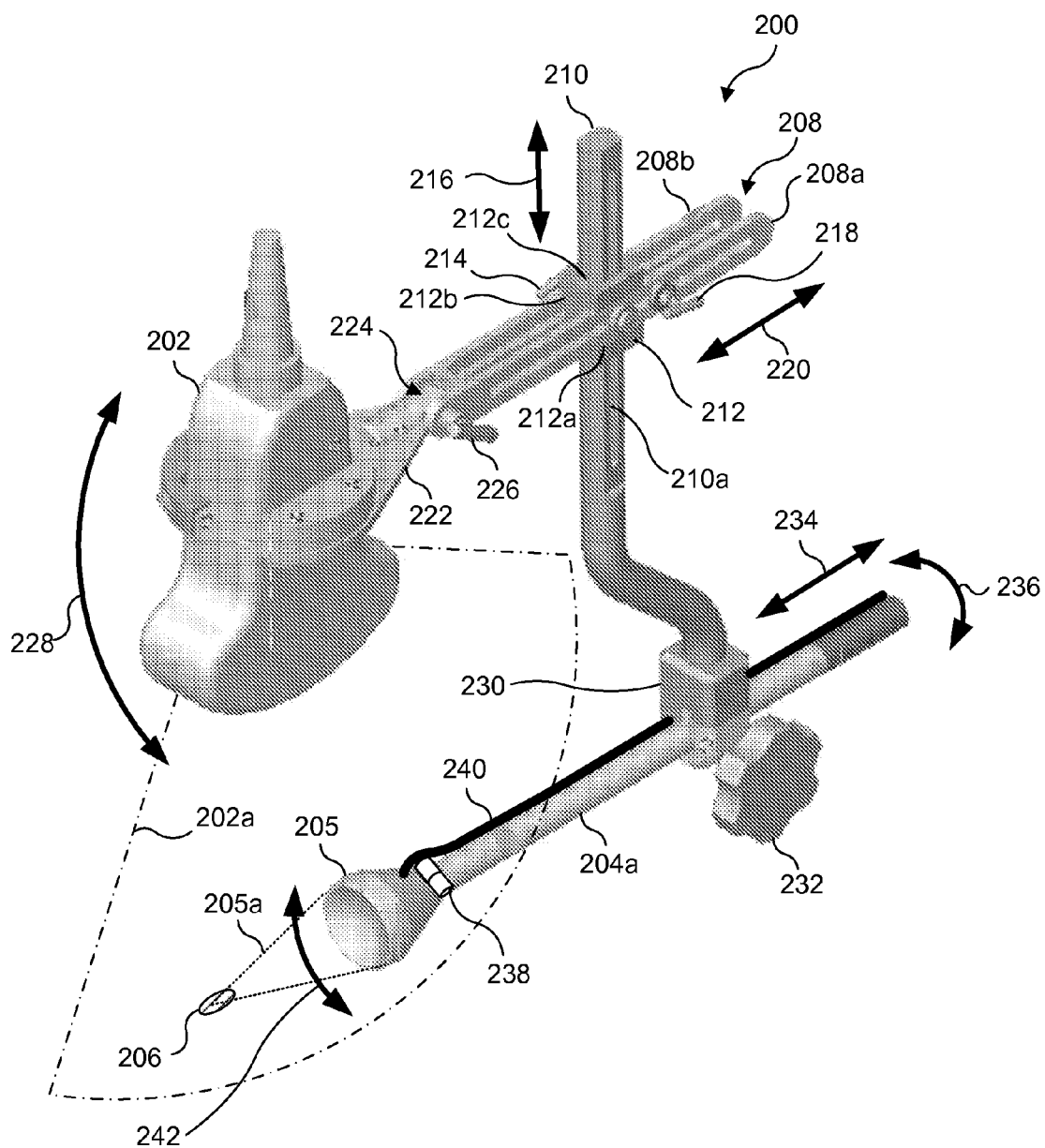
Figure 8:
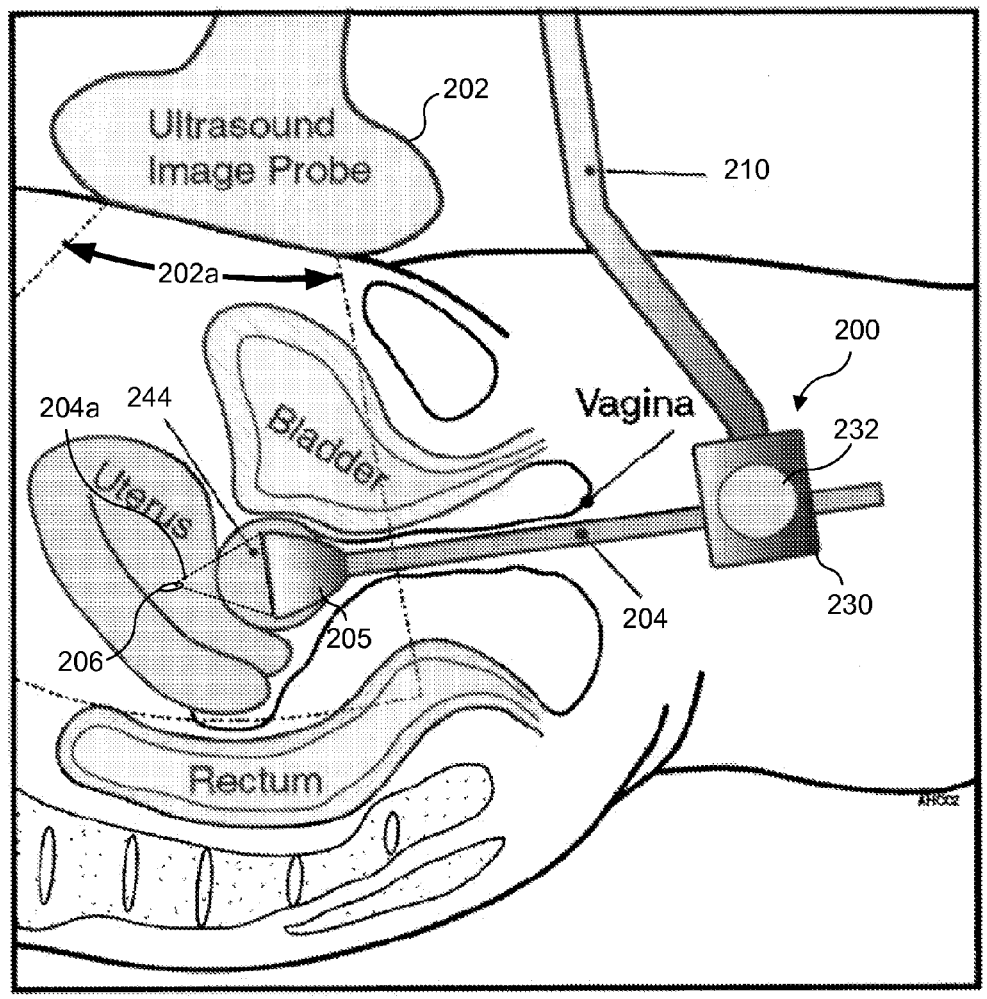
Figure 9:
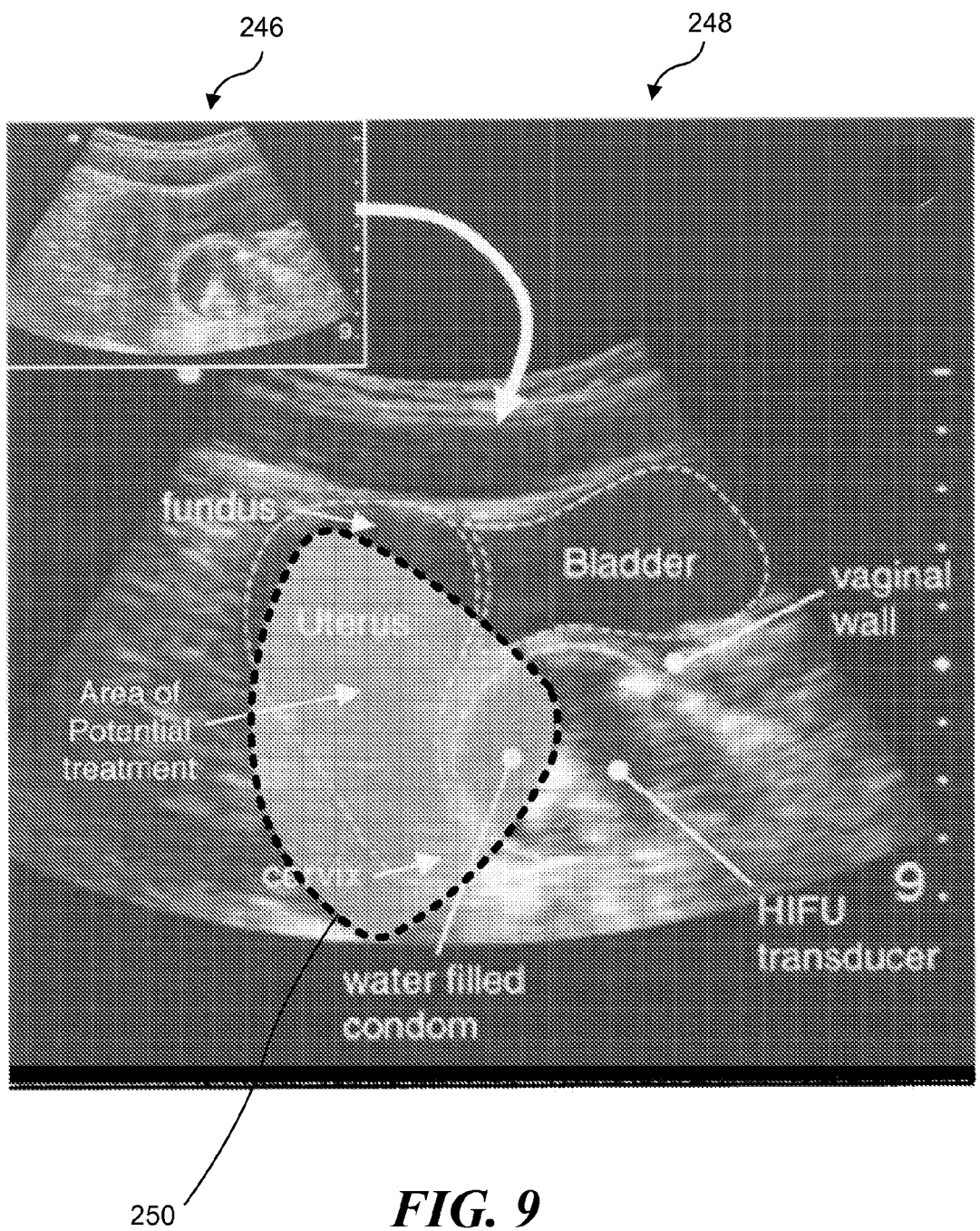
Figure 10:
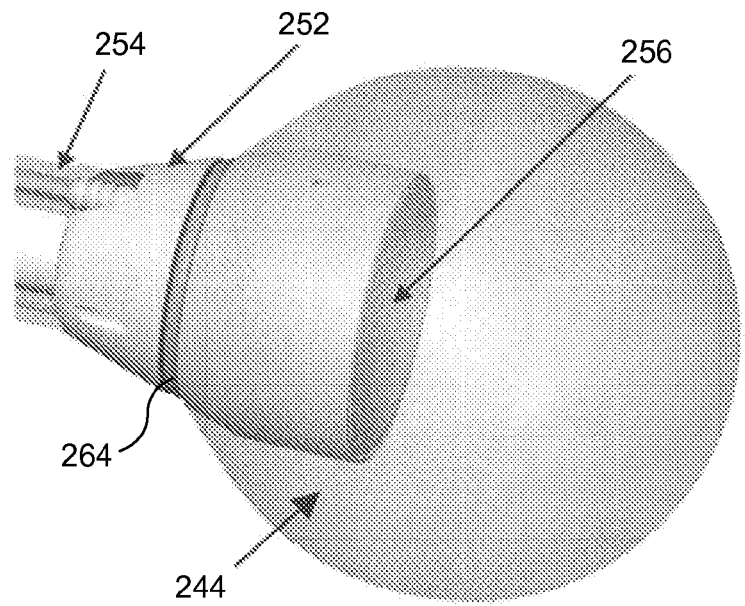
Figure 11:
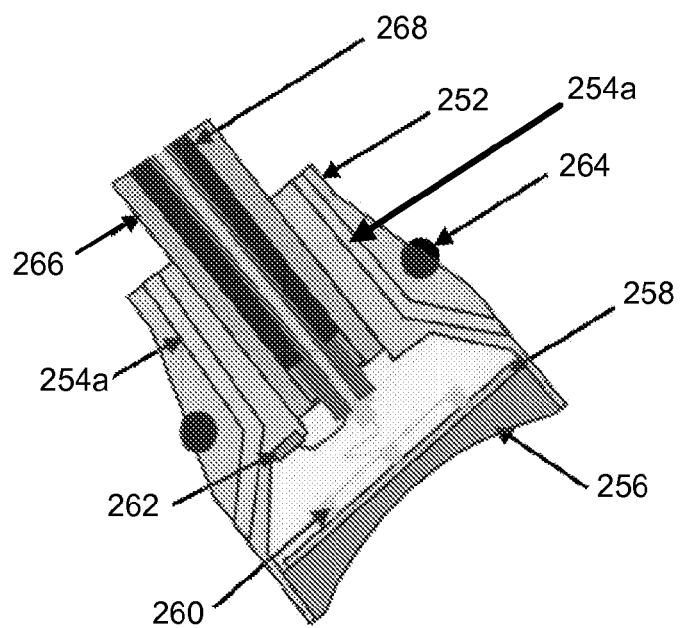
Figure 13A:
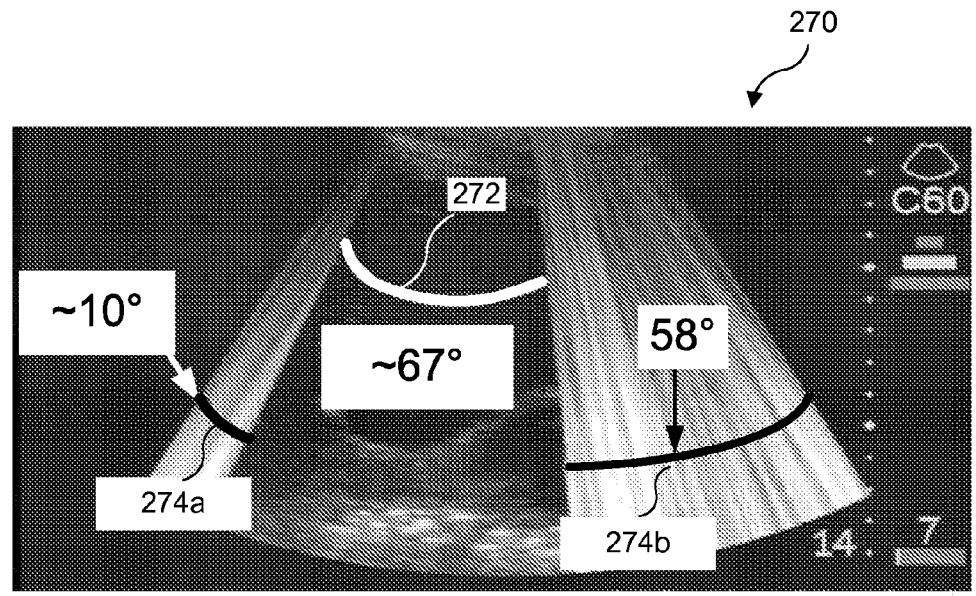
Figure 13B:
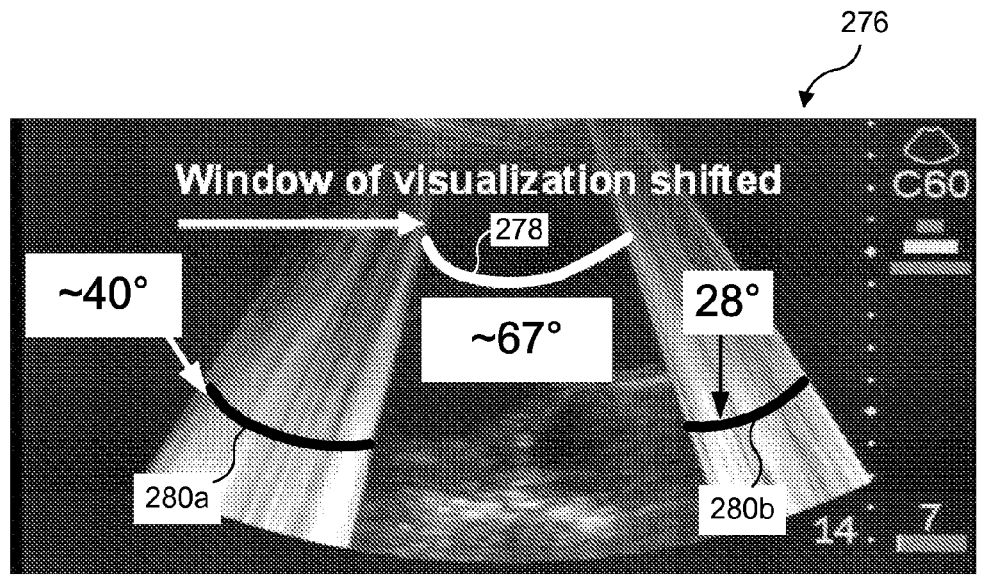
Figure 14:
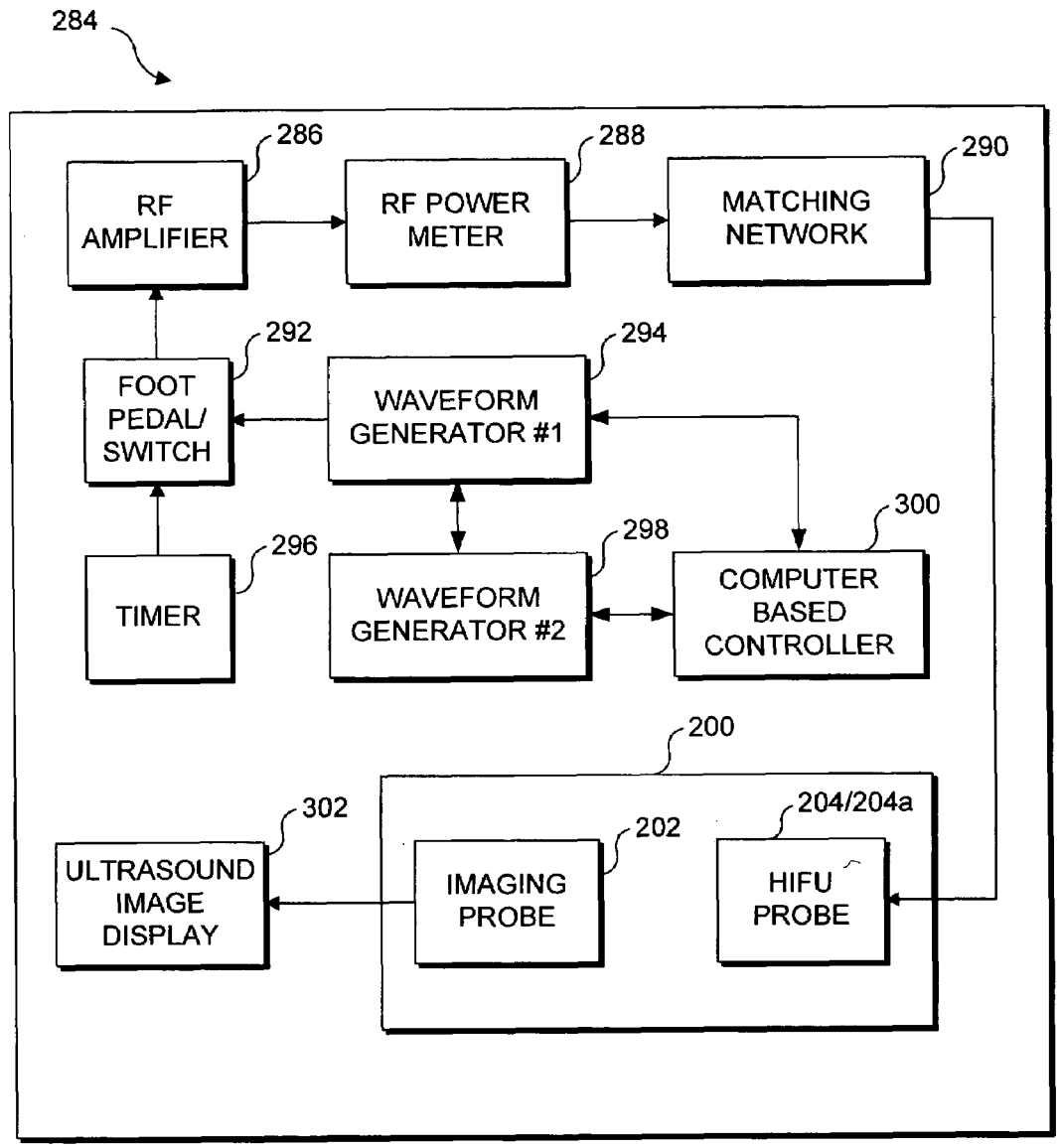
Figure 15A:
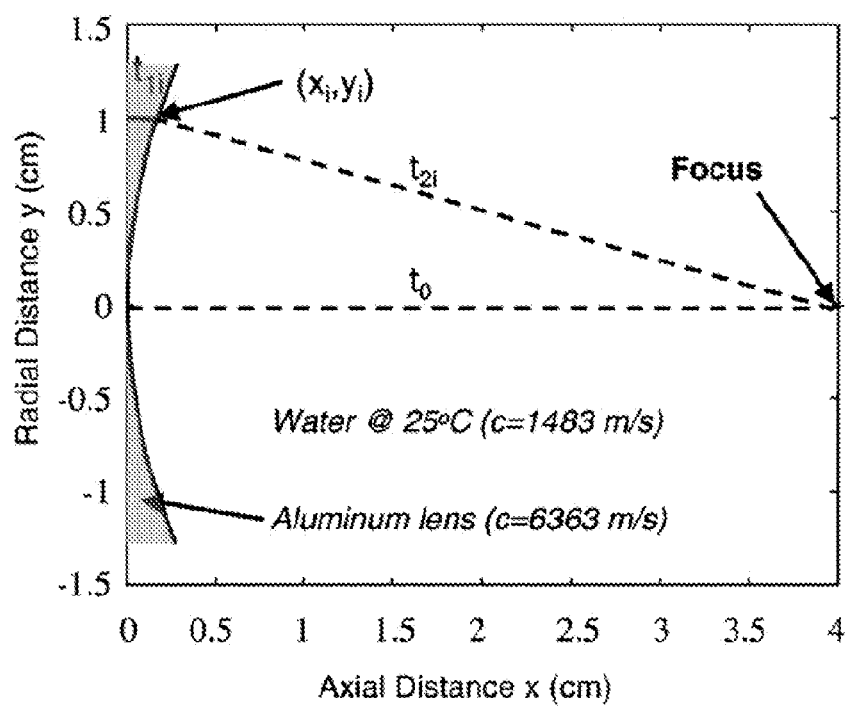
Figure 15B:
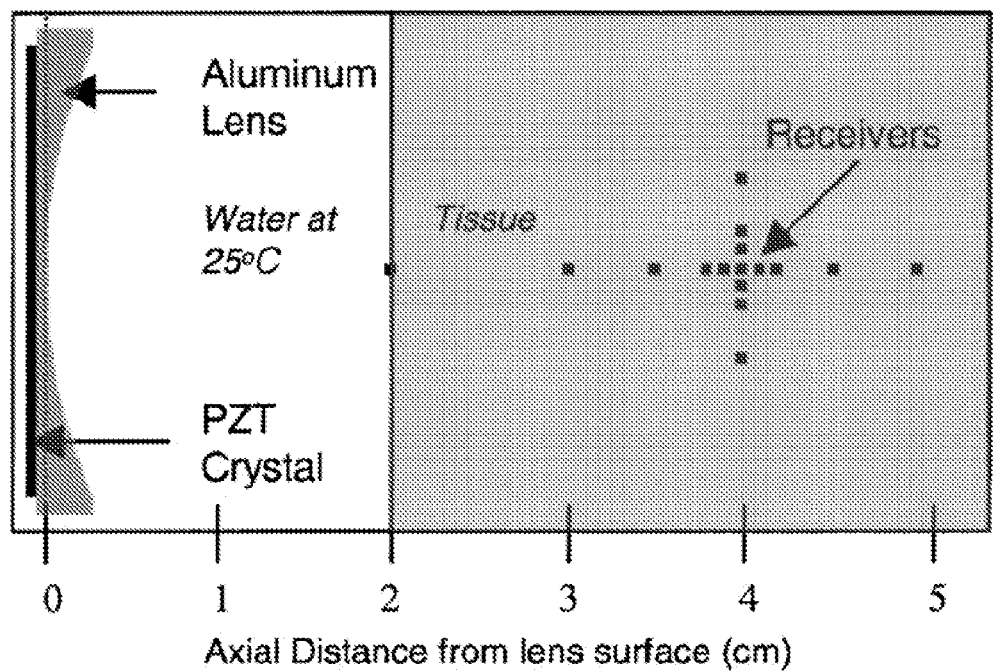
Figure 16A:
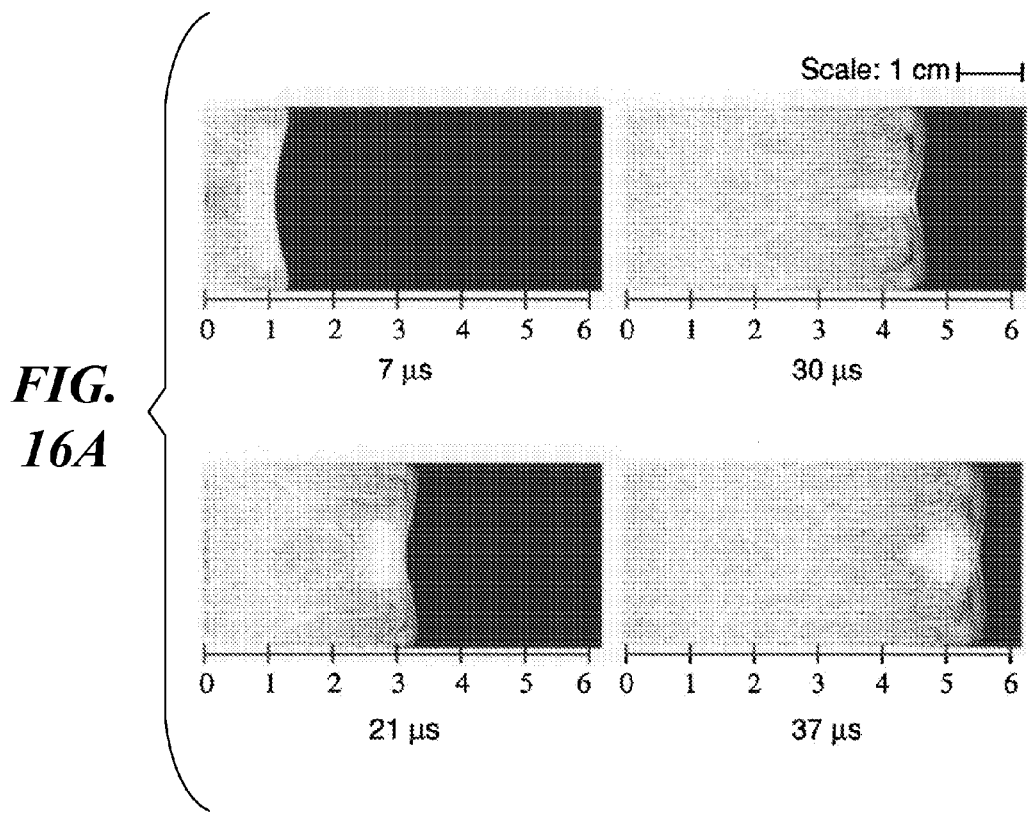
Figure 16B:
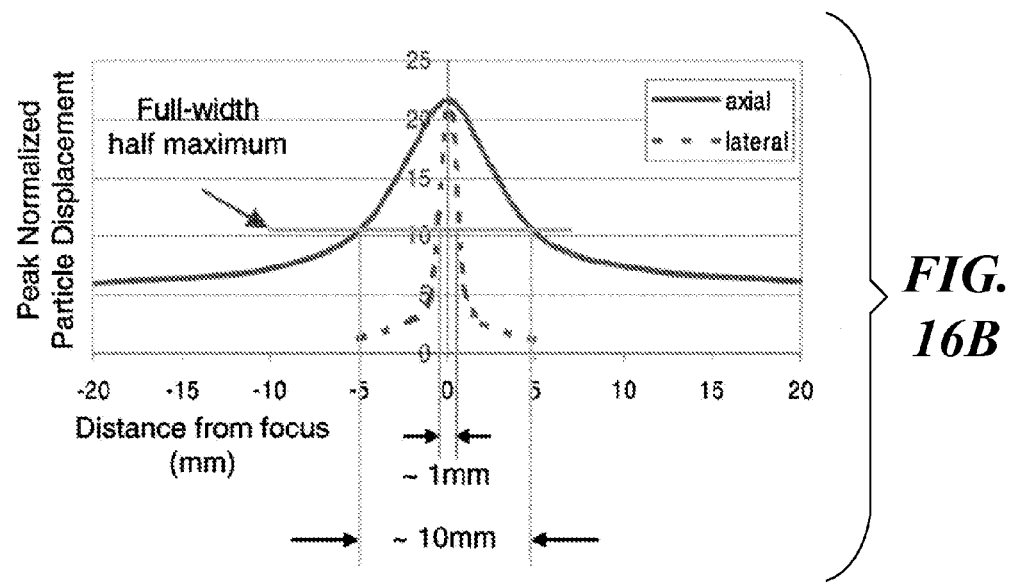
Figure 17A:
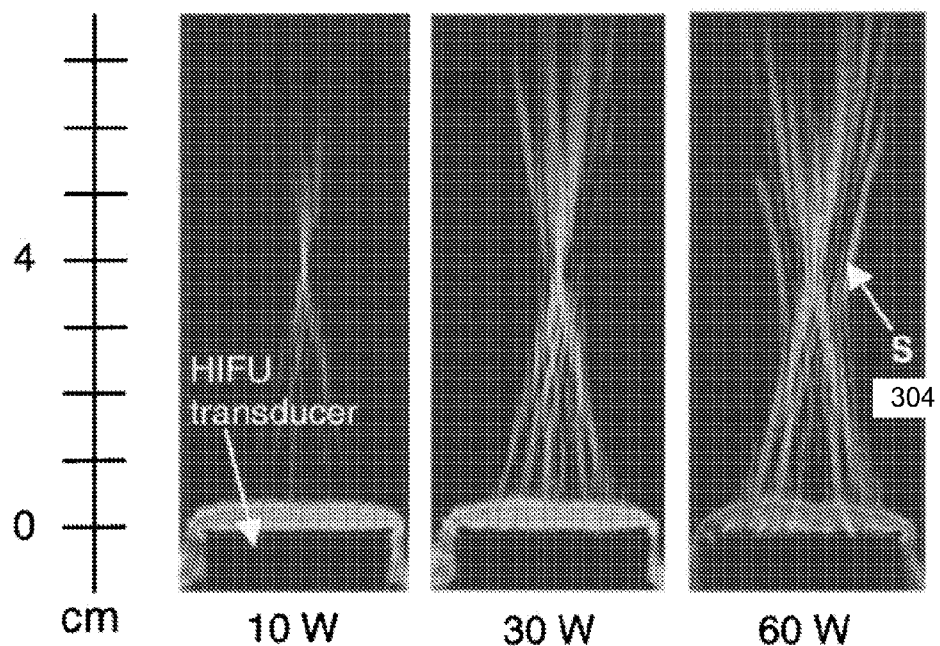
Figure 17B:
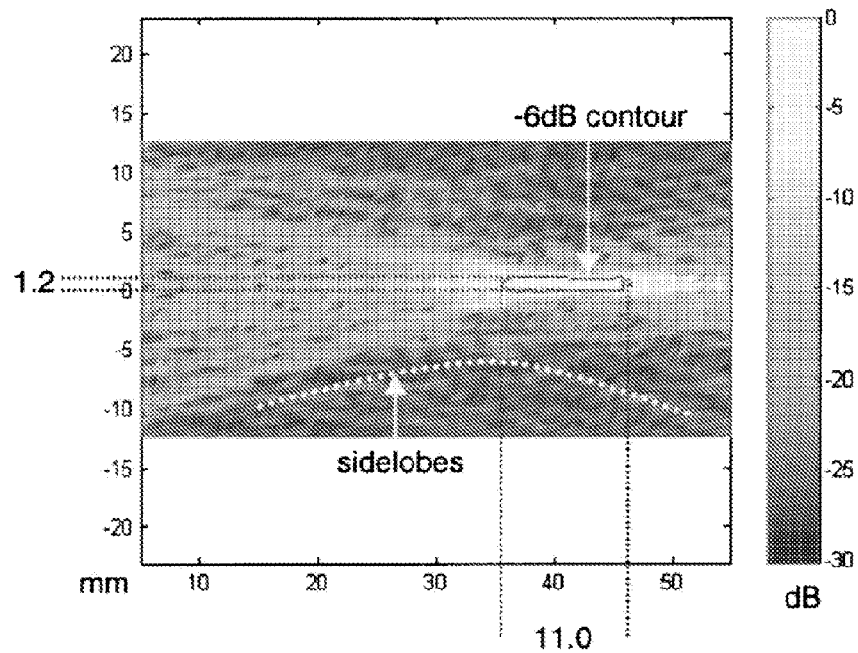
Figure 18:
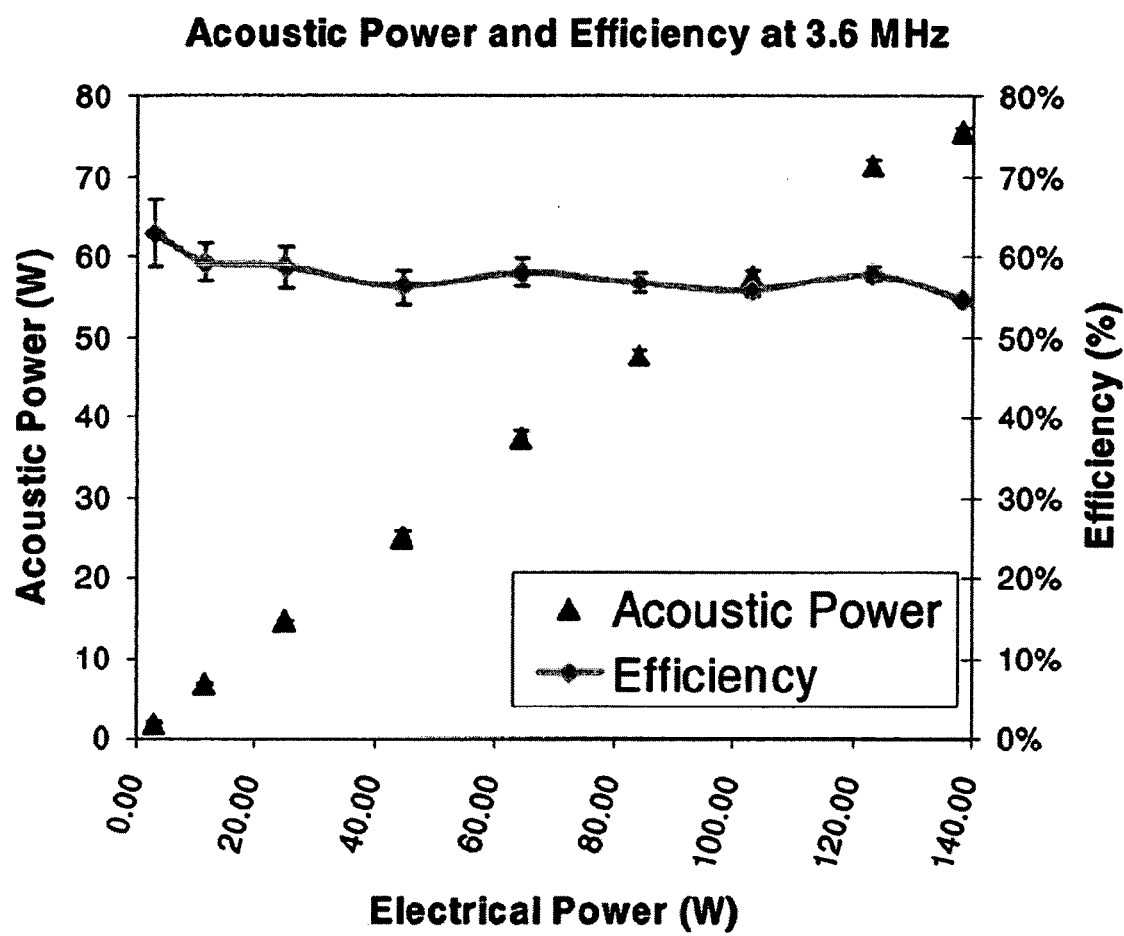
Figures 19A, 19B:
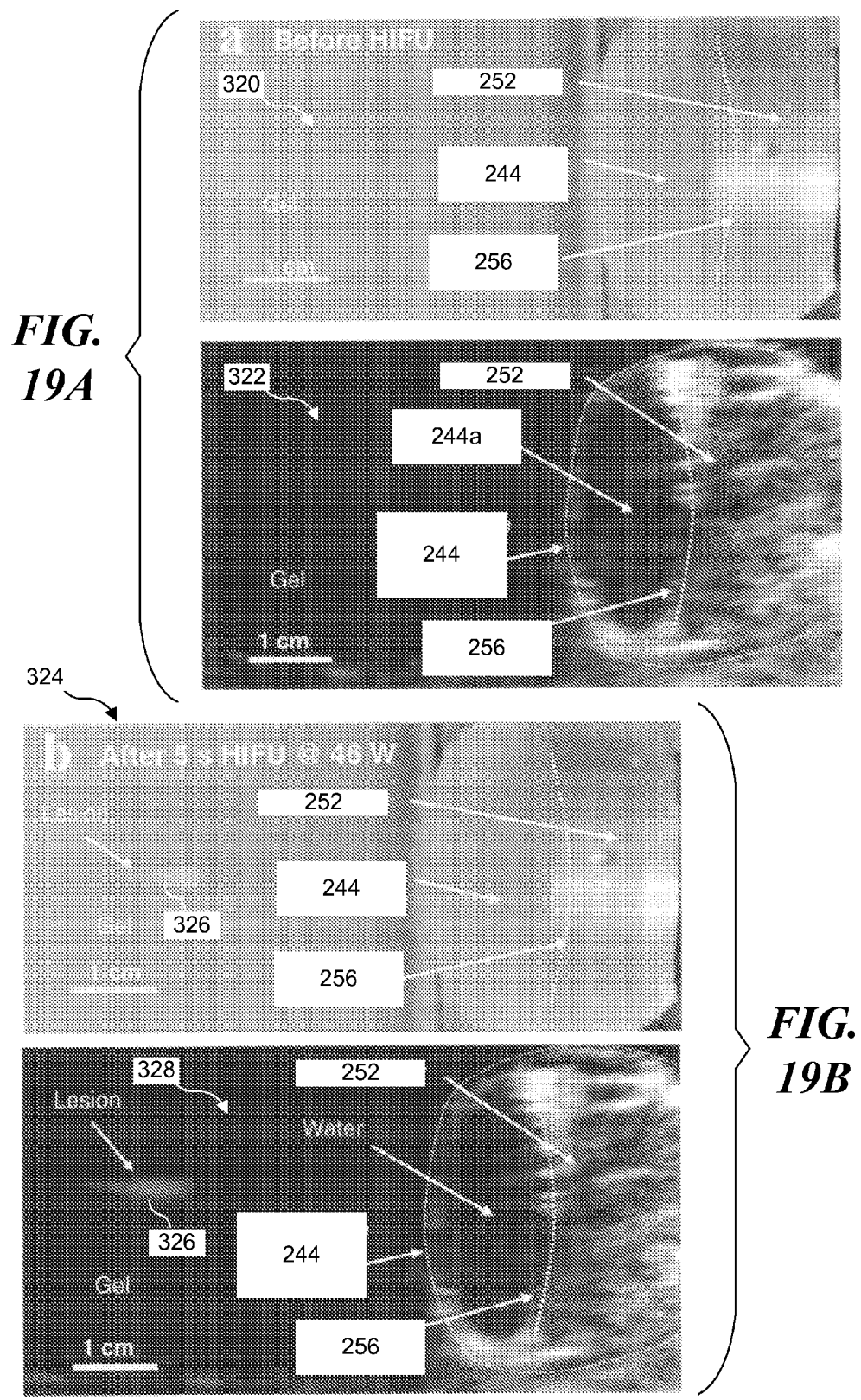
Figure 20A:
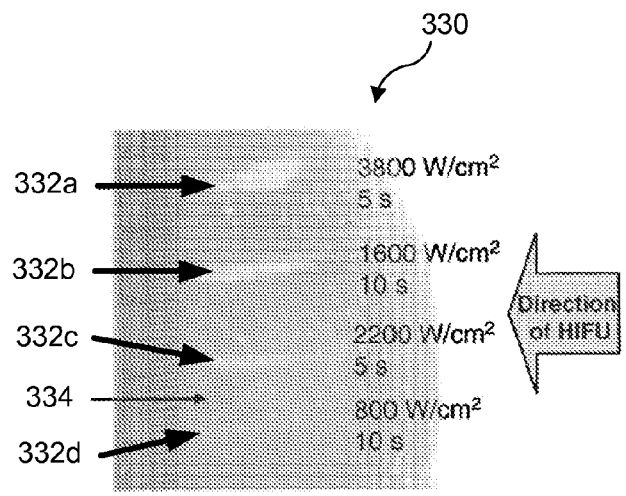
Figure 20B:
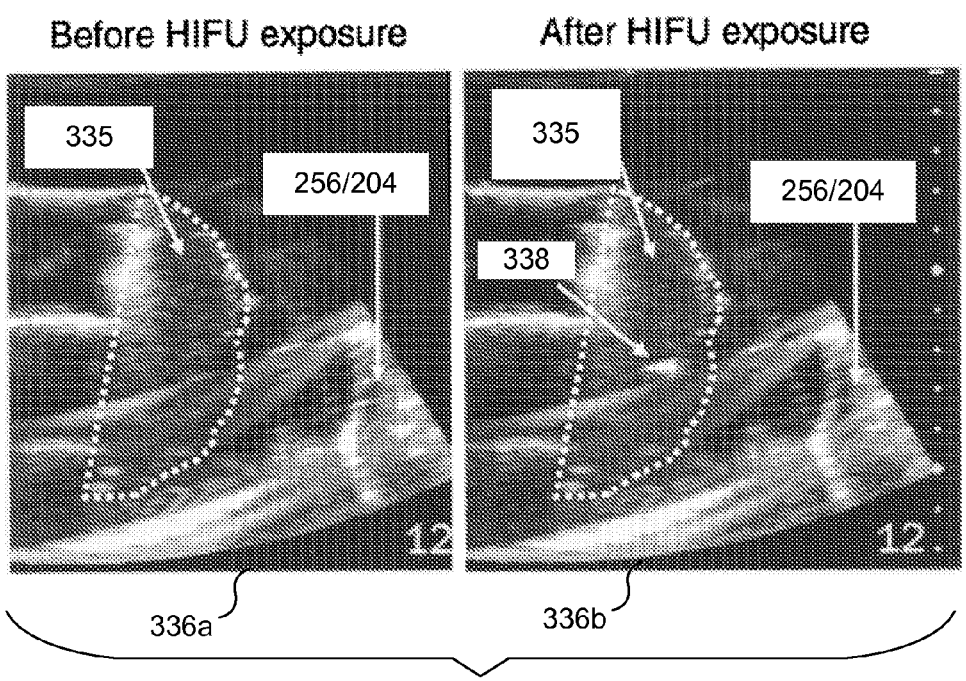
Figure 21A:
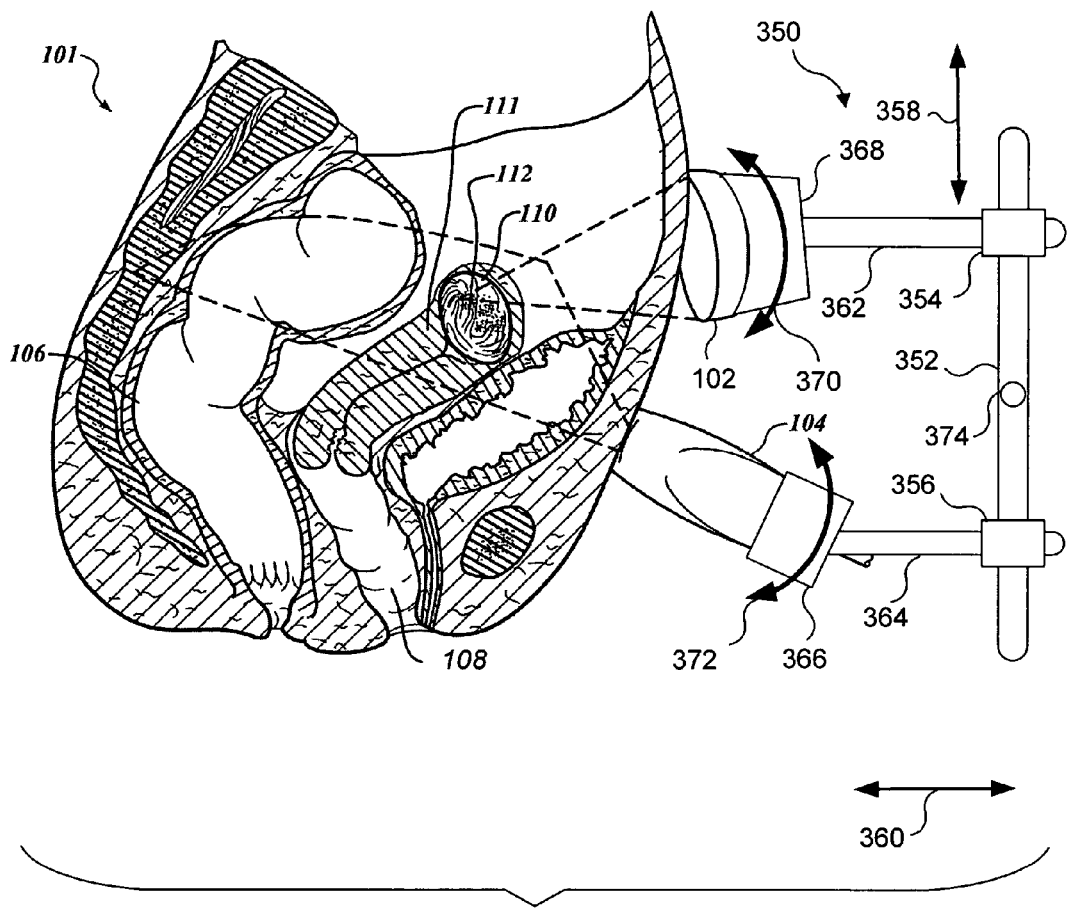
Figure 21B:
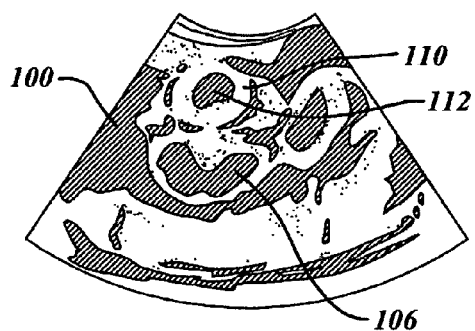
Figure 22:
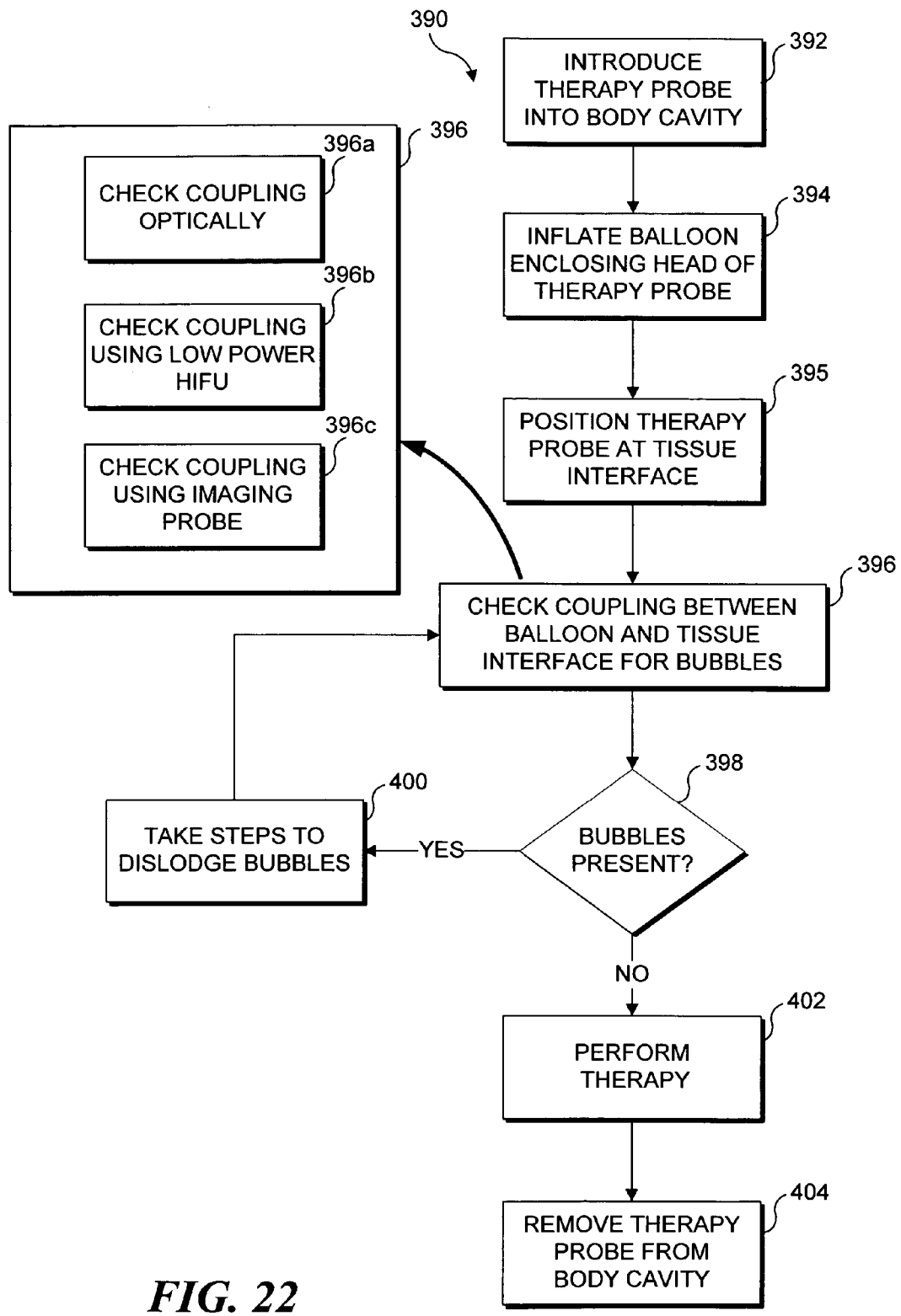
Figure 23A:
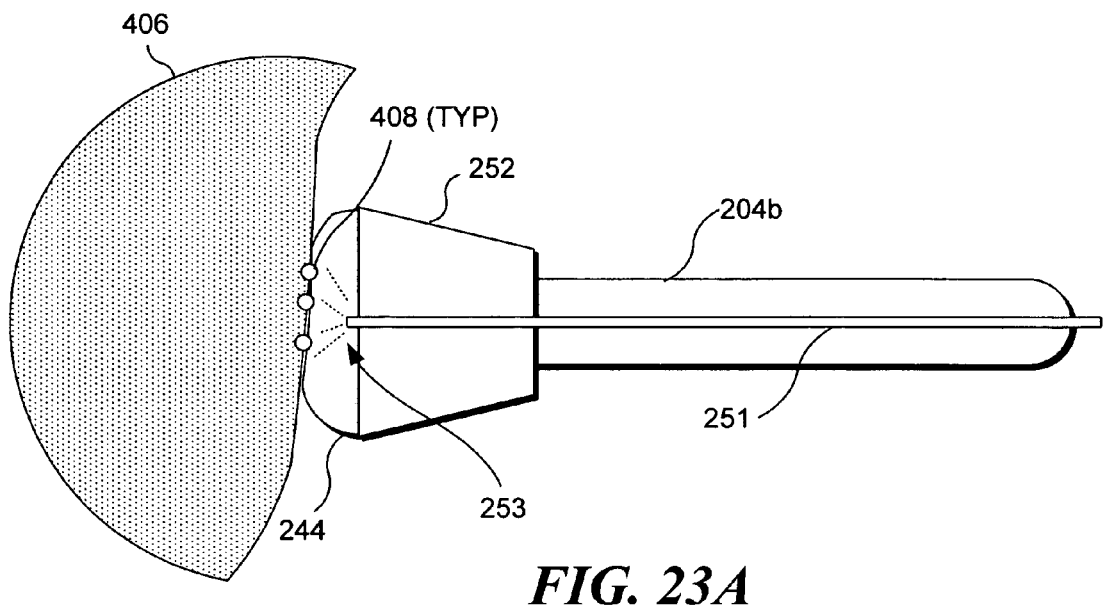
Figure 23B:
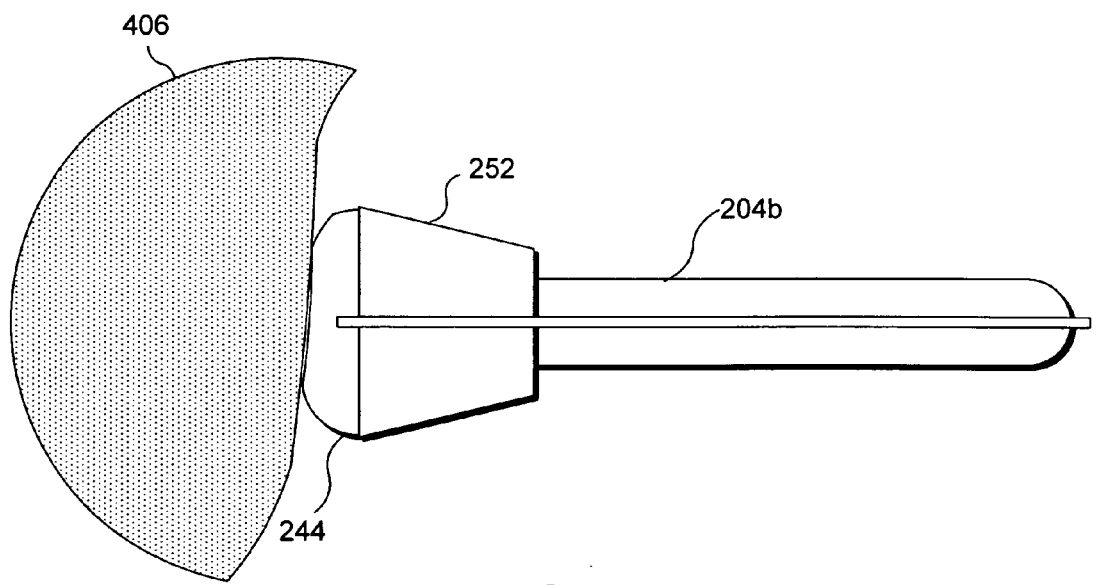
Figure 24:
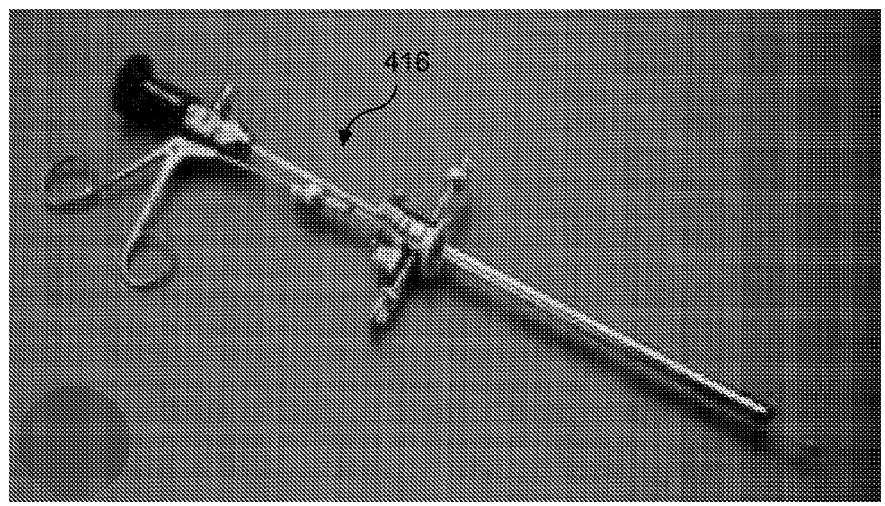
Figure 25A:
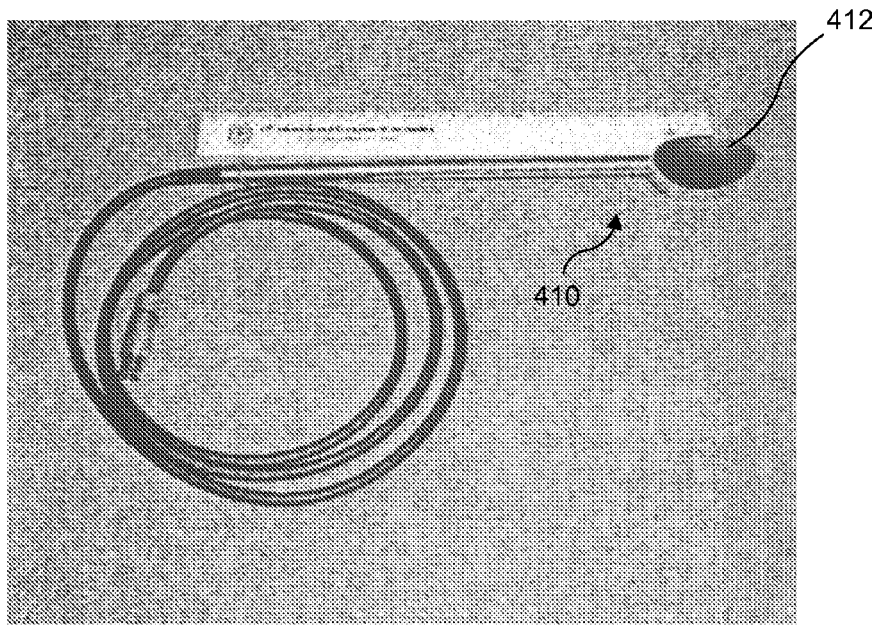
Figure 25B:
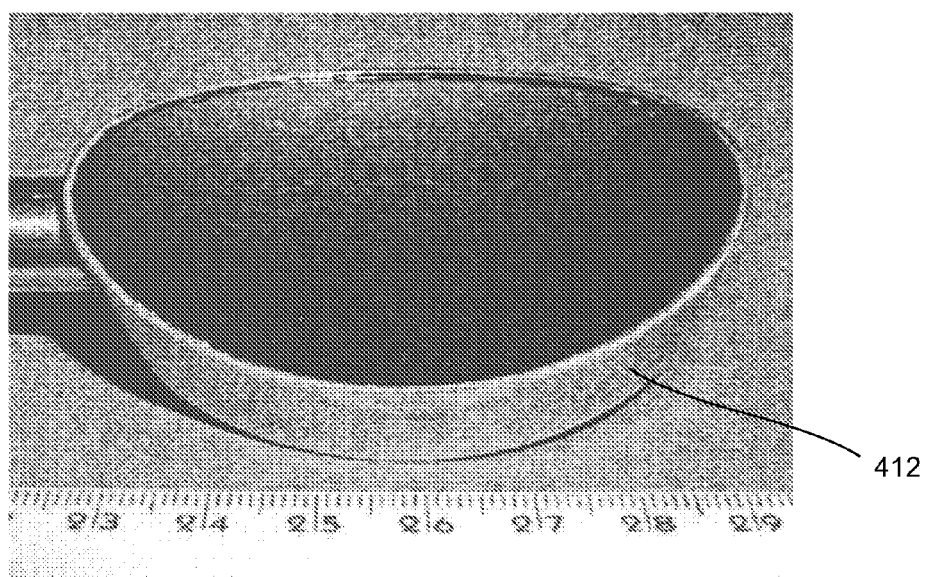
Figure 25C:
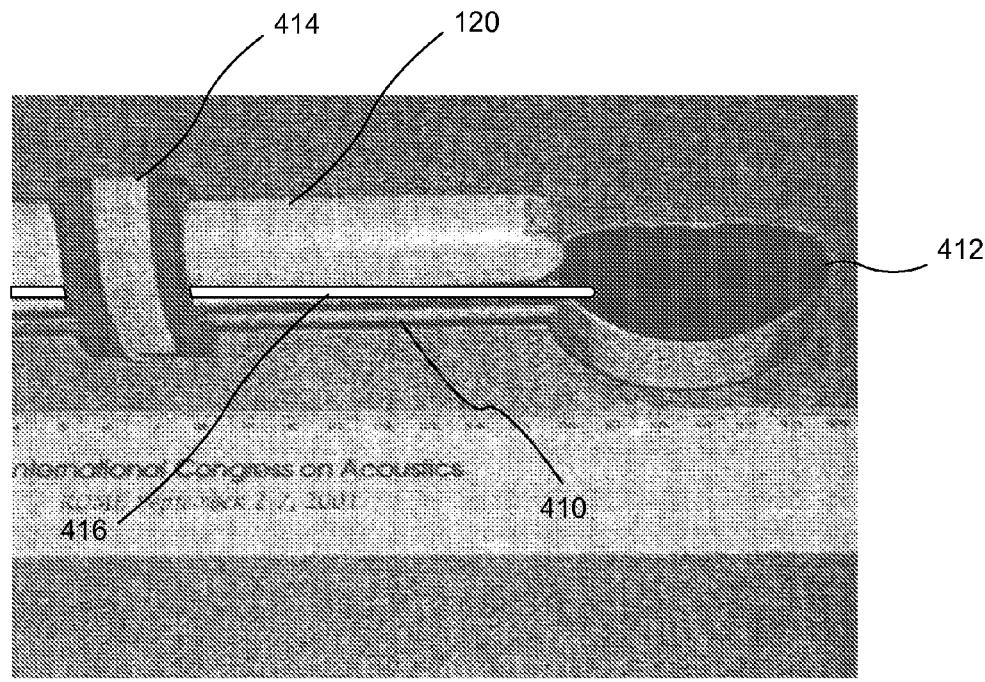
Figure 25D:
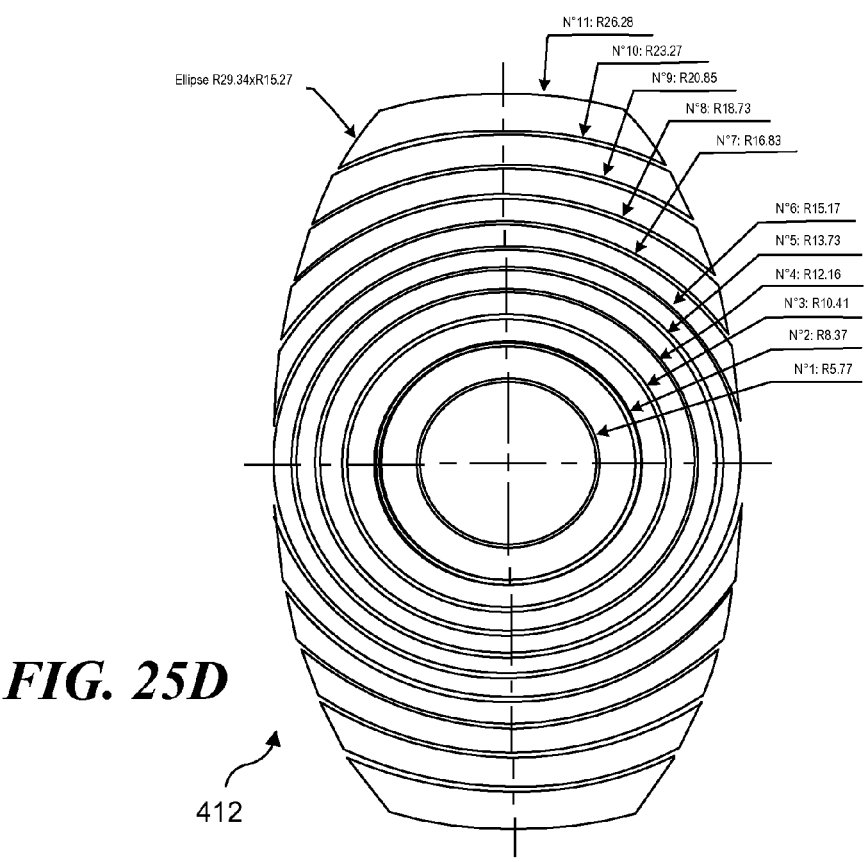
Figure 26:
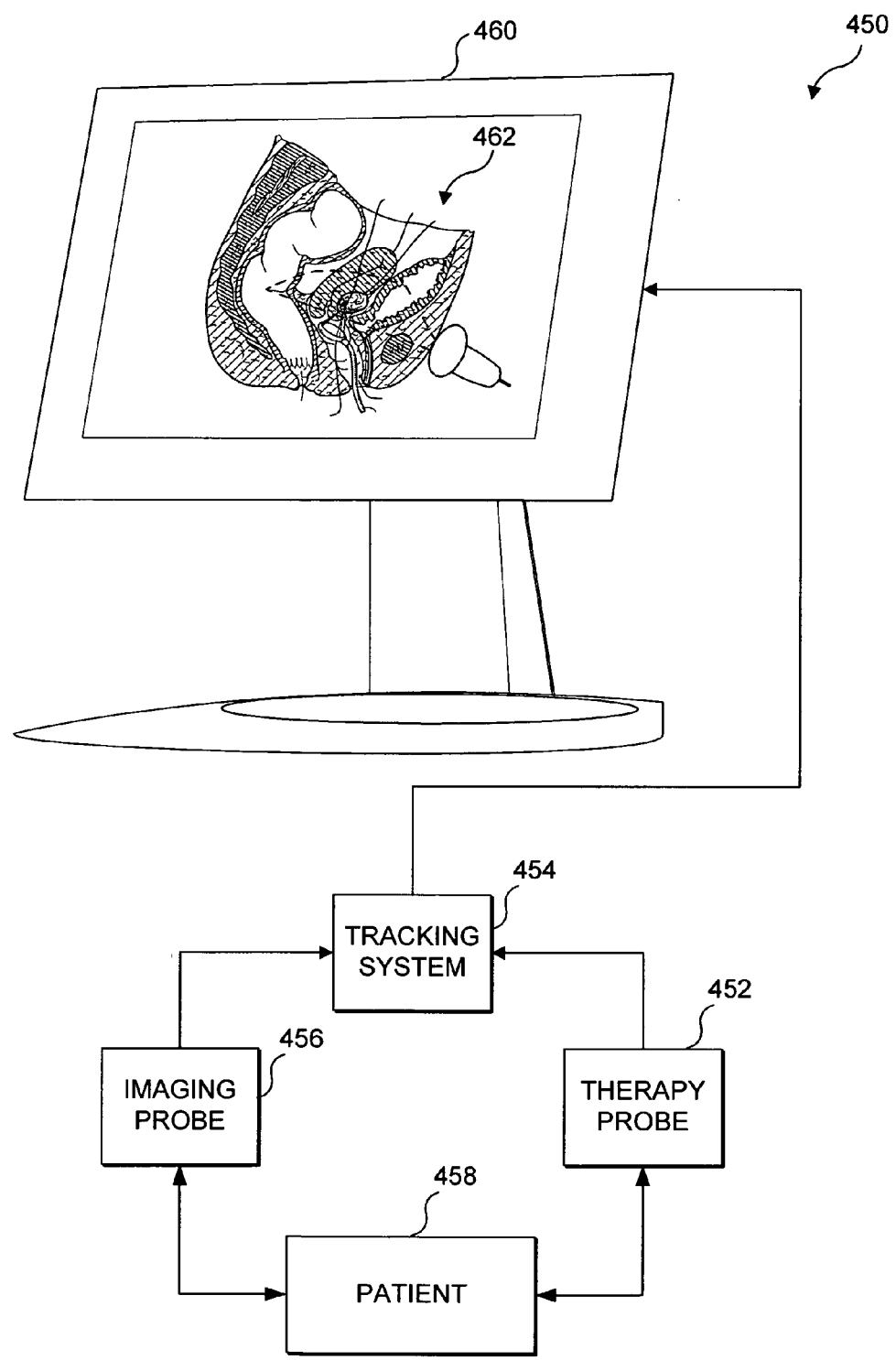
Figure 27:
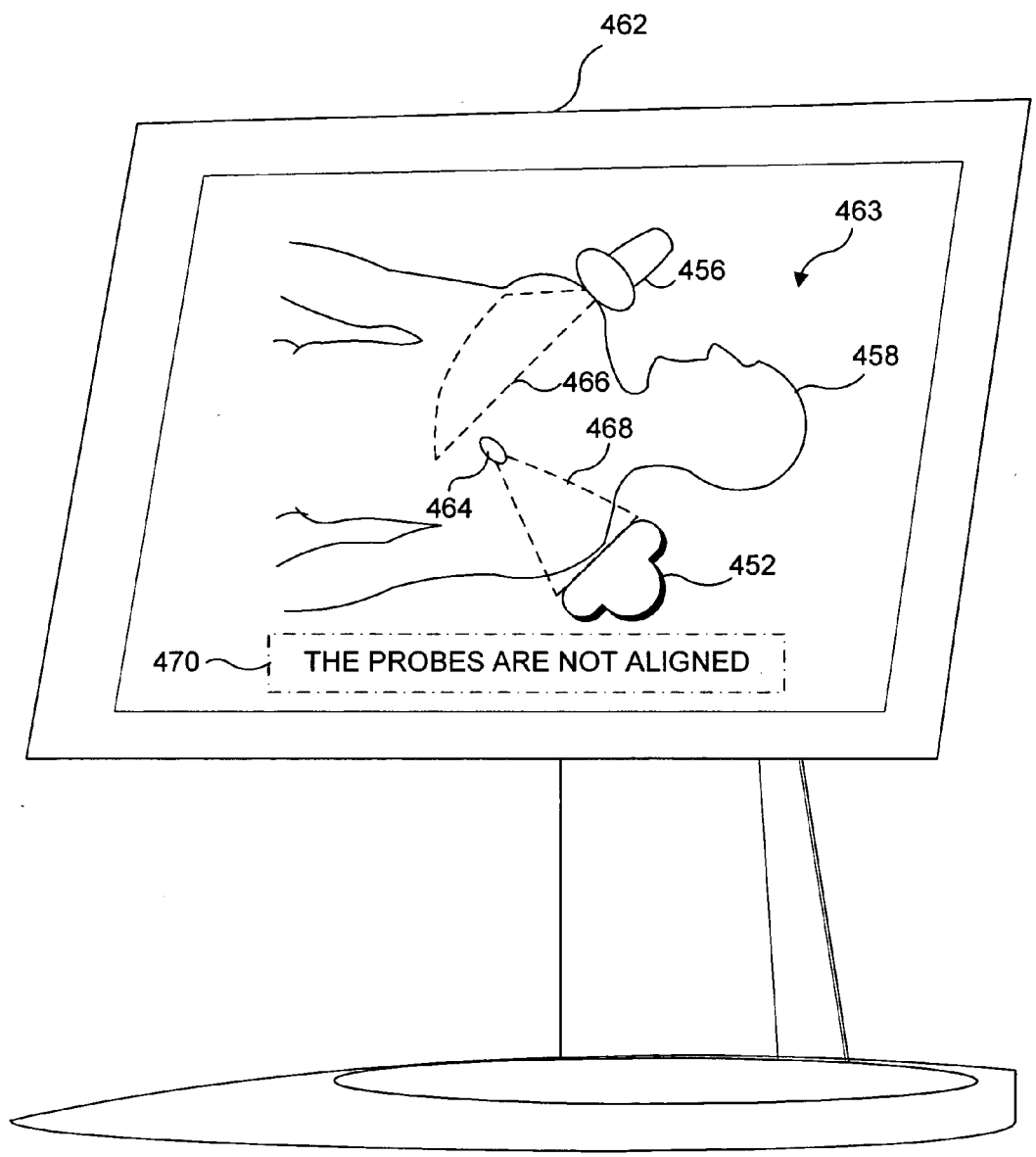

FIG. 7A schematically illustrates a frame that simultaneously supports a transabdominal imaging probe and a transvaginal HIFU therapy probe, in accord with the present invention;

FIG. 7B schematically illustrates the frame of FIG. 1B supporting a transvaginal HIFU therapy probe including a pivotable therapy head;

FIG. 8 schematically illustrates the frame, transabdominal imaging probe and transvaginal HIFU therapy probe of FIG. 7A properly positioned relative to a patient;

FIG. 9 is an exemplary ultrasound image produced by the transvaginal HIFU therapy probe of FIG. 7A positioned as indicated in FIG. 8;

FIG. 10 schematically illustrates a distal end of the transvaginal HIFU therapy probe of FIG. 7A;

FIG. 11 schematically illustrates an internal view of part of the distal end of the transvaginal HIFU therapy probe of FIG. 7A;

FIGS. 12A-12F illustrate elements used to assemble a working embodiment of the transvaginal HIFU therapy probe of FIG. 7A;

FIGS. 13A and 13B are ultrasound images illustrating how noise generated by the HIFU beam can be shifted to a portion of the ultrasound image that avoids interference with a visualization of the focal point of the HIFU beam during therapy;

FIG. 14 is a block diagram schematically illustrating the elements of a system for use with the present invention to facilitate visualization of the focal point of a HIFU beam during therapy;

FIGS. 15A and 15B graphically illustrate preferred geometries of the HIFU transducer and lens employed in the transvaginal HIFU therapy probe of FIG. 7A;

FIG. 16A is a composite of images extracted from a computer simulation used to design the HIFU transducer for use in the transvaginal therapy probe of FIG. 7A;

FIG. 16B graphically illustrates peak normalized particle displacements collected from the computer simulation used to design the HIFU transducer for use in the transvaginal therapy probe of FIG. 7A, indicating estimated focal dimensions of 10 mm in length by 1 mm in width;

FIG. 17A is a composite of Schlieren images obtained during empirical testing of the HIFU transducer used in the transvaginal therapy probe of FIG. 7A;

FIG. 17B graphically illustrates an acoustic field map created using data collected with a PVDF needle hydrophone during empirical testing of the HIFU transducer designed for use in the transvaginal therapy probe of FIG. 7A, indicating focal point dimensions of 11 mm in length and 1.2 mm in width;

FIG. 18 graphically illustrates the correlation between electrical power and acoustic power for the HIFU transducer used in the transvaginal therapy probe of FIG. 7A;

FIG. 19A is a composite image including both a photograph of the distal end of the transvaginal therapy probe of FIG. 7A coupled to a gel phantom and an ultrasound image of the distal end of transvaginal therapy probe of FIG. 7A coupled to the gel phantom;

FIG. 19B is a composite image including both a photograph and ultrasound image, substantially similar to those of FIG. 19A, after the application of HIFU therapy, wherein a lesion is visible in both the photograph and the ultrasound image;

FIG. 20A is a photograph of a turkey breast including a plurality of lesions formed using a HIFU beam generated with the transvaginal probe of FIG. 7A;

FIG. 20B is a composite image including before and after ultrasound images showing the transvaginal probe of FIG. 7A being positioned to apply HIFU therapy to a turkey breast, wherein a lesion is visible in the after image;

FIG. 21A schematically illustrates a second embodiment of a frame configured to maintain a spatial orientation between an imaging probe and a therapy probe during administration of HIFU therapy;

FIG. 21B schematically illustrates an ultrasound image generated by the imaging transducer shown in FIG. 21A;

FIG. 22 is a flowchart illustrating the logical steps implemented in a method for determining whether any air bubbles are present at an interface between a therapy probe and a mass of tissue, in accord with another aspect of the present invention;

FIG. 23A schematically illustrates the transvaginal therapy probe of FIG. 7A being coupled to a mass of tissue, so that a plurality of air bubbles are trapped at the tissue interface;

FIG. 23B schematically illustrates the transvaginal therapy probe of FIG. 7A being coupled to a mass of tissue, such that no air bubbles are trapped at the tissue interface;

FIG. 24 is a photograph of a prior art hysteroscope that is useful to optically determine whether any air bubbles are present at the tissue interface;

FIG. 25A is a photograph of a second embodiment of a transvaginal therapy probe in accord with the present invention;

FIG. 25B is a photograph of the generally spooned shaped transducer of the transvaginal therapy probe shown in FIG. 25A;

FIG. 25C is a photograph of the transvaginal therapy probe of FIG. 25A removably coupled to a prior art imaging probe, with the prior art hysterscope superimposed over the photograph, indicating how each instrument is used during a therapeutic procedure;

FIG. 25D schematically illustrates a plurality of emitter elements comprising the HIFU transducer in the transvaginal therapy probe of FIG. 25A; and FIG. 26 is a block diagram schematically illustrating the elements of a system for use with the present invention to facilitate free hand visualization of the focal point of a HIFU beam during therapy; and FIG. 27 schematically illustrates an exemplary image provided by the system of FIG. 26, enabling a clinician to determine how to manipulate a spatial relationship between an imaging probe and a therapy probe to ensure visualization of the focal point of a HIFU beam during therapy.

DESCRIPTION OF THE PREFERRED EMBODIMENT

The terms "therapeutic transducer," "HIFU transducer," and "high intensity transducer," as used herein and in the claims that follow all refer to a transducer that is capable of being energized to produce ultrasonic waves that are much more energetic than the ultrasonic pulses produced by an imaging transducer, and which can be focused or directed onto a discrete location, such as a treatment site in a target area. However, in at least one embodiment of the present invention, not all ultrasonic waves produced by such a transducer are necessarily at a high intensity, as is explained below.

When administering HIFU therapy, it is very desirable to be able to observe a treatment site, to ensure that lesions induced by the HIFU therapy are being produced at the desired location. Failure to properly aim the HIFU beam will result in undesired tissue necrosis of non target tissue. From a practical standpoint, this goal has not proven easy to accomplish when ultrasound is used to visualize the focal point, because the HIFU beam used for therapy completely saturates the signal provided by the imaging transducer. One analogy that might help to make this problem clear relates to the relative intensities of light. Consider the light coming from a star in the evening sky to be equivalent to the low power imaging ultrasound waves that are reflected from a target area toward the imaging transducer, while the light from the sun is equivalent to the HIFU generated by the therapy transducer. When the sun is out, the light from the stars is completely overwhelmed by the light from the sun, and a person looking into the sky is unable to see any stars, because the bright light from the sun makes the dim light coming from the stars substantially imperceptible. Similarly, the HIFU emitted by the therapy transducer completely overwhelms the ultrasonic waves produced by the imaging transducer, and any ultrasonic image generated is completely saturated with noise caused by the HIFU emitted from the therapeutic transducer.

FIG. 1A illustrates an ultrasound image 10 in which a scanned image field 12 is completely obscured by noise 14, as is typical during the simultaneous reception of energy from a reflected imaging pulse and a HIFU wave (neither shown). In regard to ultrasound image 10, a clinician may desire to focus the HIFU wave on a treatment site 18. However, because noise 14 completely saturates scanned image field 12, it is virtually impossible to accurately focus the HIFU wave onto treatment site 18. If the therapy transducer is completely de-energized, noise 14 is eliminated from the scanned image field. However, under these conditions, the focal point of the HIFU wave will not be seen, and thus, the HIFU wave cannot be accurately focused on treatment site 18. While some change in echogenicity at the HIFU focal point will persist for a time after the HIFU wave is no longer present, any change in a position of the therapy transducer (or treatment site 18) will not register until the therapeutic transducer is re-energized, and thus, the HIFU wave cannot be focused in real time.

Some prior art systems have included a targeting icon in an ultrasound image to indicate the position of the known focal point of a specific HIFU transducer in a scanned image. While this icon may be helpful in determining whether the HIFU was previously focused, it still does not enable a clinician to observe real-time results. Once the HIFU therapeutic transducer is energized, the scanned ultrasound image is completely saturated with noise, and the clinician cannot monitor the progress of the treatment without again de-energizing the HIFU therapeutic transducer.

FIG. 1B illustrates one technique in which the effect of noise disrupting the ultrasound image is reduced. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging ultrasound pulses generated by the scanning transducer. In FIG. 1B, noise 24 substantially masks a treatment site 28. This result will not occur in all cases, because to an observer, noise 24 will move across scanned filed 22 as the interference between the HIFU waves and the imaging pulses varies in time. Pulsing of the HIFU wave alone can thus enable the clinician to view a noise-free image of the treatment site only when noise 24 is randomly shifted to a different part of scanned field 22, away from the treatment site. However, this pulsing of the HIFU beam generates an image that is extremely distracting to a clinician, as noise 24 flickers across scanned field 22, making it difficult to concentrate and difficult to consistently determine where the focal point of the HIFU wave is relative to the treatment site, in real time.

Figure 1C:
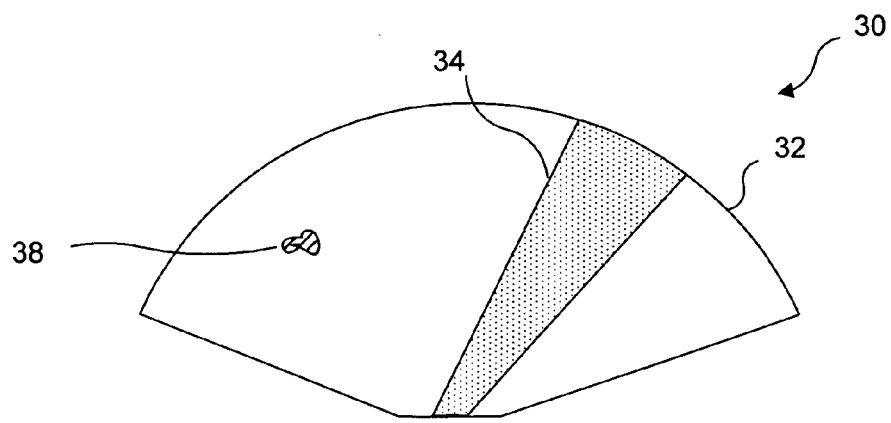

FIG. 1C illustrates an ultrasound image 30 in which a HIFU wave from a therapy transducer has been both pulsed and synchronized with respect to the ultrasonic imaging pulses from an imaging transducer, to ensure that noise 34 does not obscure a treatment site 38. In ultrasound image 30, noise 34 has been shifted to a location within a scanned field 32 of the image that is spaced apart from treatment site 38, by selectively adjusting both the pulsing and the synchronization of the HIFU wave relative to the image pulses. Preferably, noise 34 is shifted completely away from treatment site 38, enabling the clinician to view a noise-free, stable image of treatment site 38 that clearly shows the location of the focal point of the HIFU wave relative to the treatment site. Thus, the HIFU wave can be focused in real time onto treatment site 38, and a clinician can, in real time, view the therapeutic effects of the HIFU wave on treatment site 38. It will therefore be apparent that a clinician can de-energize the therapeutic transducer, terminating the generation of the HIFU wave as soon as a desired therapeutic effect has been achieved at the treatment site. In this manner, undesired effects on non target tissue can be minimized.

FIGS. 2-5 illustrate details of combination probes that can be used to simultaneously provide imaging and therapy for a treatment site. In such combination probes, the spatial relationship between the imaging transducer and the HIFU transducer is generally static, because both the scanning transducer and the HIFU transducer are combined in a single instrument. Movement of the probe will generally not move the focal point of the HIFU transducer out of the imaging plane of the scanning transducer, because both transducers are part of the combination probe. Some of the combination probes are based on prior art imaging probes to which a therapy head has been retrofitted, while other of the combination probes integrate the imaging and therapy transducers into a single device. As will be described in greater detail below, in some embodiments the therapy transducer can move a finite amount relative to the scanning transducer, however in such embodiments the range of movement for the therapy transducer is well defined, and preferably such movement will not result in the focal point of the therapy transducer moving out of the imaging plane provided by the imaging transducer.

Figure 2:
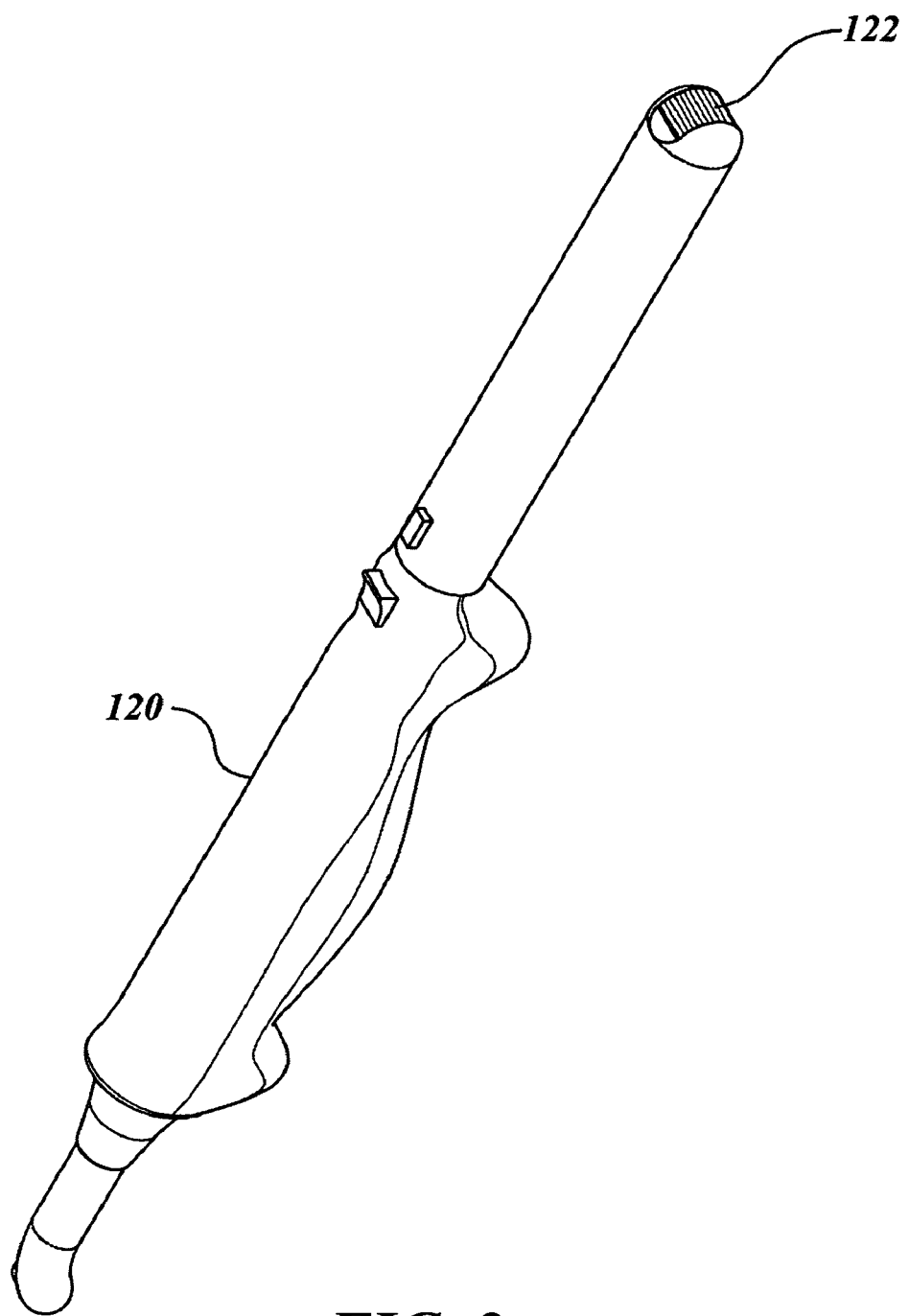
FIG. 2 (prior art) is a schematic view of a conventional vaginal probe that includes an imaging transducer.
Figure 3C:
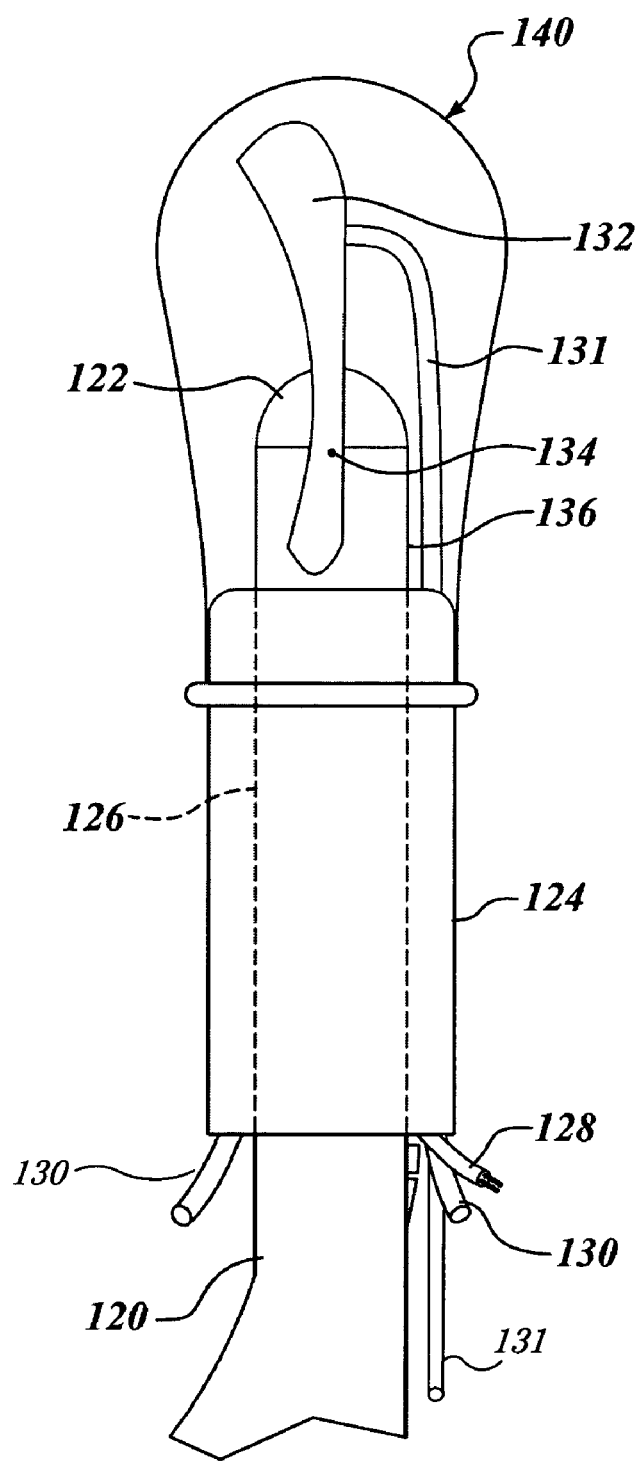
FIG. 3C is a schematic view of a HIFU module mounted onto the distal end of the conventional vaginal probe of FIGS. 2 and 3A.

For example, FIG. 2 illustrates a prior art ultrasonic vaginal imaging probe, which is a Model C9-5™ transvaginal imaging probe 120 available from Philips Medical Systems of Bothell, Wash. FIGS. 3A and 3B illustrate a HIFU module 123 mounted onto a distal end of prior art transvaginal imaging probe 120. Transvaginal imaging probe 120 includes an imaging transducer array 122. HIFU module 123 is sized and shaped to fit over the distal end of transvaginal imaging probe 120 and incorporates a cylindrical shaft 124 that has a cylindrical bore 126. Cylindrical bore 126 is sized to easily slide over the distal end of transvaginal imaging probe 120, and in its wall are disposed a plurality of fluid passages 130. Those of ordinary skill in the art will readily understand that ultrasonic waves do not readily pass through air gaps, and water or other liquid-filled balloons are often used to conduct an ultrasonic wave between the ultrasonic transducer from which it is transmitted and a target of interest. Fluid passages 130 are used to circulate degassed water through a balloon 140 (FIG. 3C) that surrounds HIFU module 123. It is important that the water be degassed, because bubbles within the water scatter and attenuate the ultrasonic waves. In addition to providing good coupling of the ultrasound waves into the adjacent tissue, the water circulating through the balloon provides cooling to the transducer elements that avoids an unwanted buildup of heat. It is currently common practice to use a condom for the balloon, although other inert and flexible elastomeric materials can be used instead.

In FIG. 3C, transvaginal imaging probe 120 has been inserted into cylindrical bore 126 of cylinder 124, and the imaging transducer array 122 is disposed within a void 138. Cylinder 124 also includes electrical leads 128, which connect the HIFU transducer to a power amplifier (not shown) that drives the HIFU transducer. Located atop cylinder 124 is a HIFU transducer mounting base 136. It should be noted that HIFU transducer mounting base 136 is also hollow, so that transvaginal imaging probe 120 may pass completely through the center of HIFU transducer mounting base 136, to position imaging transducer array 122 within void 138 (see FIG. 3B). This configuration enables imaging transducer array 122 to transmit an ultrasound imaging pulse to the target of interest.

As shown in FIG. 3C, HIFU therapy transducer 132 is pivotally mounted to HIFU transducer mounting base 136 at a pivot joint 134. This pivotal mounting arrangement enables a clinician to selectively target various treatment areas within the female reproductive system by rotating the HIFU transducer about pivot joint 134. The disposition of the HIFU transducer on pivot joint 134 can be adjusted prior to inserting the combination transvaginal imaging probe and HIFU module into the vaginal canal, or while the probe is in the vaginal cavity. The angle of the HIFU transducer should be adjusted based on the relative position of the target area and treatment site. Once in the vaginal canal, the combination transvaginal imaging probe and HIFU module can be moved to a position that enables an ultrasonic image of the target area to be observed on a display and then the position of the probe and module can be adjusted to focus the HIFU wave onto a desired treatment site within the target area.

A mechanical linkage 131 connected to HIFU transducer 132 enables the HIFU transducer to be selectively pivoted about pivot joint 134 while the combination transvaginal probe and HIFU module is in the vaginal canal. This capability provides a clinician greater flexibility in directing the HIFU transducer toward a particular treatment site. However, a skilled clinician can initially select an angle for the HIFU transducer relative to the longitudinal axis of the transvaginal imaging probe, insert the combination vaginal probe and HIFU module into the vaginal canal, and then manipulate the combination imaging probe and HIFU module while in the vaginal canal to acquire the image of the target area and focus the HIFU beam on the desired treatment site.

Figure 4A:
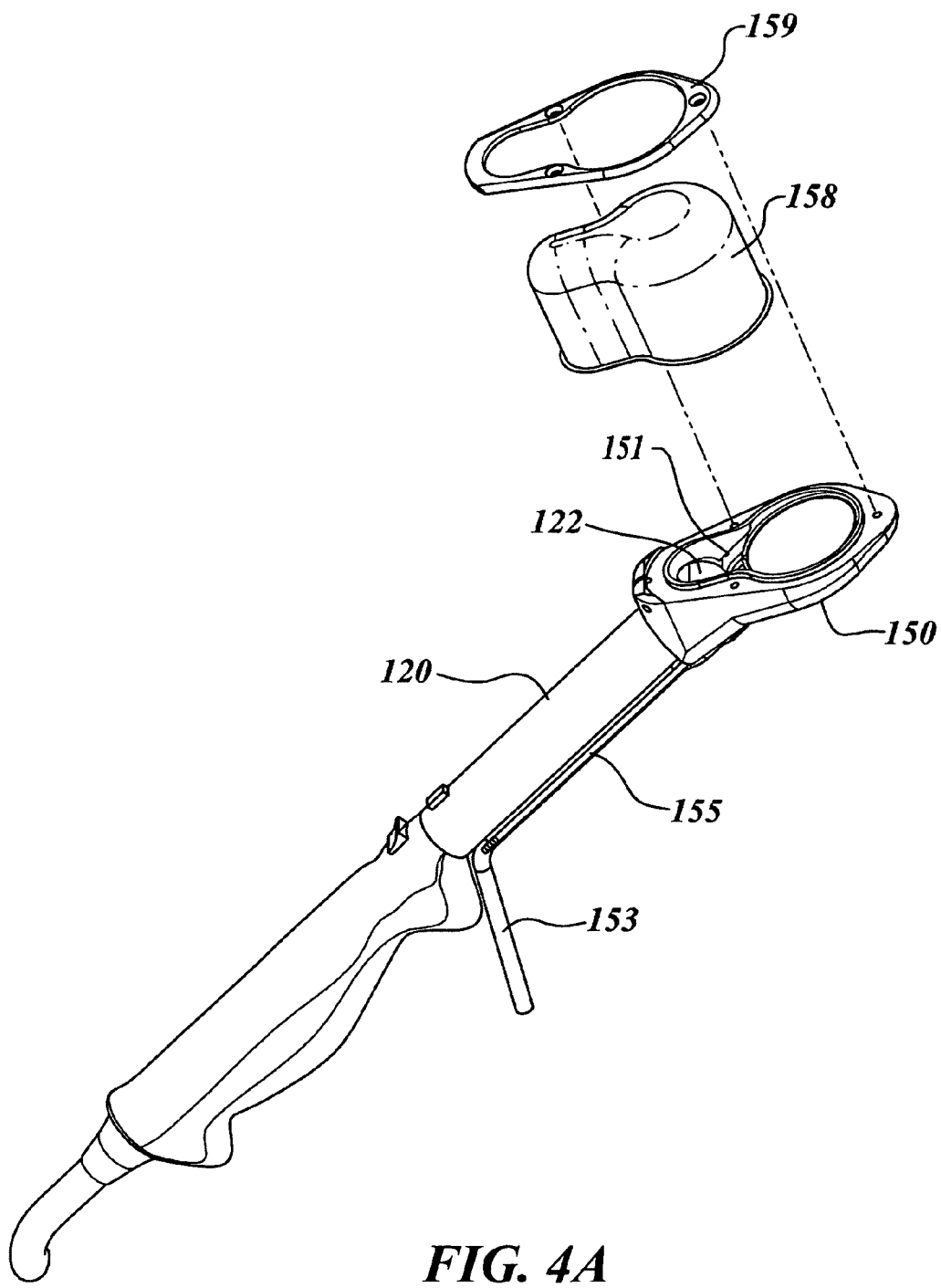
FIG. 4A is a schematic view of a second embodiment of a HIFU module and conventional vaginal probe.

FIG. 4A illustrates another embodiment of a combination imaging and therapy transducer based on the prior art transvaginal imaging probe. As shown in this Figure, a therapy transducer module 150 has been mounted onto transvaginal imaging probe 120. The design of the module is constrained by the anatomy involved in the transvaginal application of HIFU to treating uterine fibroids, as discussed above. Module 150 is mounted at the tip of the vaginal probe, and contains an opening through which the scan head (imaging transducer) transmits an ultrasound wave to obtain an image of the uterus, the fibroid, and any other structure of interest. The opening enables about one half of the scan head to transmit the imaging ultrasound wave. The other half is covered by the module assembly, does not have a window for imaging, and therefore, does not contribute to the image. In other words, half of the ultrasound image obtained by the vaginal probe in this configuration is masked by the assembly and is blank. The main housing of the module is made of a biocompatible, medical grade plastic, or other materials, such as metals. A chamber 158 can be filled with a liquid, such as degassed water, for the purpose of coupling the HIFU wave to adjacent tissue. A water circulation system is used to circulate degassed cold water through chamber 158, for both cooling of the HIFU transducer and to carry away any cavitation bubbles that may be generated during the HIFU excitation. The water conduits extend through the plastic housing and two holes disposed on opposite sides of a central passage (not shown). Stainless steel needle stock can be employed for tubes 155 that carry the water in and out of the chamber. Tubes 155 run along the shaft of the vaginal probe adjacent to a coaxial cable 153, which is employed for conveying the signal to energize the HIFU transducer. A cover 159 attaches the membrane, which forms chamber 158, to module 150. A HIFU transducer is disposed on a rim cut inside a brass bowl (details not shown) that is affixed with an appropriate adhesive to module 150. An electrical connection to the HIFU transducer is thus made through coaxial cable 153. Preferably, the HIFU transducer is a concave, fixed focused transducer, operating at a center frequency of about 2.0 MHz. The radius of curvature of this embodiment of the HIFU transducer is about 55 mm, and its aperture diameter is about 35 mm. The focus of the HIFU transducer is within the imaging plane of the imaging probe (preferably a Philips Medical Systems Model C9-5™ transvaginal probe). In fact, the imaging plane intersects the HIFU beam envelope (cone shaped) through its center, placing both the focus and the HIFU beam longitudinal axis in the imaging plane, as can be seen in FIG. 4B.

The HIFU transducer frequency used in this device was selected based on several requirements, including: (1) the ability to administer HIFU therapy to uterine fibroids up to a maximum distance of about 6 cm from the cervix; and, (2) an intensity gain of about 20 dB from the transducer surface to the focal spot, providing about 1,000 W/cm$^2$ at the focus, and about 50 W/cm$^2$ at the transducer surface. These values are reasonable for both treatment and transducer operation. Two different embodiments of the chambers containing degassed water are contemplated for the purpose of coupling the HIFU to adjacent tissue. These embodiments include a chamber containing just the HIFU transducer, and a chamber containing both the HIFU transducer and the imaging scan head.

Figure 4B:
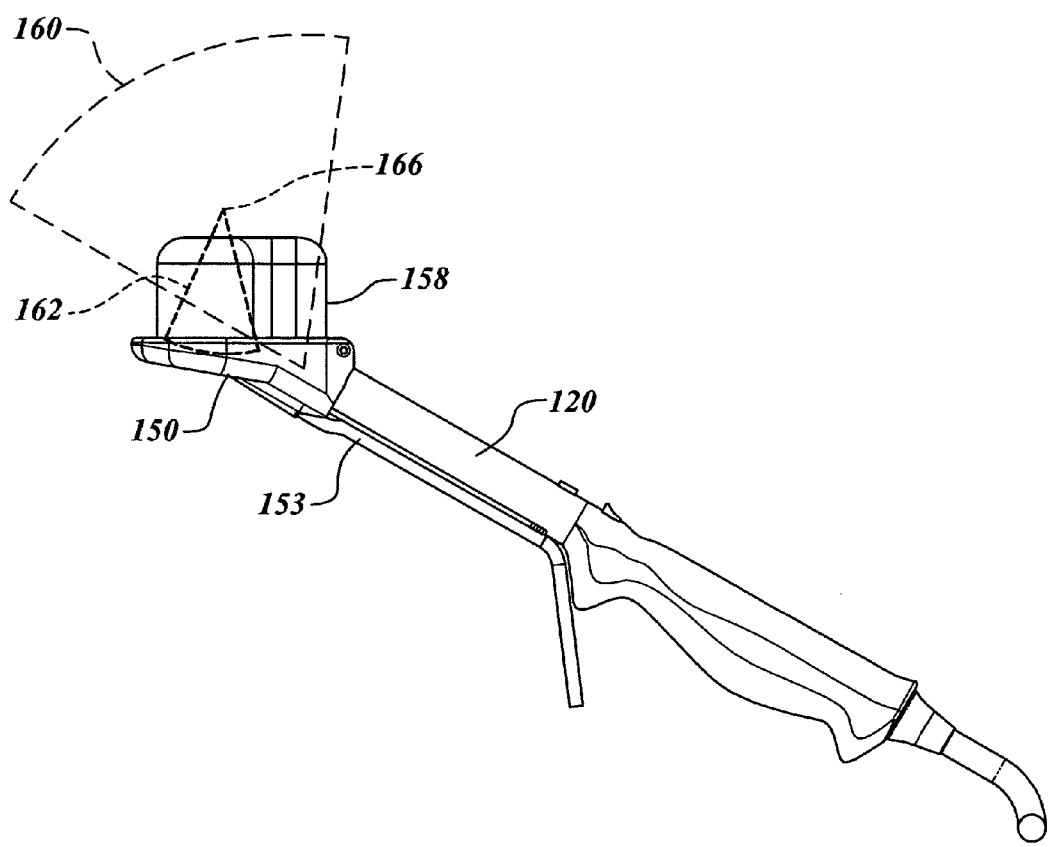
FIG. 4B is a schematic view of the second embodiment of the combination HIFU module and conventional vaginal probe of FIG. 4A, including a liquid-filled chamber and wave patterns of both the imaging and therapeutic transducers.

FIG. 4B illustrates the combination transvaginal probe and HIFU transducer of FIG. 4A with both the imaging and HIFU transducer energized and chamber 158 filled with liquid. The HIFU transducer produces a cone-shaped HIFU wave 162 that is focused at a focal point 166. The imaging transducer generates a scanning ultrasound wave 160. It should be noted that HIFU wave 162 is within scanning ultrasound wave 160. Thus, focal point 166 can be readily seen in the image provided by scanning ultrasound wave 160.

Figure 5A:
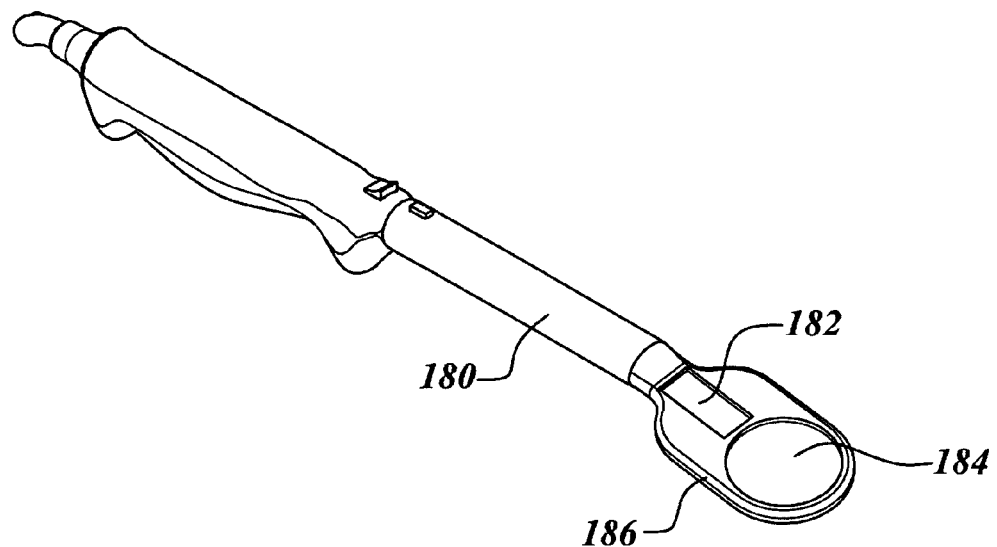
FIG. 5A is a schematic view of combination vaginal probe that includes therapeutic and imaging transducers integrated into a paddle-shaped distal end.
Figure 5B:
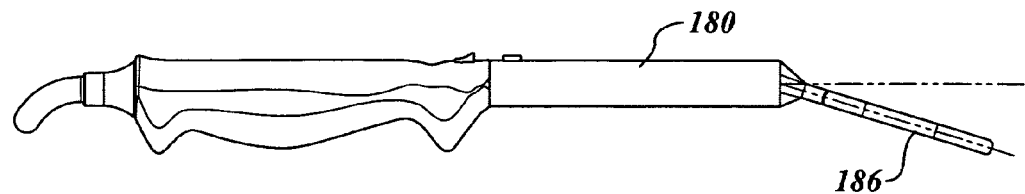
FIG. 5B is a side elevational view of the integrated probe of FIG. 5A illustrating how a position of the paddle-shaped head can be varied around a pivot joint.

FIGS. 5A and 5B illustrate an embodiment of an ultrasound probe usable in the present invention, in which the HIFU therapy transducer and imaging transducer have been integrated into a single device. It is expected that as the combination of real-time imaging and HIFU therapy gains acceptance, clinicians will desire an integrated device rather than a HIFU transducer and an imaging transducer configured as two separate components, mounted together on a single probe. An integrated imaging transducer and a therapy transducer are formed as a combination transvaginal probe 180, as shown in these Figures. FIG. 5B illustrates that the angle of a paddle head 186 containing both the therapy and imaging transducers is movable relative to the body of combination transvaginal probe 180. As was discussed in regard to the first embodiment of the transducer module that included the pivoting HIFU transducer, it is expected that paddle head 186 will be placed in a desired position prior to placing combination transvaginal probe 180 into a patient's vaginal canal. However, it is again envisioned that a linkage mechanism can be incorporated that will enable paddle head 186 to be moved relative to the handle portion of combination transvaginal probe 180, while the paddle head is disposed in the vaginal canal. The paddle head configuration is particularly well suited for use in the vaginal canal.

Figure 6:
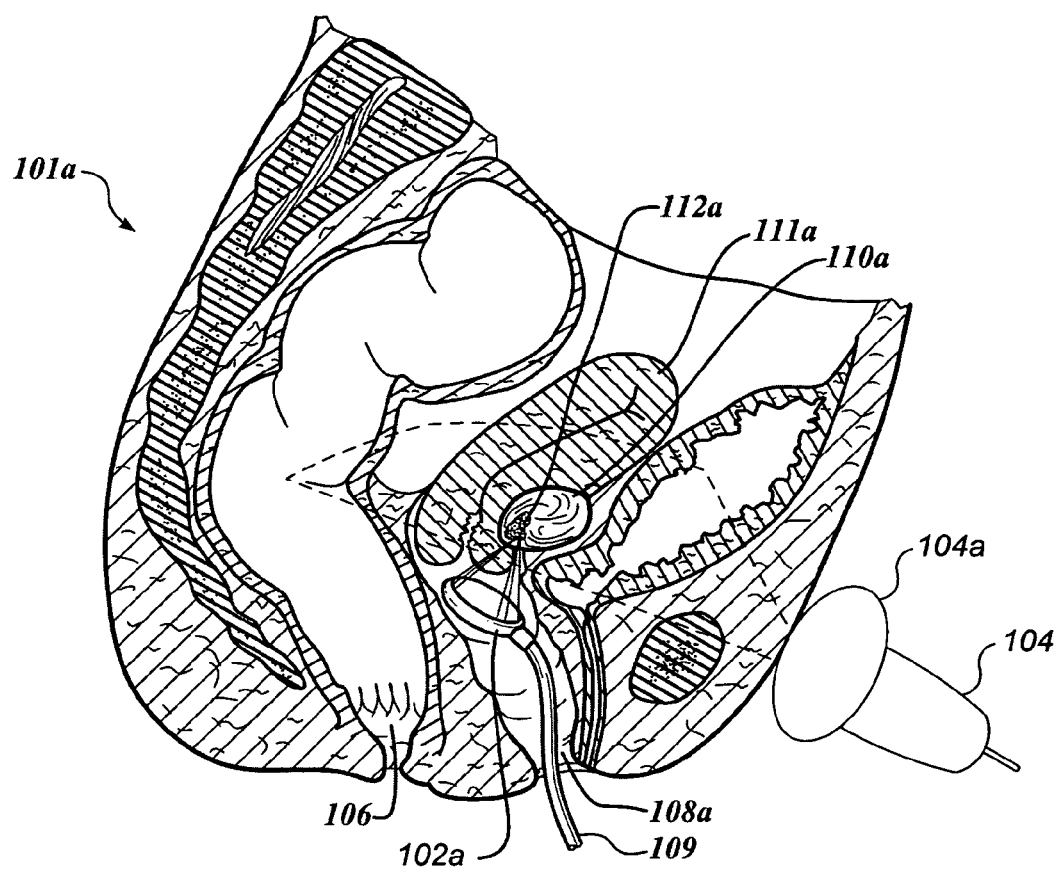
FIG. 6 is a schematic view of a vaginal therapy probe that includes a therapeutic HIFU transducer and a transabdominal imaging probe being used for the simultaneous imaging and treatment of a tumor in a female reproductive system.

While each of the combination imaging and therapy probes discussed above are useful, it should be noted that there is limited room for medical instruments in the vaginal cavity, and the combination probes described above are each larger than a vaginal probe configured only for providing HIFU therapy would need to be. It should also be recognized that many medical offices have access to other types of ultrasound imaging probes, such as transabdominal imaging probes. Thus, one aspect of the present invention is directed to using the relatively ubiquitous transabdominal ultrasound imaging probes with a transvaginal HIFU probe to achieve simultaneous imaging and administration of HIFU therapy for a treatment site. In FIG. 6, a HIFU transducer 102a is included on a vaginal probe 109, and an imaging transducer 104a is part of a transabdominal probe 104. Vaginal probe 109 has been inserted into a vaginal canal 108a and positioned to enable imaging transducer 104a of transabdominal probe 104 to be used in generating an ultrasonic image of a tumor 10a. Once tumor 10a has been located, HIFU transducer 102a is focused on a selected portion of tumor 10a to which the clinician desires to administer the HIFU therapy to generate a lesion 112a. The HIFU therapy is used to destroy the tumor by causing lesions of the blood vessels supplying oxygen and nutrients to the tumor, thereby generating a plurality of lesions similar to lesion 112a, so that the tumor withers away, or by destroying spaced-apart portions of the tumor. Particularly if the latter technique is used, the HIFU therapy will likely be repeated at intervals of several weeks. The time between successive therapy sessions enables macrophages in the patient's body to clear away or debride the necrotic tissue from the tumor so that it is reduced in size with each therapy session and is eventually destroyed.

It must be recognized that because HIFU transducer 102a and imaging transducer 104a are not both disposed on vaginal probe 109, maintaining the required spatial orientation between HIFU transducer 102a and imaging transducer 104a, such that the focal point of the HIFU beam provided by HIFU transducer 102a lies within the imaging plane provided by imaging transducer 104a, can be problematic. Once transabdominal probe 104 and vaginal probe 109 are properly positioned, if either probe (or the patient) changes position, the spatial orientation or relationship between the therapy and imaging probes may be changed, such that the focal point of the HIFU beam may no longer lie within the imaging plane provided by the imaging transducer. Clearly, such movement can undesirably result in the inability to monitor the effects of the HIFU therapy being administered, in real time.

Thus one aspect of the present invention is a frame configured to simultaneously support a transvaginal therapy probe and a transabdominal imaging probe, such that once a preferred spatial orientation or relationship between the transvaginal therapy probe and the transabdominal imaging probe is achieved, movement of either probe (or patient movement) will not result in undesirably changing the spatial relationship between the probes.

FIG. 7A schematically illustrates a frame 200 movably supporting a transabdominal imaging probe 202 and a transvaginal therapy probe 204. Frame 200 includes a pair of generally elongate support members 208 and 210, and a pair of brackets 212 and 230. When an adjustment member 218 is loosened, support member 208 slidingly engages bracket 212, as indicated by an arrow 220. Note that support member 208 includes a pair of parallel arms 208a and 208b, and each arm slidingly engages a corresponding channel formed in bracket 212. Thus, arm 208a slidingly engages a channel 212a, and arm 208b slidingly engages a channel 212b. When adjustment member 218 is secured, support member 208 does not move relative to bracket 212. A support bracket 222 is pivotably coupled to a distal end of support member 208. Support bracket 222 is configured to support transabdominal imaging probe 202. When an adjustment member 226 is loosened, support bracket 222 and transabdominal imaging probe 202 can be moved relative to support member 208 (as indicated by an arrow 228), thus enabling an imaging plane 202a provided by transabdominal imaging probe 202 to be selectively positioned. When adjustment member 226 is secured, the position of support bracket 222 and transabdominal imaging probe 202 are fixed relative to support member 208. Note that support bracket 222 and transabdominal imaging probe 202 can pivot relative to frame 200.

Bracket 212 further includes an orifice 212c, configured to slidingly engage support member 210. When an adjustment member 214 is loosened, support member 210 slidingly engages bracket 212 (as indicated by an arrow 216), and when adjustment member 214 is secured, support member 210 does not move relative to bracket 212. Support member 210 includes a channel 210a configured to engage adjustment member 214. Thus, support member 210 can move relative to bracket 212 throughout the entire extent of channel 210a. Support member 210 further includes a curve 210b configured to enable a transvaginal therapy probe 204 to be properly positioned relative to transabdominal imaging probe 202, as is more clearly illustrated in FIG. 8.

Bracket 230 is attached to a distal end of support member 210. Bracket 230 is configured to slidingly engage transvaginal therapy probe 204. When an adjustment member 232 is loosened, transvaginal therapy probe 204 slidingly engages bracket 230, enabling the position of transvaginal therapy probe 204 to be adjusted as desired. Bracket 230 enables transvaginal therapy probe 204 to rotate relative to bracket 230 (as indicated by an arrow 236), as well as to slidingly engage bracket 230 (as indicated by an arrow 234). When adjustment member 232 is secured, the position of transvaginal therapy probe 204 relative to support member 210 is fixed. A HIFU transducer 205 is disposed in a distal end of transvaginal therapy probe 204. When energized, HIFU transducer 205 produces a beam 205a that converges at a focal point 206. As discussed above, a sufficiently energetic HIFU beam causes tissue necrosis at focal point 206. It should be apparent from the relative positions of imaging plane 202a and HIFU beam 205a, that when transabdominal imaging probe 202 is properly positioned relative to transvaginal therapy probe 204, focal point 206 lies within imaging plane 202a, such that during administration of the HIFU therapy, a clinician can observe focal point 206 in real time (so long as the HIFU transducer is properly pulsed and synchronized, as described above). Support member 208 (i.e. arms 208a and 208b) can be translated to a position normal to (i.e., perpendicular to) arm 210, as indicated by an arrow 216. The process of securing the adjustable members such that the relative positions of the therapy probe and imaging probe are fixed relative to each other (and relative to frame) can be considered to be mechanically fixing the current spatial relationship and orientation between the ultrasound imaging transducer and the HIFU transducer.

Support bracket 222 of frame 200 as illustrated is configured to accommodate a Sonosite C60™ 4-2 MHz (available from Sonosite Inc., Bothell, Wash.) abdominal probe. It should be understood that support bracket 222 can alternatively be configured to accommodate abdominal imaging probes of various other makes and models.

FIG. 7B is based on FIG. 7A; however, FIG. 7B includes a modified transvaginal therapy probe 204a. The distal end of transvaginal therapy probe 204a has been modified to include an articulated joint 238 that couples the distal end of transvaginal therapy probe 204a (including HIFU transducer 205) to the main elongate body of transvaginal therapy probe 204a. A mechanical linkage 240 is attached to the distal end of transvaginal therapy probe 204a and extends along the main elongate body of transvaginal therapy probe 204a to a proximal end of transvaginal therapy probe 204a. A clinician can manipulate the proximal end of mechanical linkage 240 to selectively position the distal end of transvaginal therapy probe 204a, as indicated by an arrow 242. The range of movement indicated by arrows 234, 236 and 242 enable a clinician to selectively position focal point 206 throughout a relatively large treatment volume. Mechanical linkage 240 can be used to sweep focal point 206 throughout a portion of the treatment site without requiring the main elongate body of transvaginal therapy probe 204a to be repositioned (i.e., the mechanical linkage can be used to move focal point 206 without requiring adjustment member 232 to be loosened). If such movement of the focal point ever causes the focal point to move out of the imaging plane provided by the imaging transducer, adjustment member 232 (or adjustment member 226) can be loosened to enable the spatial orientation between the transabdominal imaging probe and the transvaginal therapy probe to be manipulated until the focal point of the HIFU transducer can once again be visualized in the image provided by the imaging probe. While not specifically shown, if should be understood that frame 200 can be coupled to a fixed object for support, such as a table or equipment stand. However, frame 200 does not need to be coupled to a fixed object for support, because when the transvaginal therapy probe and the transabdominal imaging probe are properly positioned, the frame does not require additional support. In particular, the transabdominal imaging probe rests on the patient's abdomen, which provides substantial support to frame 200.

FIG. 8 schematically illustrates how frame 200, transabdominal imaging probe 202, and transvaginal therapy probe 204 are used. Transabdominal imaging probe 202 is coupled to support bracket 222, and transvaginal therapy probe 204 (or 204a) is inserted into bracket 230. Frame 200 is positioned relative to a female patient such that transvaginal therapy probe 204 can be inserted into the vagina. As discussed above, manipulating adjustment member 232 enables transvaginal therapy probe 204 to be positioned as desired. An expandable member 244 (attached to the distal end of transvaginal therapy probe 204) is filled with liquid (such as saline solution) and engages the uterine wall. Expandable member 244 (which can comprise a condom) facilitates acoustic coupling of the HIFU transducer to tissue. With adjustment members 214, 218 and 226 in their loosened positions, transabdominal imaging probe 202 can be selectively positioned on the patient's abdomen, and energized to generate imaging plane 202a. The HIFU transducer incorporated into transvaginal therapy probe 204 is then energized at a low level (i.e., using a power level that will produce a HIFU beam not sufficiently energetic enough to cause tissue damage or tissue necrosis), and the relative positions of transvaginal therapy probe 204 and transabdominal imaging probe 202 are manipulated until focal point 206 is observed within imaging plane 202a. Once the relative positions of transvaginal therapy probe 204 and transabdominal imaging probe 202 enable visualization of the focal point as desired, each adjustment member is secured to ensure that the spatial orientation between transvaginal therapy probe 204 and transabdominal imaging probe 202 does not change. Patient movement should not effect the spatial orientation between transvaginal therapy probe 204 and transabdominal imaging probe 202 once each adjustment member is secured. The HIFU transducer in transvaginal therapy probe 204 is then energized at a power level that is sufficiently energetic so as to induce tissue necrosis at the focal point, which is aligned with the treatment site. If desired, adjustment member 232 can be loosened during therapy to enable vaginal therapy probe 204 to be moved, which in turn will move the position of the focal point. If such movement causes the focal point to move out of imaging plane 202a, the power level of the HIFU transducer can be lowered to a level insufficient to cause tissue damage or necrosis, until the spatial orientation between transvaginal therapy probe 204 and transabdominal imaging probe 202 is adjusted as desired, such that the focal point is once again included within imaging plane 202a. It should be noted that when transvaginal therapy probe 204a is employed, manipulation of mechanical linkage 240 will enable focal point 206 to be moved without requiring manipulation of adjustment member 232. It will be understood (as discussed above) that for focal point 206 to be visualized during the application of high power levels of the HIFU, noise introduced into the ultrasound image by the HIFU beam must be shifted by appropriate synchronization, to a portion of the ultrasound image that is spaced away from the focal point (see FIG. 1C).

FIG. 9 is a composite ultrasound image, including an original ultrasound image 246 and an enlarged and annotated ultrasound image 248. In particular, annotated image 248 illustrates an area of potential treatment 250. When transvaginal therapy probe 204 or modified transvaginal therapy probe 204a is introduced into the vagina, the focal point of the HIFU beam generated by the ultrasound transducer in either transvaginal therapy probe should be able to reach any location within the area of potential treatment. Transvaginal therapy probe 204a (see FIG. 7B), which includes the articulated joint between the main body of transvaginal therapy probe and the distal end of the transvaginal therapy probe, can enable the focal point to be swept over relatively large portions of the area of potential treatment, without requiring repositioning of the main body of the transvaginal therapy probe.

FIGS. 10 and 11 provide details regarding the distal end of transvaginal therapy probe 204, while FIGS. 12A-12F are photographs illustrating the fabrication of a working model of transvaginal therapy probe 204. Referring to FIG. 10, expandable member 244 is coupled to a housing 252 using o-ring 264. In a working embodiment, housing 252 was implemented using brass, and a groove was included in the housing to accommodate o-ring 264 (see also FIG. 12E). A fluid line 254 is used to selectively inflate and deflate expandable member 244 (see also FIGS. 12E and 12F). An aluminum lens 256 is attached to the distal end of housing 252. As discussed in detail below, one embodiment of the present invention includes an aluminum lens that is used to focus a HIFU beam in the vaginal environment.

Figure 12A:
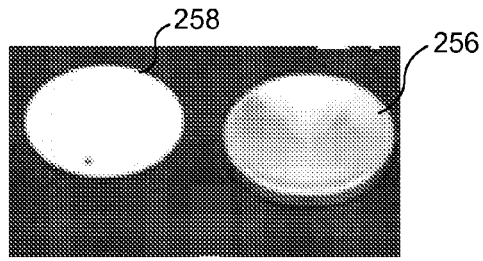
Figure 12B:
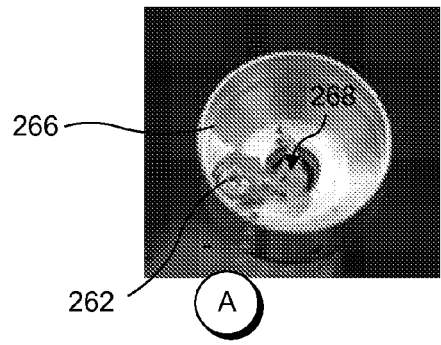
Figure 12C:
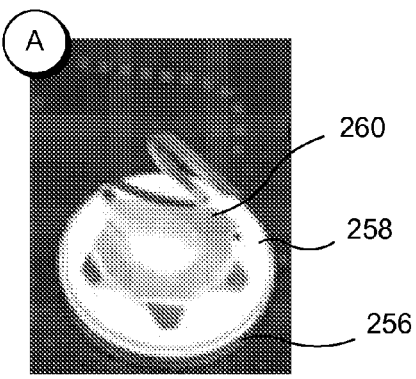
Figure 12D:

FIG. 11 illustrates a cross-sectional view of a distal end of transvaginal therapy probe 204. The HIFU transducer is implemented using a PZT-8 crystal 258, which is securely bonded to aluminum lens 256. FIG. 12A is a photograph of crystal 258 and aluminum lens 256 before they are bonded together. The crystal utilized in a working model is a flat, circular disk piezoceramic crystal (APC 880™, from American Piezoceramics, Duck Run, Pa.), with dimension of about 25.4 mm in diameter and 0.59 mm in thickness (corresponding to half wavelength of APC 880 at 3.5 MHz). In the working prototype, the crystal was adhered to the aluminum lens with a thin layer (approximately 0.025 mm) of epoxy (Hysol RE2039™ and HD3561™, available from Loctite Corporation, Rocky Hill, Conn.). The bonding surfaces were roughened with a fiberglass brush and cleaned with acetone in an ultrasonic cleaner to ensure optimal bonding conditions. A custom built plastic (Delrin™) fixture and molds made of silicone rubber (RTV 630 A™ and RTV 630™ B, 10:1 by mass, available from GE Silicones, Waterford, N.Y.) ensured concentric alignment of the crystal and the lens during bonding. The crystal and lens were bonded under pressure (approximately 400 kPa), and the epoxy was allowed to set at a temperature of 150° C. for 3 hours.

Figure 12E:
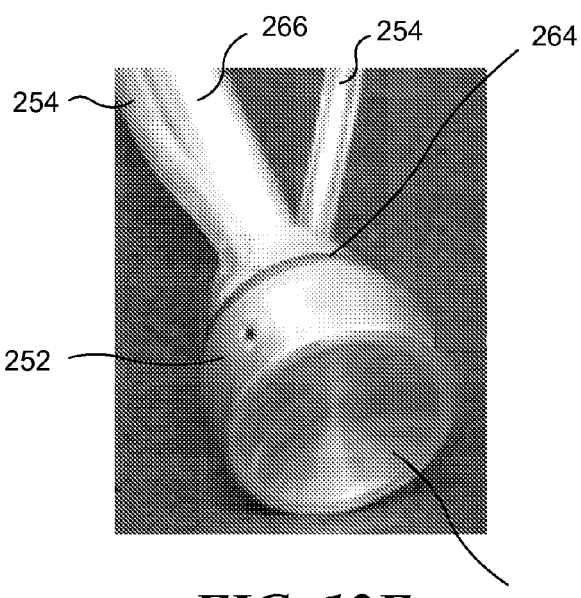
Figure 12F:
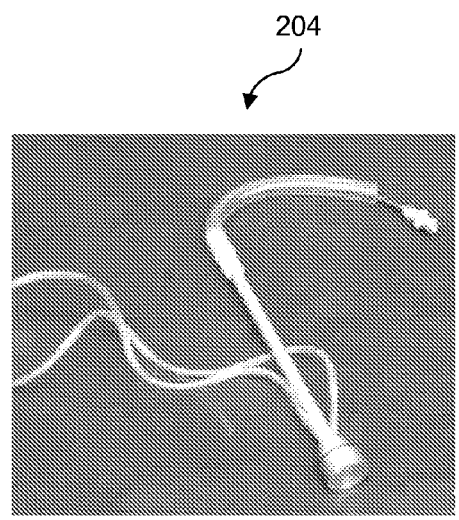

The main elongate body of the working model of transvaginal therapy probe 204 was implemented using a 9.52 mm (⅜") outer diameter hollow aluminum tube 266 (see also FIGS. 12E and 12F). Tube 266 was adhesively coupled (using Threadlocker 271™ adhesive, from Loctite Corporation, Rocky Hill, Conn.) to the brass housing (i.e., housing 252). A flexible coaxial cable 268 (RG-58 coaxial cable), approximately 10 cm longer than aluminum tube 266, was fed through the handle and its ground braiding was attached to the inside of the brass housing with a screw 262 for a ground connection (see FIG. 12B, in particular). To prevent electrical shorting, the inside of the brass housing, the braiding, and the screw were coated with epoxy, which provided isolation relative to the exposed coaxial cable center. The exposed coaxial cable at the end of the handle was encased in plastic tubing (R3603, ½" ID, from Saint-Gorbain Performance Plastics, Wayne, N.J.), and the tubing was secured to the handle using a plastic tubing connector to protect the transducer from water exposure. A conductive O-ring 260 (FIG. 12D) was cut from 0.25 mm thick gold foil and soldered onto the center of the coaxial cable and the crystal to electrically couple to crystal 258 (note connector A shown in FIGS. 12B and 12C). The completed transducer (i.e., the combined lens 256/crystal 258 assembly) was placed into brass housing 252 and secured with epoxy (Hysol RE2039™ and HD3561™, from Loctite Corporation, Rocky Hill, Conn.). The crystal was air backed to ensure both cooling and minimum energy loss through the back-side. FIG. 12F is a photograph of the completed working model of transvaginal therapy probe 204.

As noted above, the purpose of using frame 200 to control the spatial orientation between transvaginal therapy probe 204 and transabdominal imaging probe 202 is to enable real-time, image-guided HIFU therapy. However, when the HIFU source is in operation, the high power levels saturate the ultrasound image probe receiver and circuitry, resulting in interference band patterns on the ultrasound image. To ensure that the image is interference-free where the focal point of the HIFU beam is to be visualized in the ultrasound image, the pulse gating method described in a related U.S. Pat. No. 6,425,867 (entitled "Noise-Free Real Time Ultrasonic Imaging of a Treatment Site Undergoing High Intensity Focused Ultrasound Therapy"), is used. As explained above and in this referenced patent, the HIFU source and the imaging ultrasound source are synchronized so that the interference area, proportional to the duty cycle, is spatially stable and moveable, as schematically illustrated in FIGS. 1B and 1C. It has been empirically determined that when the Sonosite C60 image probe is used in conjunction with frame 200 and transvaginal therapy probe 204, a 50% HIFU duty cycle is adequate for visualization of the HIFU focal point, resulting in a 65-70 degree window of visualization (out of a total ultrasound imaging window of 135 degrees), as shown in FIGS. 13A and 13B. An ultrasound image 270 in FIG. 13A includes a 67 degree window 272 of visualization that is noise free. Note that window 272 is disposed about 10 degrees from the left edge of the image, so that noise 274a obscures the first 10 degrees of ultrasound image 270, and noise 274b similarly obscures the last 58 degrees. An ultrasound image 276 in FIG. 13B also includes a 67 degree window of visualization that is noise free (i.e., a window 278). Note that window 278 is shifted relative to noise free window 272 of FIG. 13A. Thus, in FIG. 13B, window 278 is disposed about 40 degrees from the left edge, so that noise 280a obscures the first 40 degrees of ultrasound image 276, and noise 280b similarly obscures the last 28 degrees. Accordingly, the window of visualization can be shifted to ensure that the focal point of the HIFU beam can be visualized in the noise free portion of the ultrasound image. It should be understood that the window of visualization is dependent upon the image probe used and the imaging frame rate, and thus, other transabdominal imaging probes (or other frame rates) might result in a larger or smaller window of visualization.

FIG. 14 is a block diagram 284 that illustrates the functional elements used to empirically test the functionality of the present invention. The HIFU transducer incorporated into vaginal therapy probe 204 (or vaginal therapy probe 204a) was driven with an RF amplifier 286 (Model ENI A150™, from MKS instruments, Andover, Mass.). A first waveform generator 294 (Model 33120A™, from Agilent Technologies, Palo Alto, Calif.) was used to provide the source signal. An RF power meter 288 (Model 4421™, Bird Electronics, Cleveland, Ohio) was connected between the amplifier and a matching network 290 to monitor electrical power output. A switch 292 was coupled between the output of waveform generator 294 and RF amplifier 286, to serve as an on/off switch. A timer 296 connected to the switch enabled HIFU exposure time to be measured. In order to provide synchronization (i.e., to enable visualization of the focal point of HIFU beam by shifting noise introduced into an ultrasonic imaging by the HIFU beam, as described above), a second waveform generator 298 and a computer 300 were utilized.

Computer 300 employed LabView™ software (National Instruments of Austin, Tex.) to control both waveform generators via a GPIB (General Purpose Interface Bus) connection. Waveform generator 298 was used to generate an excitation pulse. The excitation pulse triggered the output of waveform generator 298, which operated in burst mode, with a burst count corresponding to a 50% duty cycle. To ensure that the interference bands were spatially stable, the excitation pulse must always fall on the same image probe array element. The excitation pulse frequency (EPF) varied with imaging depth and was determined experimentally (by changing the EPF until the interference bands were spatially stable) and was then entered manually into the LabView™ control program. As described above, frame 200 ensures that the spatial orientation between transabdominal imaging probe 202 and transvaginal therapy probe 204 remains constant once it has been adjusted so that the focal point of the HIFU beam generated by transvaginal therapy probe 204 (or transvaginal therapy probe 204a) lies within the imaging plane generated by transabdominal imaging probe 202. The ultrasound image generated by transabdominal imaging probe 202 is viewed on a display 302.

Having described the frame used to maintain the spatial orientation between an imaging probe and a therapy probe, and the technique implemented to shift noise generated by the HIFU beam within an ultrasound image (to enable visualization of the focal point of the HIFU beam during therapy), we turn now to describing the development of the HIFU transducer and alumina lens utilized in the transvaginal therapy probe described above.

Development of HIFU with Aluminum Lens

A study of the female pelvic anatomy was performed to determine the optimal geometry and dimensions for transvaginal therapy probe 204 and frame 200. Images from the Visible Human Project (National Library of Medicine, National Institute of Health), Gray's anatomy, 18 pelvic ultrasounds, and fibroid patient data files were used. Various configurations of transvaginal therapy probes and frames were modeled with SolidWorks™ (SolidWorks Corporation, Concord, Mass.) design software to determine optimal component sizes and geometry based on the above noted anatomical study.

The anatomical study revealed vaginal lengths ranging from 6-11 cm, uterine lengths of 5-9 cm, and uterine widths of 2-5 cm. A transvaginal therapy probe in accord with the present invention was designed to treat fibroids along the uterine cavity while placed in the vaginal formix surrounding the cervix. Therefore, a HIFU focal length of 4 cm was determined to be optimal.

Numerical simulations indicated that an aluminum lens would be effective in focusing ultrasound energy. It was determined that a flat crystal and lens design (versus a spherical shell) would be used due to crystal availability, cost, and the possibility of using various lens geometries and focal configurations in the future. Aluminum has a low acoustic loss and a low characteristic acoustic impedance ($Z_{Al}$=17.3 Mrayls) relative to most metals ($Z_{steel}$=46.7 Mrayls, $Z_{copper}$=42.5 Mrayls, and $Z_{titanium}$=27.0 Mrayls), making aluminum a suitable material for an acoustic lens in terms of minimizing attenuation and acting as an acoustic matching layer. Due to the high acoustic velocity of aluminum (6363 m/s) compared to water (1483 m/s), the curvature of the lens was small, and the maximum thickness of the lens was only 3 mm.

Based on the desired focal length and calculated attenuation losses in uterine tissue and fibroids, a PZT-8 crystal, 2.54 cm in diameter with a nominal frequency of 3.5 MHz, was selected to provide a sufficient focal gain. A 2.54 cm aluminum lens with a 4 cm focal length resulted in a maximum lens thickness at the outer edge of 3 mm and an f-number of 1.57. Although side lobes were noticed in the Schlieren imaging, they were quantified as relatively small (approximately 20 dB) compared to peak focal intensities on the field map. Such side lobes may be a result of re-radiation, reflections, and shear wave conversion within the lens and at the crystal-epoxy-lens interface, since they were apparent in another HIFU transducer design at similar power levels, which also involved the use of a PZT crystal bonded to an aluminum waveguide. Although the epoxy used to bond the aluminum lens to the PZT was nonconductive, roughness on both lens and PZT surfaces at the microscopic level allowed for areas of direct contact and thus, conduction while the two surfaces were bonded under 400 kPa of bonding pressure.

The maximum diameter of the brass housing for the PZT crystal and aluminum lens combination was 28.5 mm, which is sufficiently small to readily fit into the vagina. While optimizing the HIFU transducer size to fit in the vagina, it was ensured that the aperture size chosen was able to deliver sufficient power to the treatment site. A transvaginal versus transabdominal treatment approach was chosen since it provided the shortest acoustic path to the uterus (approximately 0.5 cm from the vaginal formix to the uterus, versus approximately 4 cm via the abdomen, depending on bladder size). The large attenuation loss associated with the abdominal path (losses in skin, fat, abdominal wall, and bladder fluid) were thus eliminated using the transvaginal approach.

The frame design employed to maintain the spatial orientation between an external imaging probe and the internal therapy probe (see FIGS. 7A and 7B) enables motion in three degrees, including: (1) rotation of the image probe independently of the frame so that the image probe can follow the contour of the body, and so that the image can be adjusted, while ensuring the HIFU focus remains in the image plane; (2) horizontal movement of the image probe to accommodate vaginal lengths between 6 and 15 cm and various tumor locations; and, (3) variable vertical separation of 5-15 cm between the image probe and the therapy probe, enabling the frame to be used in women of various weights. Although the Sonosite C60™ 4-2 MHz abdominal probe was used as the image probe, the frame is designed to enable abdominal imaging probes of various makes and models to be used, as well as HIFU transducers of various frequencies and focal lengths. As noted above, the function of the frame is to ensure that the imaging probe and therapy probe are aligned so that the HIFU focus is within the image plane, enabling real-time visualization of HIFU treatment.

As noted above, a piezoelectric ceramic (PZT-8) crystal was selected to generate the HIFU, and an aluminum lens was selected to focus the HIFU beam. The curvature of the aluminum lens was calculated such that waves from each point on the surface of the crystal would pass through the lens and arrive at the focus at the same time. This focusing effect is schematically illustrated in FIG. 15A, for a lens focusing at 4 cm, where $t_{1i}+t_{2i}=t_0$ and i represents a point location on the crystal. The variables used in Equation 1 (below) that govern the shape of the lens are indicated in FIG. 15A. The coordinates of the lens curvature fit the quadratic relation in Equation (1), where $(x_i, y_i)$ are the coordinates of the lens curvature, $x_f$ is the focal length, and $c_1$ and $c_2$ are the measured acoustic velocities in the aluminum lens (6363 m/s) and in water (1483 m/s), respectively:

$$x_i^2\left(1 - \frac{c_2^2}{c_1^2}\right) + x_i\left(2x_f\frac{c_2}{c_1} - 2x_f\right) + (y_i^2) = 0 \quad (1)$$

A computer simulation was used to determine the effectiveness of the aluminum lens in focusing ultrasound. Wave 2000 Pro™ (Cyberlogic, New York, N.Y.), a program for studying two-dimensional (2D) wave propagation fields, was used to compute the finite difference solution to the 2D wave equation in both spatial and temporal domains. Shear and compression coupling and viscous loss attenuation were included in the algorithm. The geometry, material properties, and ultrasound sources and receivers were modeled. The geometry, shown in FIG. 15B, consisted of a simplified model of the transducer: an air-backed PZT-8 crystal bonded to an aluminum lens with an epoxy bond layer. Source pulses of 3 ms and continuous wave sources were modeled in a simulated treatment path consisting of water and uterine tissue. Simulated ultrasound point receivers for particle displacement measurement were located at the focus and at various points along the focal axes (1, 2, 5, 10, and 20 mm to the left and right of the focus, and 1, 2, and 5 mm above and below the focus), as depicted in FIG. 15B. The time duration for each simulation was set at 45 ms, allowing the wave to propagate a few centimeters past the focus. Normalized particle displacement data were extracted from the simulations. An aluminum lens developed using the above described model was machined using a CNC lathe. Fabrication of the transvaginal therapy probe is described above.

Wave 2000 Pro™ computer simulations demonstrated the feasibility of the aluminum lens design in focusing ultrasound. A propagating 3 ms pulse for a 3.5 MHz sinusoidal ultrasound source focusing at 4 cm through an aluminum lens at various times was simulated. The normalized peak particle displacement amplitudes determined from simulation receiver data at various locations were also calculated. FIG. 16A is a composite of images extracted from the Wave 2000 Pro™ simulation, showing a 3.5 MHZ, 3 µs sinusoidal pulse wave at four different times (7 µs, 21 µs, 30 µs, and 37 µs). The approximate time when the wave front reached the focus was at 30 µs. The program created a black background during the simulation for contrast, and the various minima and maxima of the wave are shown in white, with areas that remain black showing locations where the waveform has zero amplitude.

FIG. 16B graphically illustrates the peak normalized particle displacements collected from the Wave 2000 Pro™ simulation receiver data. Since acoustic pressures are proportional to particle displacements, the half-pressure maximum focal dimensions can be estimated as being about 10 mm in length by about 1 mm in width, as indicated in FIG. 16B.

The actual acoustic beam pattern provided by the aluminum lens and PZT-8 crystal fabricated as described above was initially determined with a Schlieren imaging system at three different acoustic power levels, including: 10, 30, and 60 W (continuous wave). FIG. 17A illustrates a composite of the Schlieren images obtained at the above noted power levels. Side lobes 304 are indicated at power levels around 60 W.

FIG. 17B graphically illustrates an acoustic field map created using data collected with a PVDF needle hydrophone (from NTR Systems Inc., Seattle, Wash.) during empirical testing of the transducer generated using the PZT-8 crystal and the aluminum lens described above. Technically, the act of transduction of energy (from electrical to a acoustical) is performed by the crystal, however, those of ordinary skill in the art will readily recognize that the term transducer is often used to refer not only the crystal itself, but also to a crystal combined with a lens. The hydrophone was 0.5 mm in diameter and was moved using stepper motors. The acoustic power output was determined using a radiation force balance technique. The field map shows the HIFU focus at a half-pressure maximum (26 dB) with measured dimensions of about 11 mm in length and about 1.2 mm in width, which are similar to the values predicted with the computer model. Side lobes can be seen but were at values below approximately 20 dB. The acoustic power output was determined using a radiation force balance technique.

Results obtained from the radiation force balance are shown in FIG. 18. This plot shows the correlation between electrical power and acoustic power, as well as the efficiency at the power levels tested. The average efficiency between 0 and 150 W of acoustic power was determined to be 58%, +/−2% (n=9 power levels).

In-vitro testing of the PZT-8/aluminum lens transducer in gel and animal tissue verified the functionality of the design. A transparent tissue-mimicking gel phantom was used to determine if lesions can be formed at target locations, if these lesions can be visualized using ultrasound, and if the water balloon affects the formation of lesions. The thermally sensitive gel employed was based on a combination of bovine serum albumin and polyacrylamide, and changes from transparent to opaque when treated with HIFU. The attenuation of the gel was measured to be 0.012+/−0.002 NP/cm/MHz (n=30). Gel blocks (6.5×5.5×5.5 cm) were placed in a plastic holder, submerged, and anchored in a plastic tank filled with degassed distilled water at room temperature. The transvaginal therapy probe described above (i.e., transvaginal therapy probe 204) was suspended in the water tank using a metal clamp and positioned such that the focal region of the HIFU transducer was within the gel block, and the image probe was capable of visualizing the treatment.

Three treatment scenarios were investigated, as follows: (1) the transducer was placed directly on the gel surface; (2) the transducer was placed 1.2 cm away from the gel surface and separated therefrom by a water-filled condom; and, (3) the transducer was placed 1.2 cm away from the gel surface without a water-filled condom intervening. All lesions were produced using 46 W of acoustic power for 5 seconds at 50% duty cycle. The ultrasound imaging unit (Sonosite™, from Sonosite Inc., Bothell, Wash.) was connected to a digital video recorder and ultrasound images were recorded during treatment. A digital camera, mounted on a tripod, was used to photograph lesions formed in the transparent gel. Lesion dimensions were measured using these photographs within Adobe Photoshop™ (Adobe Systems Incorporated, Seattle, Wash.).

TABLE I

Measured dimensions for HIFU lesions in gel with and without water stand-off.

| Treatment scenario (n = 10 for each) | In situ focal intensity (W/cm$^2$) | Lesion length (mm) | Lesion width (mm) | Ultrasound visualization |
|---|---|---|---|---|
| Transducer directly on gel | 1410 | 11.2 +/− 0.8 | 2.2 +/− 0.6 | 10/10 |
| 1.2 cm separation; no condom | 1590 | 13.5 +/− 1.1 | 2.6 +/− 0.7 | 10/10 |
| 1.2 cm separation; with condom | 1590[1] | 13.3 +/− 0.9 | 2.5 +/− 0.8 | 10/10 |

[1]Attenuation of the 0.07 mm thin condom (Trojan Brand Non-Lubricated, CWI Carter Products Div., New York, NY) was assumed to be zero.

FIG. 19A illustrates a composite image including both a photograph 320 of the distal end of transvaginal therapy probe 204 coupled to a gel phantom, as well as an ultrasound image 322 of the distal end of transvaginal therapy probe 204 coupled to the gel phantom. In both the photograph and the ultrasound image, brass housing 252, expandable member 244, and aluminum lens 256 can be observed. Note that in ultrasound image 322, the degassed water used to inflate the latex condom (i.e., expandable member 244) can be identified. FIG. 19B is a composite image including a similar photograph and ultrasound sound image, taken after HIFU therapy. A lesion 326 can be observed in both a photograph 324 and in an ultrasound image 328. These images depict a treatment scenario wherein the transducer and gel are separated by 1.2 cm of water contained within a water-filled condom. The HIFU transducer and the water-filled condom are clearly seen in the ultrasound images (i.e., ultrasound images 322 and 328). Lesion 326, which was formed by HIFU, can be clearly seen in photograph 324 as a white opaque spot in the transparent gel, and as a bright hyperechoic spot in ultrasound image 328. The lesion appears to be tadpole-shaped, indicative of the presence of cavitation mechanisms during lesion formation. The measured lesion dimensions for three different treatment scenarios (no condom/no separation, 1.2 cm separation with no condom, and 1.2 cm separation with liquid-filled condom), are shown in Table I. At 46 W of acoustic power and 50% duty cycle, the focal intensity was 1400 W/cm$^2$ with the transducer on the surface of the gel and 1590 W/cm$^2$ with the transducer and gel separated by 1.2 cm of water. A two-sample, two-tailed test indicated no statistically significant difference between lesions created both with the water-filled condom stand-off, and without (P<0.05). Lesion size was proportional to HIFU focal intensity. All lesions were visualized with ultrasound.

The ability for the device to produce and visualize lesions in tissue was then determined using fresh turkey breasts. The turkey breast samples used in the experiment were stabilized at 25° C. prior to treatment and had a measured attenuation of 0.096+/−0.002 NP/cm/MHz. Attempts were made to create lesions perpendicular to the muscle fibers at selected HIFU focal intensities between 500 and 4000 W/cm$^2$, at 5 and 10 seconds of exposure, and 50% duty cycle. The spatial and temporal averaged frequency dependent HIFU focal intensity ISATA was determined to be:

$$I_{SATA} = \frac{P_A * DC}{A}(e^{-2\alpha_T x_T})(e^{-2\alpha_W x_W}) \quad (2)$$

where $P_A$ is acoustic power, DC is duty cycle, A is the half pressure maximum (23 dB) focal area, $\alpha_T$ and $\alpha_W$ are the respective attenuation coefficients of tissue and water, and $x_T$ and $x_W$ are the depths in tissue and water, respectively. The tissue was dissected at the lesion location and lesion length and width were measured using digital calipers. It was noted whether or not each lesion was visualized using ultrasound imaging during treatment.

Such HIFU created lesions, and the ultrasound visualization of treatment in a turkey breast using transvaginal therapy probe 204 are shown in FIGS. 20A and 20B. FIG. 20A is a photograph 330 of a dissected turkey breast, which includes lesions induced by HIFU therapy. A lesion 332a was generated using a power level of 3800 W/cm² applied for 5 seconds; a lesion 332b was generated using a power level of 1600 W/cm² applied for 10 seconds; a lesion 332c was generated using a power level of 2200 W/cm² applied for 5 seconds; and a lesion 332d was generated using a power level of 800 W/cm² applied for 10 seconds. Normal turkey breast (i.e., no lesions) is generally indicated by an arrow 334.

FIG. 20B is a composite image of a turkey breast and a HIFU therapy probe, including an ultrasound image 336a, generated before the application the HIFU beam, and an ultrasound image 336b, generated after the application of the HIFU beam. Each ultrasound image includes a turkey breast 335 and the distal portion of transvaginal therapy probe 204, including aluminum lens 256. A lesion 338 is clearly visible after the HIFU therapy in ultrasound image 336b.

As indicated below in Table II, visualization was successfully achieved 100% of the time at a power level of 3600 W/cm², and 70% of the time at a power level of 1200 W/cm².

TABLE II

Measured dimensions for HIFU lesions in a turkey breast at two intensity levels.

| In situ focal intensity (W/cm²) | Lesion length (mm) | Lesion width (mm) | Number of samples | Ultrasound visualization |
|---|---|---|---|---|
| 1200 | 10.6 +/− 3.1 | 2.1 +/− 0.3 | 10 | 7/10 |
| 3600 | 21.6 +/− 1.1 | 5.1 +/− 0.3 | 10 | 10/10 |

Once the effectiveness of transvaginal therapy probe 204 was empirically tested using gel phantoms and turkey breasts as described above, the ergonomics of transvaginal therapy probe 204, frame 200, and transabdominal imaging probe 202 were tested in six healthy human volunteers, in accordance with a human subjects research protocol approved at the University of Washington. The volunteers were neither pregnant nor had undergone a hysterectomy. A sterile condom (to implement expandable member 244) was secured to the distal end of transvaginal therapy probe 204, lubricated, and filled with water prior to insertion into the vagina. Once the transvaginal therapy probe was inside the vagina, the transabdominal imaging probe was positioned to visualize pelvic structures and the transvaginal therapy probe. Uterus dimensions were measured on the ultrasound image. Once visualization was possible, the transvaginal therapy probe was mechanically moved and positioned to hypothetically treat various areas of the uterus. The amount of transducer movement was quantified using a ruler drawn onto the transvaginal therapy probe and by observing the relative position of the transvaginal therapy probe in the ultrasound image. The distances from the transducer in the transvaginal therapy probe to the fundus, mid-uterus, and cervix were measured to determine the potential treatable area. Water was injected and removed from the condom to determine the feasibility of using a water-filled condom as a stand-off.

TABLE III

Human volunteer statistics and uterus measurements.

| Volunteer | Age (years) | Body mass index | Uterus orientation[d] | Uterus length (cm) | Uterus width (cm) | Distance to cervix[e] (cm) | Distance to mid uterus (cm) | Distance to fundus |
|---|---|---|---|---|---|---|---|---|
| 1 | 26 | 20.4 | A | 6.15 | 3.42 | 1.88 | 2.69 | 3.92 |
| 2 | 27 | 22.0 | A | 5.90 | 3.21 | 1.83 | 2.52 | 3.87 |
| 3[a] | 49 | 22.9 | A | 8.49 | 4.63 | 1.92 | 3.18 | 4.33 |
| 4 | 23 | 22.7 | A | 7.21 | 3.90 | 1.98 | 3.21 | 3.00 |
| 5 | 32 | 29.9 | M | 7.26 | 3.33 | 2.17 | 3.50 | 4.78 |
| 6[b] | 42 | 24.6 | M | 11.7 | 8.03 | 3.61 | 5.64 | 5.44 |
| Mean | 33.17 | 23.75 | | 7.79 | 4.42 | 2.23 | 3.46 | 4.22 |
| St Dev[c] | 12.23 | 3.31 | | 2.13 | 1.84 | 0.69 | 1.13 | 0.84 |

[a]Volunteer had children.
[b]Volunteer had a fibroid located in the fundus.
[c]Standard deviation.
[d]A = aniflexed; M = midline
[e]Distance measure from the aluminum lens of the transvaginal therapy probe.

The position of transabdominal imaging probe 202, frame 200, and transvaginal therapy probe 204 are schematically illustrated in FIG. 8, as discussed in detail above, and visualization of the transvaginal therapy probe, uterus, and surrounding pelvic structures are shown in the ultrasound imaging of FIG. 9. Volunteer statistics and uteri measurements are shown in Table III. The volunteers ranged in age between 23 and 49 years, and in body mass index (weight in kilograms divided by the square of height in meters) between 20.4 and 29.9. One volunteer had previously given birth, and one volunteer had a fibroid located in the fundus. Four volunteers had aniflexed uteri (a condition in which the uterus is pointed towards the abdomen) and two had midline uteri. Uteri length ranged between 5.90 and 8.49 cm and width ranged between 3.21 and 4.63 cm, excluding the volunteer with a fibroid, wherein the total uterus length and width, including the fibroid, were 11.7 cm and 8.03 cm, respectively. As shown in Table III, if treatment was to be administered, the 4 cm focal length of transvaginal therapy probe 204 would have been sufficient to treat fibroids located in the cervix and mid-uterus of all volunteers (an average distance of 2.23 cm and 3.46 cm, respectively).

According to the survey completed by the volunteers after the study, entrance into the vagina was comfortable if lubrication was used and sufficient water was inside the condom to act as a cushion between the vaginal wall and the HIFU transducer (i.e., the distal end of transvaginal therapy probe 204. No discomfort was experienced while the probe was in the vagina and while the probe was being removed from the vagina.

The above-noted study provides a feasibility assessment for image guided HIFU therapy using transvaginal therapy probe 204, transabdominal imaging probe 202, and frame 200 for treating uterine fibroid tumors. The transvaginal HIFU transducer (crystal 258 and lens 256) has the potential to treat fibroids through the width of the uterus when placed in the vaginal formix. In designing transvaginal therapy probes 204 and 204a, and frame 200, anatomical constraints of the female pelvic structures were taken into account. The 28.5 mm diameter transducer head was sufficiently small to fit into the vagina. While optimizing the HIFU transducer size to fit in the vagina, it was ensured that the aperture size chosen was able to deliver sufficient power to the treatment site. Placement of the device in human volunteers demonstrated successful visualization of the HIFU transducer and the uterus. The water-filled condom and the transducer lens surface were easily seen in the ultrasound images. Since the transducer had a fixed focal length of 4 cm, a potential treatment location can be determined on the ultrasound image at a distance of 4 cm away from the transducer lens. Mechanical movement of the HIFU transducer was possible once in the vagina and provided access to a potential treatment area that spanned from the cervix to the fundus of the uterus. The ergonomic study indicated that the insertion, maneuvering, and removal of the probe were comfortable for the volunteers. The ergonomic study also indicated that a HIFU transducer with a fixed focal length of 4 cm is capable of treating fibroids located in the cervix and mid-uterus area in most women with aniflexed and midline uteri. However, fibroids located in the fundus of midline uteri and uteri of women who have previously given birth (i.e., within larger uteri) may require a longer focal length or treatment using transabdominal HIFU. Since an individual lesion is not large enough to cover a fibroid, multiple lesions would be required for fibroid treatment. Therefore, large fibroids may require a long treatment time or not be suitable for HIFU treatment. The target fibroids for this treatment modality are submucosal fibroids. Submucosal fibroids are located under the endometrium of the uterus, accessible with a 4 cm focal length, and represent the most symptomatic type of fibroids. They are often smaller in size than intramural or subserosal fibroids, making them more suitable for HIFU treatment.

The two methods currently used for HIFU therapy visualization are magnetic resonance imaging (MRI) and ultrasound. Both can be used to image fibroids. In an ultrasound image, fibroids often appear hypoechoic (as darkened regions). The Sonosite™ ultrasound unit was chosen for this study, since it allowed for image guidance and was portable and inexpensive compared to larger ultrasound units and MRI. As shown in this study, transabdominal ultrasound image-guidance provides real-time imaging of the HIFU treatment. MRI provides imaging visualization of the HIFU thermal field and coagulated region within five seconds of treatment, and is thus not a real-time visualization. With ultrasound imaging, treating tumors with multiple lesions is facilitated, since the HIFU-induced hyperechoic spot remains after treatment for a duration dependent on the exposure intensity. Furthermore, treatment dosimetry, and not just treatment location, can be determined, since the hyperechoic spot size is proportional to the size of the lesion created. It was noted in the turkey breast that hyperechoic spots only appear above a specific intensity threshold (>1250 W/cm$^2$). Therefore, there is a possibility that exposures at lower doses may result in a physical lesion that cannot be visualized. This apparent intensity threshold will need to be determined in human uterus samples. The mechanisms behind the formation of hyperechoic spots are not well understood. However, it can be inferred from the in vitro testing in this study that the hyperechoic region during HIFU treatment is due to a combination of tissue properties changing due to tissue necrosis, cavitation activity, and gross deformation resulting in voids within the tissue. It is desirable to determine the location of the potential area of lesion formation prior to treatment. An electronic method using position transducers for targeting is currently being developed to enable the treatment area to be visualized without relying on the hyperechoic spot. Furthermore, computer-aided treatments that keep track of the treated areas on the ultrasound image may be employed in the future to compensate for any decrease in echogenicity in the hyperechoic spot.

The in vitro testing in gel demonstrated the feasibility of using the transvaginal HIFU transducer to form lesions. The testing on a turkey breast indicated a HIFU dose dependent lesion formation in tissue. It was shown that increasing the intensity or exposure time can increase lesion size. It was also shown that the intensity required for the onset of lesion formation was lower for a 10 second treatment duration (about 760 W/cm$^2$) versus a 5 second treatment duration (about 1170 W/cm$^2$). Lower HIFU intensities (ranging from about 760 W/cm$^2$ to about 2800 W/cm$^2$) resulted in cigar-shaped lesions that have been characterized as due to purely thermal effects. Higher HIFU intensities (i.e., above about 2800 W/cm$^2$) resulted in tadpole-shaped lesions, with a distinct head and tail that were characterized as lesions with a significant contribution from inertial cavitation activity and vaporization.

The thermal and cavitation effects at the focus and surrounding tissue will be subject to further investigation to determine optimal treatment parameters for uterine fibroids. Effective acoustic coupling from the HIFU transducer to the tissue of interest is crucial for successful treatment. Water is an effective acoustic coupler, due to its similarity in acoustic impedance to tissue. Since there was potential for air to be trapped between the transducer and the vaginal wall when the device was used in vivo, a method of acoustic coupling was devised using a water-filled condom that eliminated pockets of air, as described in further detail below. Testing of the device with the gel phantom revealed that the condom essentially acted as an acoustically transparent thin membrane that did not statistically affect the size of lesions. The condom further provided a sterile protective membrane. Focal depth control was possible by selectively inflating and deflating the condom with water and thus varying the distance between the transducer and the uterus, effectively varying the treatment location. Water circulation within the condom provides cooling to the transducer while in operation. Factors such as blood perfusion, air entrapment, and nonlinear effects of HIFU treatment need to be taken into consideration and may be the subjects of a future investigation.

The transvaginal therapy probe and frame described above can be used with commercially available transabdominal imaging probes in obstetrical and gynecological applications where necrosis of a region of tissue has a therapeutic benefit. Such applications include the treatment of the following conditions:

1. Uterine Fibroids, also known as Leiomyomas: benign tumors of muscle cell origin found in any tissue that contains smooth muscle such as the uterus. Fibroids are the most frequent pelvic tumors, with the highest incidence occurring during the fifth decade of a woman's life. Uterine fibroids may be single, but most often are multiple within the myometrium of the uterus. Fibroids are found in 25% of Caucasian women and 50% of African American women. They vary in size from about 1 cm to about 15 cm in diameter. They can rarely spontaneously necrose when they outgrow their blood supply, and they are considered to be estrogen-dependent tumors. Management is usually via a hysterectomy or a myomectomy.

2. Endometrial Polyps: A localized outgrowth of the endometrial glands and stroma projecting beyond the surface of the endometrium and including a vascular stalk. There may be single or multiple polyps in a woman's uterus. Polyps occur in all age groups, with a peak incidence between the ages of 40 and 49. Symptoms associated with polyps include abnormal bleeding patterns. Malignant transformation in an endometrial polyp is rare. Management is usually via surgical dilatation and curettage.

3. Follicular Cysts: By far the most frequent cystic structures seen in normal ovaries. Also, seen in abundance in polycystic ovary syndrome. The average size of a follicular cyst is about 2 cm in diameter. They are not neoplastic, but can cause symptoms if enlarged. When they rupture, they can cause intraperitoneal bleeding. Oral contraceptive agents are usually the first line of defense to prevent large cysts from forming.

4. PolyCystic Ovarian Syndrome (PCOS): This condition and its severe form, stromal hyperthecosis, are marked by multiple follicuar cysts. Adhesion formation is a serious complication of surgical treatment (ovarian drilling), resulting in continued infertility of PCOS patients. Those patients treated medically to ovulate are at higher risk for ovarian hyperstimulation syndrome, a potentially lethal condition.

5. Dermoid Cysts: A benign germ cell tumor within the ovary that may contain elements of all three germ cell layers. This tumor is also called mature teratoma. It is among the most common of ovarian neoplasms, representing 20-25% of all ovarian neoplasms and 33% of all benign tumors. They vary in diameter from a few millimeters to about 25 cm. They previously have required surgical excision.

6. Corpus Luteum Cysts: Less common than follicular cysts, but clinically important. They are usually associated with normal endocrine function or prolonged secretion of progesterone. They can reach from about 3 cm to about 10 cm in diameter and can rupture to cause intraperitoneal bleeding.

7. Ectopic Pregnancy: Pregnancy that develops following implantation of the blastocyst anywhere other than the endometrium lining the uterine cavity. The vast majority of ectopic pregnancies occur in a fallopian tube, although they can also occur in the ovary, abdominal peritoneal cavity, and the cervix.

8. Cornual Pregnancy: Pregnancy developing in the interstitial portion of the fallopian tube and the myometrium of the uterus. Like the tubal ectopic pregnancy, this type of pregnancy must be removed before it ruptures and causes massive bleeding.

9. Adenomyosis: The growth of endometrial glands and stroma in the uterine myometrium at a depth of at least 2.5 mm from the basalis layer of the endometrium. This condition is frequently associated with dysmenorrhea (painful menstrual cramps). It is generally treated with a hysterectomy.

10. Uterine AV Malformation: The presence of abnormal vasculature within the pelvis that results in abnormally heavy bleeding, usually requiring multiple transfusions. It has been treated with hysterectomy or radiographic embolization.

11. Endometriosis: The presence and growth of glands and stroma identical to the lining of the uterus in an ectopic location outside of the uterus. This condition is frequently associated with development of pelvic adhesions and pelvic pain. The patient frequently has dysmenorrhea or dyspareunia (pain with intercourse). Endometriomas are cysts within the ovary filled with endometriotic fluid and are also known as chocolate cysts, because of their appearance.

12. Endometrial Hyperplasia: This condition is a variety of patterns of epithelial and stromal proliferation having in common an abnormal increase in the cellular number within the endometrium. The cells can develop atypical features that can eventually develop into malignancy. This condition is frequently associated with irregular bleeding in women. In women who are past childbearing, hysterectomy or endometrial ablation is usually recommended.

13. Multifetal Pregnancy: With the advent of fertility drugs, women frequently achieve multiple pregnancy with twins, triplets, or an even greater number of gestational sacs. Selective reduction of these sacs is performed regularly due to the increased risk to both the mother and the babies that is incurred by this condition.

14. Excessive Bleeding: Can be due to a number of OB/GYN problems.

Additionally, the transvaginal therapy probe and frame of the present invention (when used in conjunction with a transabdominal imaging probe) can be used to treat malignant conditions of the female pelvis, such as leiomyosarcoma. Also, some genitourinary pathology can be treated with this invention.

The following modifications to the present invention are contemplated. The transvaginal therapy probe described above can be modified to include an imaging transducer, such that the imaging transducer and therapy transducer are located on the transvaginal probe. In such an embodiment, the frame and transabdominal imaging probe are not required. FIGS. 4A-5B, discussed in detail above, illustrate how therapy transducers and imaging transducers can be combined into a single transvaginal probe.

Still another modification of present invention might employ a frame substantially similar to frame 200 to control the spatial relationship between a transabdominal therapy probe and a transvaginal imaging probe. Those of ordinary skill in the art will readily recognize that many transvaginal imaging probes are commercially available. The therapy probe discussed in detail above has a focal length that was specifically selected for vaginal use. Those of ordinary skill in the art will readily recognize that therapy probes configured for transabdominal application will require a different focal length, because the HIFU beam from a transabdominal therapy probe will need to pass through layers of tissue and fat to reach a uterine fibroid. The techniques described above to select a focal length appropriate for vaginal use can also be used to determine a focal length appropriate for a transabdominal therapy probe configured to treat uterine fibroids.

Another modification that can be made to the present invention is to configure the frame that maintains the spatial orientation between the imaging probe and the therapy probe to accommodate a transabdominal imaging probe and transabdominal therapy probe. In FIG. 21A, both a HIFU transducer 102 and an imaging transducer 104 are disposed external to the patient's body. The reflected ultrasound waves received by imaging transducer 104 are used to generate an ultrasound image 100 shown schematically in FIG. 21B. In FIG. 21A, HIFU is being used to treat a tumor 110 on a uterus 111 of the patient. Imaging transducer 104 is positioned so that tumor 110 is clearly displayed in an ultrasound image. A focal point 112 of the HIFU is clearly visible in both the cross section of the body (FIG. 21A) and in ultrasound image 100 (FIG. 21B).

Note that in FIG. 21A, a frame 350 is used to control the spatial orientation between HIFU transducer 102 and imaging transducer 104. As described in detail above, once the desired spatial orientation is obtained, such that the focal point of the HIFU beam can be visualized in the ultrasound image, the frame maintains the spatial orientation between the HIFU transducer and the imaging transducer, so that movement of the patient, or either transducer, does not cause the focal point of the HIFU beam to move out of the imaging plane provided by the imaging transducer. Frame 350 includes three generally elongate arms 352, 365, and 364, and two brackets 354 and 356, which slidingly engage the generally elongate arms. While not separately shown, it will be understood that brackets 354 and 356 each include adjustment members (e.g., as described above in connection with frame 200), which enable a user to control whether the brackets lock the elongate arms in place, or slidingly engage the elongate arms. When these adjustment members are loosened, elongate arm 352 can slidingly engage brackets 354 and 356, as indicated by an arrow 358. When the adjustment member included in bracket 354 is loosened, elongate arm 362 can slidingly engage bracket 354, as indicated by an arrow 360. Similarly, when an adjustment member included in bracket 356 is loosened, elongate arm 364 can slidingly engage bracket 356, also as indicated by arrow 360.

A support bracket 366 is coupled to a distal end of elongate arm 364, and is configured to movably support a transabdominal imaging probe (i.e., imaging transducer 104). While not shown, it should be understood that support bracket 366 includes an adjustment member that when loosened, enables the transabdominal imaging probe to be selectively positioned as desired, and when secured, locks the transabdominal imaging probe in a desired position relative to frame 350. An arrow 372 generally indicates the motion of support bracket 366 when such an adjustment members is loosened. In at least one embodiment, arrow 372 can be understood to indicate a pivotal motion.

A support bracket 368 is similarly coupled to a distal end of elongate arm 362 and is configured to movably support a transabdominal therapy probe (e.g., HIFU transducer 102). While not shown, it should be understood that support bracket 368 also includes an adjustment member that when loosened, enables the transabdominal therapy probe to be selectively positioned as desired, and when secured, locks the transabdominal therapy probe in a desired position relative to frame 350. An arrow 370 generally indicates the motion of support bracket 368 when such an adjustment members is loosened. In at least one embodiment, arrow 370 can be understood to indicate a pivotal motion. If it is desired, a hinge 374 can be included within elongate arm 352 to provide further flexibility. While not specifically shown, if should be understood that frame 350 can be coupled to a fixed object for support, such as a table or equipment stand. Preferably elongate arm 362 is part of frame 350; however, in at least one embodiment elongate arm 362 is part of the transabdominal therapy probe (i.e., the transabdominal therapy probe includes HIFU transducer 102 and elongate arm 362, similar to the transvaginal therapy probe 204a, in which the HIFU transducer can pivot relative to the main elongate body of the probe, as discussed above).

Still another aspect of the present invention is directed to a method of verifying a quality of the coupling between an ultrasound therapy probe and a tissue interface. FIG. 23A schematically illustrates a transvaginal therapy probe 204b coupled to a tissue mass 406. Transvaginal therapy probe is substantially similar to transvaginal therapy probe 204 described above, however transvaginal therapy probe 204b further includes a liquid flushing line 251, whose purpose will be described in greater detail below. Transvaginal therapy probe 204b similarly includes housing 252 disposed at the distal end of transvaginal therapy probe 204b. Housing 252 encapsulates the therapy transducer. Expandable member 244 (i.e., a latex condom) is attached to housing 252, and filled with liquid to facilitate coupling transvaginal therapy probe 204b to tissue mass 406. With respect to transvaginal therapy probe 204, tissue mass 406 generally will be within the uterus. It should be understood that the method of verifying a quality of the coupling between an ultrasound therapy probe and a tissue interface is not limited to use with any specific therapy probe, or any specific tissue mass. Thus, the inclusion of transvaginal therapy probe 204 in FIG. 23A is intended to be exemplary, rather than limiting of the present invention.

A plurality of air bubbles 408 can be seen between expandable member 244 and tissue mass 406. The presence of such air bubbles at the interface between the therapy probe and the tissue mass will negatively affect the transmission of the HIFU beam through the interface, which will result in a degradation of the therapy being performed, because such air bubbles interfere with the propagation of the HIFU beam from the therapy transducer to the focal point/target area. The presence of air bubbles will reduce the amount of energy transmitted by the HIFU beam. Generally such air bubbles are most likely to be outside of the expandable member, in between the expandable measure member and the tissue mass. The liquid used to inflate the expandable member is preferably treated to remove any air bubbles in the liquid (i.e. the liquid is degassed), so it is more likely that air bubbles would become trapped outside of the expandable member, as opposed to inside the expandable member. To dislodge air bubbles trapped between the expandable member and the tissue interface, transvaginal therapy probe 204b can be manipulated such that the expandable member moves relative to the tissue mass, thereby dislodging any air bubbles. An additional technique that can be used to dislodge air bubbles would be to inflate or deflate the expandable member. Liquid flushing line 251 can be used to flush the interface with a rinse liquid to remove the air bubbles, as indicated by an arrow 253. If the air bubbles have formed inside of the expandable membrane, the liquid in the expandable membrane can be replaced with degassed liquid. Examination of the positions of the air bubbles relative to the interface and the expandable membrane will indicate whether the air bubbles are located in the liquid filling the membrane, or between the membrane and the tissue, so on appropriate corrective action can be taken.

FIG. 22 shows a flowchart 390 that indicates the sequence of logical steps to determine whether such air bubbles are present. In a block 392 a therapy probe is introduced into a body cavity, such as the vagina. While most often, therapy probes in accord with the present invention will be used within the body cavities, it should be understood that therapy probes can also be used in external applications, so that the therapy probe/tissue interface is outside the patient's body. Thus, it should be understood that the present invention is not limited to detecting air bubbles at tissue interfaces within a body cavity. In a block 394, the expandable member such (as a balloon or a latex condom) is inflated with a liquid (such as water or saline solution) that supports propagation of the HIFU beam. In some applications, the expandable member may be at least partially inflated with the liquid before the therapy probe is introduced into a body cavity, to provide a cushioning affect. In a block 395, the therapy probe is properly positioned relative to the tissue interface, so that the expandable member contacts the tissue interface and slightly deforms, thereby efficiently coupling the therapy probe to the tissue. In a block 396, the quality of the coupling between the expandable member and the tissue interface is evaluated, to determine if there are any air bubbles within the liquid. In a decision block 398, it is determined whether any such bubbles are present. If so, then in a block 400 appropriate action is taken to dislodge the air bubbles. Techniques for dislodging air bubbles include repositioning the therapy probe to dislodge the air bubbles, inflating or deflating the liquid-filled membrane to dislodge the air bubbles, and flushing the interface with an irrigation liquid to dislodge the air bubbles. An additional check is then made to determine whether any more air bubbles are present, after the therapy probe is repositioned. If, in decision block 398, it is determined that no such air bubbles are present, therapy is performed, as indicated in a block 402.

FIG. 23B schematically illustrates transvaginal therapy probe 204, including expandable member 244, coupled to tissue mass 406, such that no air bubbles are present at the tissue interface. Once administration of the therapy is completed, the probe is removed from the body cavity, as indicated in a block 404.

As noted in the details of block 396 (shown in FIG. 22), several different techniques can be used to check for the presence of air bubbles. A hysterscope can be used to optically check for the presence of air bubbles, as indicated in a block 396a. FIG. 24 is a photograph of a commercially available hysterscope 416. Those of ordinary skill in the art will recognize that a hysterscope is a relatively common gynecological instrument. Due to its widespread availability, most medical offices treating gynecological disorders will have access to such an instrument. Due to the small size of the hysterscope, it is quite feasible for both a transvaginal therapy probe and a hysterscope to be accommodated in the vaginal canal at the same time. The hysterscope provides real-time images, and can be manipulated so that the clinician can visually check for the presence of any air bubbles at the interface between the tissue mass and the therapy probe. If the clinician observes the presence of any air bubbles at the tissue/transvaginal therapy probe interface, the clinician can manipulate the transvaginal therapy probe to dislodge any air bubbles that were observed. While a rigid hysterscope is illustrated, it should be understood that flexible hysterscopes, or other flexible imaging devices, can be similarly employed for this purpose.

The therapy probe itself can also be used to check for the presence of air bubbles, when the therapy probe is energized at a low-power level, as indicated in a block 396b. When energized at a low-power level, the HIFU transducer transmits a low-power pulse. The reflected pulse is detected and analyzed. Either a therapy probe or an imaging probe can be used to detect the reflected pulse. If the intensity of the reflected pulse is higher than a predefined threshold level, it can be concluded that there are air bubbles disposed at the interface, and those air bubbles are responsible for the reflected pulse. For specific applications and equipment, the threshold level can be determined empirically. Otherwise, a reasonable threshold level would be a 15-20% increase in a background level. The HIFU beam is energized at a low-power setting to check for air bubbles, which ensures that tissue necrosis does not occur until a satisfactory coupling of the therapy probe to the tissue mass has been achieved and the HIFU beam is energized at a substantially higher intensity.

Still another technique for determining whether any air bubbles are present at the tissue/therapy probe interface involves using an ultrasound imaging probe, as indicated in a block 396c. The ultrasound imaging probe can either be integrated onto the therapy probe, as shown in FIGS. 4A-5B, or a separate ultrasound imaging probe can be employed, as shown in FIGS. 6-8 and 21A. Any air bubbles present at the tissue/therapy probe interface can be readily identified, because they will appear as bright spots in the ultrasound image. If an ultrasound imaging probe is used to determine whether any air bubbles are present, the therapy probe does not need to be energized at all during the check for air bubbles.

Another aspect of the present invention is directed to still another embodiment of a transvaginal therapy probe 410 that includes a generally spoon-shaped therapy transducer 412, a photograph of which is provided in FIG. 25A. FIG. 25B is a photograph of the distal end of transvaginal therapy probe 410, clearly showing generally spoon-shaped therapy transducer 412. FIG. 25C is a photograph showing transvaginal therapy probe 410 removably coupled to commercially available transvaginal imaging probe 120 (see FIG. 2 and the above text related to FIG. 2, for a description of the commercially available imaging probe), to enable visualization of the focal point of the HIFU beam during therapy, generally as described above. As indicated in FIG. 25C, the distal end of hysterscope 416 is also removably coupled to transvaginal therapy probe and the transvaginal imaging probe. A hook and loop fastener 414 is employed to removably couple the elements together. Those of ordinary skill in the art will readily recognize that other types of fasteners or mounting system can be similarly employed to removably couple the elements together. As noted above, it should be understood that in addition to hysterscope 416, other imaging devices can be used, such as optical fiber-based flexible scopes. The development of digital imaging devices is producing increasing smaller device, and if sufficiently small digital imaging devices become available, digital imaging devices can also be employed for this purpose.

FIG. 25D schematically illustrates generally spoon-shaped transducer 412 included in transvaginal therapy probe 410, clearly showing the plurality of different emitter elements that are included therein. Generally spoon-shaped transducer 412 includes 11 discrete emitter elements, all equal in area, each element being separated from its neighbors by 0.3 mm. Six of the emitter elements have complete annuli, and five emitter elements have truncated annuli. The overall transducer dimensions are about 35 mm×60 mm. Generally spoon-shaped transducer 412 is magnetic resonance image (MRI) compatible, has a center frequency of 3 MHz, a focal length of 3-6 cm, a geometric focus of 5 cm, and a maximum focal intensity of 3000 W/cm$^2$. Techniques for ensuring that a transducer is compatible with MRI are disclosed by Hynynen K, Darkazanli A, Schenck J F et al. MRI-guided noninvasive ultrasound surgery. *Med. Phys.*, vol. 20, pp. 107-115, 1993.

Still another aspect of the present invention is directed to an integration of a hysterscope (to optically determine whether air bubbles exist at a tissue interface), a transvaginal imaging probe, and a transvaginal therapy probe into a single compact instrument that is capable of optically determining whether any air bubbles exist at the instrument/tissue interface, and which enables visualization of the focal point of the HIFU beam during therapy. In a related embodiment, an optical imaging element is incorporated into a transvaginal therapy probe. Such an image imaging element can be based on a hysterscope, as described above, or based on an optical fiber, as well as sufficiently compact digital imaging electronics (i.e. the imaging components in a digital camera or a digital video camera). Thus, in reference to FIG. 25C, it should be understood that reference number 416 could be implemented using a rigid hysterscope, a flexible optical fiber, or compact digital imaging electronics.

Yet another aspect of the present invention is directed to a system and method that enables free hand registration of the imaging and therapy probes. FIG. 26 schematically illustrates a system 450 that facilitates such free hand registration. System 450 includes a HIFU therapy probe 452, an ultrasound imaging probe 456, a tracking system 454, and a display 460. It should be understood that any type of HIFU therapy probe (configured for internal or external use), and any type of ultrasound imaging probe (configured for internal or external use), can used in conjunction with system 450. Instead of using a physical or mechanical frame to maintain a spatial relationship between the HIFU therapy probe and the ultrasound imaging probe, system 450 relies on tracking system 454 to ensure that the spatial relationship between the HIFU therapy probe and the ultrasound imaging probe enables the focal point of the HIFU therapy probe to be visualized in the imaging plane generated by the ultrasound imaging probe. Tracking system 454 includes a processor that is able to keep track of the spatial relationship between the ultrasound imaging probe and the HIFU therapy probe. Such tracking systems are commercially available, and can be obtained from companies such as Ascension Technology, of Milton, Vt. Tracking systems for medical instruments are available based on several different technologies, including acoustic, light and magnetic based tracking systems, any of which could be used to implement tracking system 454. Magnetic based tracking systems (Ascension PC BIRD) that could be used for medical instruments are available from Mind Flux of Roseville, Australia.

System 450 functions as follows. HIFU therapy probe 452 and ultrasound imaging probe 456 are positioned relative to patient 458. The clinician can view an image 462 on a display 460. Image 462 includes a representation of patient 458, and the relative locations of ultrasound imaging probe 456 and HIFU therapy probe 452. Preferably image 462 will include a visual representation of the imaging plane provided by ultrasound imaging probe 456, and the HIFU beam generated by HIFU therapy probe 452. The clinician can determine from image 462 whether or not ultrasound imaging probe 456 and HIFU therapy probe 452 are properly aligned, such that the focal point of the HIFU beam can be visualized in an image provided by the ultrasound imaging probe. If the probes are not properly aligned, image 462 will provide the clinician a reference for determining how to reposition one or more of ultrasound imaging probe 456 and HIFU therapy probe 452, so that the focal point out the HIFU beam can be visualized in the ultrasound image. Depending on the size of display 460, the ultrasound image provided by ultrasound imaging probe 456 can be displayed along with image 462, or a separate display can be provided to display the ultrasound image generated by ultrasound imaging probe 456.

FIG. 27 is an enlarged view of display 460, including an image 463. The relative positions of ultrasound imaging probe 456, patient 458, and HIFU therapy probe 452 are presented in image 463. An image plane 466 provided by ultrasound imaging probe 456, a HIFU beam 468 provided by HIFU therapy probe 452, and a focal point 464 can be visualized in image 463. An optional message 470 informs the clinician that the probes are not properly aligned, which is apparent because imaging plane 466 and beam 468 do not overlap, and further, focal point 464 does not lie within image plane 466. While monitoring display 460 and image 463, the clinician can change the relative positions of ultrasound imaging probe 456 and HIFU therapy probe 452, until focal point 464 lies within imaging plane 466.

It should be noted image 463 is a two dimensional image, and those of ordinary skill in the art will readily recognized that even if the HIFU beam and the imaging plane overlap in two dimensions, they may not overlap in three dimension. When image 463 indicates that the imaging plane and the HIFU beam overlap, a clinician can view the ultrasound image provided by the ultrasound imaging probe, to determine whether or not the focal point of the HIFU beam can actually be visualized in the ultrasound image. If not, this provides an indication that the spatial relationship and orientation between the imaging plane and the HIFU beam are not properly aligned, and the clinician can further manipulate the relative positions of the imaging probe and the HIFU therapy probe, until the focal point of the HIFU beam both overlaps the imaging plane in image 463, and can be visualized in the ultrasound image provided by the ultrasound imaging probe. It should be also understood that tracking system 454 can provide additional images from different perspectives (or image 463 could be rotated by tracking system 454) to provide feedback to a clinician indicating which direction the ultrasound imaging probe and/or the therapy probe need to be manipulated, so that the HIFU beam can be visualized in the image provided by the ultrasound imaging probe.

System 450 offers several advantages, including ease-of-use, the ability to visualize complex treatment strategies, and the ability to visualize complex tumor and anatomy geometries.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for using ultrasound imaging to guide high intensity focused ultrasound (HIFU) to provide therapy to a treatment site associated with a patient, comprising the steps of:
   (a) positioning an ultrasound imaging transducer at a first location selected to enable an ultrasound image of the treatment site to be obtained;
   (b) positioning a HIFU transducer at a second location selected to enable a focal point of the HIFU transducer to be directed toward the treatment site;
   (c) generating an image of the treatment site using the ultrasound imaging transducer;
   (d) energizing the HIFU transducer at a power level selected such that no therapeutic effect is experienced by tissue exposed to the focal point of the HIFU transducer, while the imaging transducer generates an image of the treatment site;
   (e) determining if the focal point of the HIFU transducer can be visualized in the image generated by the imaging transducer, and if not, manipulating the position of at least one of the ultrasound imaging transducer and the HIFU transducer until the focal point of the HIFU transducer can be visualized in the image generated by the imaging transducer;
   (f) fixing a spatial relationship and orientation between the ultrasound imaging transducer and the HIFU transducer, using a frame, thereby ensuring that subsequent movement of the ultrasound imaging transducer, the HIFU transducer, or the patient will not change the spatial orientation between the ultrasound imaging transducer and the HIFU transducer, the frame comprising:

(i) a first bracket configured to selectively pivotably support an imaging probe including the imaging transducer; and (ii) a second bracket configured to movably support a therapy probe including the HIFU transducer; and (g) energizing the HIFU transducer at a power level sufficient to achieve the desired therapy, such that the HIFU transducer is synchronized relative to the ultrasound imaging transducer so that any noise in the image arising from energizing the HIFU transducer is shifted away from a disposition of the treatment site in the image.

2. The method of claim 1, wherein the step of fixing a spatial relationship and orientation between the ultrasound imaging transducer and the HIFU transducer further comprises the steps of tracking and displaying the spatial relationship and orientation between the ultrasound imaging transducer and the HIFU transducer, to provide feedback that a clinician can use to keep the spatial relationship and orientation properly aligned.

3. The method of claim 1, wherein at least a portion of the HIFU transducer is encapsulated in a liquid-filled flexible membrane, and wherein the step of positioning the HIFU transducer at the second location comprises the step of positioning the HIFU transducer adjacent to a tissue mass, such that the liquid-filled flexible membrane substantially conforms to a surface of the tissue mass, thereby ultrasonically coupling the HIFU transducer with the tissue mass.

4. The method of claim 3, wherein before the step of energizing the HIFU transducer at the power level sufficient to achieve the desired therapy, further comprising the step of determining whether any air bubbles exist at the interface between the liquid-filled flexible membrane and the surface of the tissue mass, and if so, dislodging any such air bubbles.

5. The method of claim 3, wherein the step of dislodging any such air bubbles comprises the step of repositioning the HIFU transducer.

6. The method of claim 3, wherein the step of dislodging any such air bubbles comprises the step of changing a volume of liquid in the liquid-filled flexible membrane.

7. The method of claim 3, wherein the step of dislodging any such air bubbles comprises the step of flushing the interface with a liquid.

8. The method of claim 1, wherein the step of positioning the ultrasound imaging transducer at the first location comprises the step of positioning the ultrasound imaging transducer externally of the patient.

9. The method of claim 1, wherein the step of positioning the HIFU transducer at the second location comprises the step of positioning the HIFU transducer externally of the patient.

10. The method of claim 9, wherein the step of positioning the ultrasound imaging transducer at the first location comprises the step of positioning the ultrasound imaging transducer externally of the patient.

11. The method of claim 1, wherein the step of positioning the ultrasound imaging transducer at the first location comprises the step of positioning the ultrasound imaging transducer adjacent to the patient'abdomen, and the step of positioning the HIFU transducer at the second location comprises the step of positioning the HIFU transducer within the patient'vaginal canal.

12. The method of claim 1, wherein the step of manipulating the position of at least one of the ultrasound imaging transducer and the HIFU transducer until the focal point of the HIFU transducer can be visualized in the image generated by the imaging transducer comprises the step of keeping a main body of a probe to which the HIFU transducer is attached in a fixed position, while moving the HIFU transducer.

13. The method of claim 1, wherein the step of manipulating the position of at least one of the ultrasound imaging transducer and the HIFU transducer until the focal point of the HIFU transducer can be visualized in the image generated by the imaging transducer comprises the step of pivoting at least one of the ultrasound imaging transducer and the HIFU transducer relative to the frame configured to maintain a spatial relationship and orientation between the HIFU transducer and the imaging transducer.

14. The method of claim 1, further comprising the step of moving a position of the focal point of the HIFU transducer relative to the treatment site, to provide therapy to a different portion of the treatment site, by moving the HIFU transducer while keeping a main body of a probe to which the HIFU transducer is attached in a fixed position.

15. A method for using ultrasound imaging to guide high intensity focused ultrasound (HIFU) to provide therapy to a treatment site associated with a patient, comprising the steps of:

(a) positioning an ultrasound imaging transducer at a first location selected to enable an ultrasound image of the treatment site to be obtained;

(b) positioning a HIFU transducer at a second location selected to enable a focal point of the HIFU transducer to be aimed toward the treatment site;

(c) generating an image of the treatment site using the ultrasound imaging transducer;

(d) energizing the HIFU transducer at a power level selected such that no therapeutic effect is experienced by tissue exposed to the focal point of the HIFU transducer, while the imaging transducer generates an image of the treatment site;

(e) determining if the focal point of the HIFU transducer can be visualized in the image generated by the imaging transducer, and if not, pivoting at least one of the ultrasound imaging transducer and the HIFU transducer relative to a frame configured to maintain a spatial relationship and orientation between the HIFU transducer and the imaging transducer, until the focal point of the HIFU transducer can be visualized in the image generated by the imaging transducer;

(f) mechanically fixing a then current spatial relationship and orientation between the ultrasound imaging transducer and the HIFU transducer, using the frame, thereby ensuring that subsequent movement of the ultrasound imaging transducer, the HIFU transducer, or the patient will not change the spatial orientation between the ultrasound imaging transducer and the HIFU transducer, the frame comprising:

(i) a first bracket configured to selectively pivotably support an imaging transducer; and (ii) a second bracket configured to movably support a HIFU transducer; and (g) energizing the HIFU transducer at a power level sufficient to achieve the desired therapy.

16. The method of claim 15, wherein before energizing the HIFU transducer at the power level sufficient to achieve the desired therapy, further comprising the step of determining whether any air bubbles exist in an interface provided by a liquid-filled flexible membrane coupling the HIFU transducer to a tissue mass, and if so, dislodging any such air bubbles.

17. The method of claim 16, wherein the step of dislodging any such air bubbles comprises at least one of the following steps:
- (a) changing a volume of liquid in the liquid-filled flexible membrane;
- (b) flushing the interface with a liquid; and
- (c) repositioning the HIFU transducer.

18. The method of claim 15, wherein at least one of the following is true:
- (a) the step of positioning the ultrasound imaging transducer at the first location comprises the step of positioning the ultrasound imaging transducer externally of the patient;
- (b) the step of positioning the HIFU transducer at the second location comprises the step of positioning the HIFU transducer externally of the patient; and
- (c) the step of energizing the HIFU transducer to at a power level sufficient to achieve the desired therapy comprises the step of synchronizing the HIFU transducer relative to the ultrasound imaging transducer so that any noise in the image arising from energizing the HIFU transducer is shifted away from the treatment site in the image.

19. A method for using ultrasound imaging to guide high intensity focused ultrasound (HIFU) to provide therapy to a treatment site associated with a patient, comprising the steps of:
- (a) positioning an ultrasound imaging transducer at a first location selected to enable an ultrasound image of the treatment site to be obtained;
- (b) positioning a HIFU transducer at a second location selected to enable a focal point of the HIFU transducer to be aimed toward the treatment site;
- (c) generating an image of the treatment site using the ultrasound imaging transducer;
- (d) energizing the HIFU transducer at a power level selected such that no therapeutic effect is experienced by tissue exposed to the focal point of the HIFU transducer, while the imaging transducer generates an image of the treatment site;
- (e) determining if the focal point of the HIFU transducer can be visualized in the image generated by the imaging transducer, and if not, manipulating the position of at least one of the ultrasound imaging transducer and the HIFU transducer until the focal point of the HIFU transducer can be visualized in the image generated by the imaging transducer;
- (f) mechanically fixing a then current spatial relationship and orientation between the ultrasound imaging transducer and the HIFU transducer, using a frame, thereby ensuring that subsequent movement of the ultrasound imaging transducer, the HIFU transducer, or the patient will not change the spatial orientation between the ultrasound imaging transducer and the HIFU transducer, the frame comprising:
    - (i) a first bracket configured to selectively pivotably support an imaging probe including the imaging transducer; and
    - (ii) a second bracket configured to movably support a therapy probe including the HIFU transducer;
- (g) energizing the HIFU transducer at a power level sufficient to achieve the desired therapy; and
- (h) wherein at least one of the following is true:
    - (i) the step of positioning the ultrasound imaging transducer at the first location comprises the step of positioning the ultrasound imaging transducer externally of the patient;
    - (ii) the step of positioning the HIFU transducer at the second location comprises the step of positioning the HIFU transducer externally of the patient;
    - (iii) the step of manipulating the position of at least one of the ultrasound imaging transducer and the HIFU transducer until the focal point of the HIFU transducer can be visualized in the image generated by the imaging transducer comprises the step of pivoting at least one of the ultrasound imaging transducer and the HIFU transducer relative to the frame configured to maintain the spatial relationship and orientation between the HIFU transducer and the imaging transducer; and
    - (iv) the step of energizing the HIFU transducer to at a power level sufficient to achieve the desired therapy comprises the step of synchronizing the HIFU transducer relative to the ultrasound imaging transducer so that any noise in the image arising from energizing the HIFU transducer is shifted away from the treatment site in the image.

20. A medical device support frame configured to fix a spatial relationship and orientation between an ultrasound imaging probe and an ultrasound therapy probe when the ultrasound imaging probe and the ultrasound therapy probe are positioned relative to a patient, thereby ensuring that once at least one of the ultrasound imaging probe and the ultrasound therapy probe has been adjusted so that a focal point of the ultrasound therapy probe is visualized in an imaging plane of the ultrasound imaging probe, subsequent movement of the ultrasound imaging probe, the ultrasound therapy probe, or the patient will not change the spatial orientation between the ultrasound imaging probe and the ultrasound therapy probe, the frame comprising:
- (a) a first medical device support bracket adapted to selectively pivotably support an imaging probe that is disposed external to a patient's body;
- (b) a second medical device support bracket adapted to movably support a therapy probe that is disposed internal to a patient's body;
- (c) a first generally elongate support, pivotably coupled to the first medical device support bracket;
- (d) a second generally elongate support, movably coupled with the second medical device support bracket; and
- (e) a common bracket, slidingly engaging the first and second generally elongate supports, such that the medical device support frame does not need to be coupled to a fixed object in order to fix the spatial relationship and orientation between the imaging probe and the therapy probe relative to each other, thereby enabling a self-referencing medical device support frame to be achieved.

21. The frame of claim 20, wherein the second medical device support bracket is pivotably coupled to the second generally elongate support.

22. The frame of claim 21, further comprising a common support, the first and second generally elongate supports independently slidingly engaging the common support.

23. The frame of claim 22, wherein the common support is hinged, to enable a spatial relationship between the first and second generally elongate supports to be changed.

24. The frame of claim 20, wherein the common bracket includes an orifice that is configured to slidingly engage one of the first and second generally elongate supports.

25. The frame of claim 20, wherein the common bracket comprises a channel configured to slidingly engage one of the first and second generally elongate supports.

26. The frame of claim 20, wherein the second generally elongate support includes an angled bend so that the second generally elongate support is not straight.

27. The frame of claim 20, wherein the second generally elongate support includes a channel.

28. The frame of claim 20, wherein the first generally elongate support can be translated generally normal to the second generally elongate support.

29. A medical device support frame adapted to fix a spatial relationship and orientation between an ultrasound imaging probe and an ultrasound therapy probe when the ultrasound imaging probe and the ultrasound therapy probe are positioned as desired relative to a patient, thereby ensuring that once a focal point of the ultrasound therapy probe is visualized in an imaging plane of the ultrasound imaging probe, subsequent movement of the ultrasound imaging probe, the ultrasound therapy probe, or the patient does not change the spatial relationship and orientation between the ultrasound imaging probe and the ultrasound therapy probe, the frame comprising:
- (a) a first medical device support bracket adapted to support an imaging probe that is disposed external to a patient's body, the first medical device support bracket being pivotably coupled to a first generally elongate support and being adapted to be coupled to the imaging probe such that the imaging probe can be pivoted about a longitude axis of the first generally elongate support; and
- (b) a second medical device support bracket adapted to movably support a therapy probe that is disposed internal to a patient's body, such that the first generally elongate support can be translated in a direction generally normal to a second generally elongate support.

30. The frame of claim 29, wherein the second medical device support bracket is configured to slidingly engage the therapy probe including a generally elongate main body.

31. The frame of claim 29, further comprising a third bracket, the first and second generally elongate supports slidingly engaging the third bracket.

32. The frame of claim 31, wherein the third bracket comprises an orifice that is configured to slidingly engage one of the first and second generally elongate supports.

33. The frame of claim 31, wherein the first generally elongate support comprises a pair of parallel arms, and the third bracket comprises a pair of channels configured to slidingly engage the pair of parallel arms.

34. A system configured to be used with an ultrasound imaging probe to enable ultrasound imaging to guide high intensity focused ultrasound (HIFU) to provide therapy to a treatment site, the system comprising:
- (a) a therapy probe comprising a HIFU transducer; and
- (b) a medical device support frame adapted to selectively fix a spatial orientation between an ultrasound imaging probe and the therapy probe, thereby ensuring that after the frame, the therapy probe, and an ultrasound imaging probe are properly positioned relative to a patient so that a focal point of the therapy probe is visualized in an imaging plane of an ultrasound imaging probe, subsequent movement of an ultrasound imaging probe, the therapy probe, or the patient does not change the spatial orientation between an ultrasound imaging probe and the therapy probe, the frame comprising:
  - (i) a first medical device support bracket adapted to support the imaging probe that is disposed external to a patient's body, the first medical device support bracket being pivotably coupled to a first generally elongate support and being adapted to be coupled to the imaging probe such that the imaging probe can be pivoted about a longitudinal axis of the first generally elongate support; and
  - (ii) a second medical device support bracket adapted to movably support the therapy probe that is disposed internal to a patient's body.

35. The system of claim 34, wherein the HIFU transducer comprises at least one of the following:
- (a) an air backed piezoceramic crystal coupled to an aluminum lens element; and
- (b) a generally spooned-shaped transducer comprising a plurality of discrete emitter elements, each emitter element having a substantially equivalent area.

36. The system of claim 34, wherein the therapy probe further comprises:
- (a) a generally elongate body, the HIFU transducer being disposed proximate a distal end of the generally elongate body;
- (b) a flexible membrane substantially encapsulating the distal end of the generally elongate body, the flexible membrane being configured to be inflated with a liquid when the distal end of the generally elongate body is disposed adjacent to a tissue mass, such that the flexible membrane will substantially conform to the tissue mass, thereby coupling the HIFU transducer to the tissue mass; and
- (c) an imaging element configured to enable an interface between the flexible membrane and the tissue mass to be examined, to determine whether any air bubbles are present at the interface.

37. The system of claim 36, wherein the therapy probe comprises a liquid flushing line configured to discharge a flushing liquid proximate the flexible membrane, to dislodge any air bubbles that could interfere with a HIFU beam generated by the HIFU transducer.

38. The system of claim 36, wherein the imaging element comprises an optical fiber.

39. The system of claim 36, wherein the imaging element comprises a digital imaging device.

40. The system of claim 34, wherein the frame is configured such that the first generally elongate support can be translated generally normal to the second generally elongate support.

41. A method for using ultrasound imaging to guide high intensity focused ultrasound (HIFU) to provide therapy to a treatment site associated with a patient; comprising the steps of:
- (a) positioning an ultrasound imaging transducer at a first location selected to enable an ultrasound image of the treatment site to be obtained;
- (b) positioning a HIFU transducer at a second location selected to enable a focal point of the HIFU transducer to be directed toward the treatment site;
- (c) generating an image of the treatment site using the ultrasound imaging transducer;
- (d) energizing the HIFU transducer at a power level selected such that no therapeutic effect is experienced by tissue exposed to the focal point of the HIFU transducer, while the imaging transducer generates an image of the treatment site;
- (e) determining if the focal point of the HIFU transducer can be visualized in the image generated by the imaging transducer, and if not, manipulating the position of at least one of the ultrasound imaging transducer and the HIFU transducer until the focal point of the HIFU transducer can be visualized in the image generated by the imaging transducer;

(f) tracking and displaying the spatial relationship and orientation between the ultrasound imaging transducer and the HIFU transducer, to provide feedback that a clinician can use to keep the spatial relationship and orientation properly aligned;

(g) when the spatial relationship and orientation of the ultrasound imaging transducer and the HIFU transducer are properly aligned, mechanically fixing that spatial relationship and orientation using a frame, thereby ensuring that subsequent movement of the ultrasound imaging transducer, the HIFU transducer, or the patient will not change the spatial orientation between the ultrasound imaging transducer and the HIFU transducer, the frame comprising:

(i) a first bracket configured to selectively pivotably support an imaging probe including the imaging transducer; and (ii) a second bracket configured to movably support a therapy probe including the HIFU transducer; and (h) energizing the HIFU transducer at a power level sufficient to achieve the desired therapy.

42. A system for image guided high intensity focused ultrasound (HIFU) therapy comprising:

(a) an ultrasound imaging probe;

(b) a first display upon which a first image generated by the ultrasound imaging probe is to be displayed;

(c) a therapy probe including a HIFU transducer;

(d) a processor configured to:

(i) track a spatial relationship and orientation between the ultrasound imaging probe and the therapy probe; and (ii) provide a signal configured to produce a second image indicating the spatial relationship and orientation between the ultrasound imaging probe and the therapy probe;

(e) a second display on which the second image indicating the spatial relationship and orientation between the ultrasound imaging probe and the therapy probe is displayed, the second image providing feedback that a clinician can use to maintain a desired spatial relationship and orientation between the ultrasound imaging probe and the therapy probe; and (f) a frame configured to selectively fix a spatial orientation between the ultrasound imaging probe and the therapy probe, thereby ensuring that after the frame, the therapy probe, and the ultrasound imaging probe are properly positioned relative to a patient so that a focal point of the therapy probe is visualized in an imaging plane of the ultrasound imaging probe, subsequent movement of the ultrasound imaging probe, the therapy probe, or the patient does not change the spatial orientation between the ultrasound imaging probe and the therapy probe, the frame comprising:

(i) a first bracket configured to support the imaging probe, the first bracket being coupled to a first generally elongate support; and (ii) a second bracket configured to movably support the therapy probe, such that the first generally elongate support can be translated generally normal to the second generally elongate support.

43. The system of claim 42, wherein the first display and the second display are implemented as a single display on which the first image and second image are simultaneously displayed.

44. A system configured to be used with a conventional ultrasound imaging probe to enable ultrasound imaging to guide high intensity focused ultrasound (HIFU) to provide therapy to a treatment site associated with a female anatomy, the system comprising:

(a) a transvaginal therapy probe comprising a generally elongate housing and a HIFU transducer disposed at a distal end of the generally elongate housing; and (b) a medical device support frame adapted to selectively fix a spatial orientation between an ultrasound imaging probe and the transvaginal therapy probe, thereby ensuring that after the frame, the transvaginal therapy probe, and a conventional ultrasound imaging probe are properly positioned relative to a patient so that a focal point of the transvaginal therapy probe is visualized in an imaging plane of a conventional ultrasound imaging probe, subsequent movement of an ultrasound imaging probe, the transvaginal therapy probe, or the patient does not change the spatial orientation between a conventional ultrasound imaging probe and the ultrasound therapy probe, the frame comprising:

(i) a first medical device support bracket adapted to support a conventional imaging probe that is disposed external to a patient's body, the first medical device support bracket being pivotably coupled to a first generally elongate support and being adapted to be coupled to the imaging probe such that the imaging probe can be pivoted about a longitudinal axis of the first generally elongate support; and (ii) a second medical device support bracket adapted to movably support the transvaginal therapy probe, such that the first generally elongate support can be translated in a direction generally normal to the second generally elongate support.

* * * * *

UNITED STATES PATENT AND TRADEMARK OFFICE
CERTIFICATE OF CORRECTION

PATENT NO. : 7,520,856 B2
APPLICATION NO. : 10/977339
DATED : April 21, 2009
INVENTOR(S) : Vaezy et al.

It is certified that error appears in the above-identified patent and that said Letters Patent is hereby corrected as shown below:

| | |
|---|---|
| Column 1, lines 23-27 (Government Rights section) | Please delete text as it appears, and replace in its entirety with --This invention was made with U.S. Government support under grant No. N00014-01-G-0460 and N00014-01-96-0630 from the Department of the Navy, and grant No. 2 R42 HD38440-02 from the National Institutes of Health. The U.S. Government has certain rights in the invention.-- |
| Column 5, line 63 | after "25A;" delete "and" |
| Column 7, line 17 | "filed" should read --field-- |
| Column 10, line 51 | "10a" should read --110a-- |
| Column 10, line 52 | "10a" should read --110a-- |
| Column 10, line 53 | "10a" should read --110a-- |
| Column 14, line 2 | after "of" insert --the-- |
| Column 16, line 47 | "formix" should read --fornix-- |
| Column 17, line 25 | "formix" should read --fornix-- |
| Column 18, line 65 | after "to" delete --a-- |
| Column 21, line 41 | after "application" insert --of-- |
| Column 23, line 12 | "formix" should read --fornix-- |
| Column 27, line 35 | "members" should read --member-- |
| Column 27, line 47 | "members" should read --member-- |
| Column 27, line 51 | "if" should read --it-- |
| Column 27, line 64 | after "probe" insert --204b-- |

UNITED STATES PATENT AND TRADEMARK OFFICE
CERTIFICATE OF CORRECTION

PATENT NO. : 7,520,856 B2
APPLICATION NO. : 10/977339
DATED : April 21, 2009
INVENTOR(S) : Vaezy et al.

It is certified that error appears in the above-identified patent and that said Letters Patent is hereby corrected as shown below:

| | |
|---|---|
| Column 28, line 47 | "on" should read --an-- |
| Column 30, lines 30-31 | "increasing smaller device" should read --increasingly smaller devices-- |
| Column 31, line 10 | after "can" insert --be-- |
| Column 31, line 67 | "recognized" should read --recognize-- |
| Column 32, line 2 | "dimension" should read --dimensions-- |
| Column 33, line 60 (Claim 11, line 7) | "patient'" should read --patient's-- |

Signed and Sealed this

Twenty-third Day of June, 2009

JOHN DOLL
*Acting Director of the United States Patent and Trademark Office*